(12) United States Patent
Sorrentino et al.

(10) Patent No.: US 6,933,150 B1
(45) Date of Patent: Aug. 23, 2005

(54) RELATIONSHIP OF ABC TRANSPORT PROTEINS WITH HEMATOPOIETIC STEM CELLS AND METHODS OF USE THEREOF

(75) Inventors: Brian Sorrentino, Memphis, TN (US); Kevin Bunting, Columbus, MD (US); John Schuetz, Memphis, TN (US); Hiromitsu Nakauchi, Kukizaki-machi (JP)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 09/584,586

(22) Filed: May 31, 2000

Related U.S. Application Data

(63) Continuation-in-part of application No. PCT/US99/11825, filed on May 27, 1999.
(60) Provisional application No. 60/086,988, filed on May 28, 1998.

(51) Int. Cl.[7] ............................. C12N 5/00; C12N 5/08; C12N 15/63; C12N 15/85; C12N 15/87
(52) U.S. Cl. ...................... 435/455; 424/93.6; 435/372; 435/383
(58) Field of Search ................................. 435/455, 325, 435/366, 372, 383, 320.1, 440, 354, 355; 424/93.1, 93.2, 93.6, 93.21; 514/44

(56) References Cited

U.S. PATENT DOCUMENTS

| | | | | |
|---|---|---|---|---|
| 5,837,536 A | * | 11/1998 | McDonagh et al. | ........ 435/325 |
| 6,313,277 B1 | | 11/2001 | Abruzzo et al. | |

FOREIGN PATENT DOCUMENTS

| | | |
|---|---|---|
| WO | 93/24613 | 12/1993 |
| WO | 97/16535 | 5/1997 |
| WO | 98/12304 | 3/1998 |
| WO | WO 99/40110 | 8/1999 |
| WO | 99/61589 | 12/1999 |

OTHER PUBLICATIONS

Hanazono et al.; Gene Transfer into Nonhuman Primate Hematopoietic Stem Cells: Implications for Gene Therapy 2001 Stem Cells 19: 12–22.*
Bunting et al., Transduction of murine bone marrow cells with and MDR1 vector enables ex vivo stem cell expansion but these expanded grafts cause a myeloproliferative syndrome in transplanted mice, 1998, BLOOD, vol. 92, pp 2269–2279.*
U.S. Appl. No. 60/086,988, filed May 28, 1998.
Allen et al., Cancer Res., 59:4237–41, 1999.
Allikmets et al., Hum. Mol. Genet., 5: 1649–55, 1996.
Bhatia et al., Nat Med.,, 4: 1038–45, 1998.
Bhatia et al., J Exp. Med., 186: 619–624, 1997.
Brangi et al., Cancer Research, 59:5938–5946, 1999.
Bunting et al., Blood, 92(7): 2269–79, 1998.
Chaudhary and Roninson, Cell, 66: 85–94, 1991.
Doyle et al., Proc. Natl. Acad. Sci. USA, 95: 15665–15670, 1998.
Galipeau et al., Human Gene Therapy., 8: 1773–83, 1997.
Giles et al., Cancer, 86: 805–813, 1999.
Glimm and Eaves, Blood, 94: 2161–68, 1999.
Goodell et al., J Exp Med., 183: 1797–1806, 1996.
Goodell et al., Nat. Med., 3: 1337–45, 1997.
Gruol and Bourgeois, Biochem. Cell. Biol., 72: 561–71, 1994.
Gussoni et al, Nature, 401: 390–4, 1999.
Hanania et al., Cancer Gene Therapy, 1(1): 21–25, 1994.
Hanania et al., Gene Ther., 2: 279–84, 1995.
Hrycyna et al., Biochemistry, 37: 13660–73, 1998.
Jackson et al., PNAS USA, 96: 14482–86, 1999.
Johnstone et al., Blood, 93: 1075–85, 1999.
Leith et al., Blood, 94: 1086–99, 1999.
Malieparard et al., Cancer Res., 59: 4559–63, 1999.
Michieli et al., Br. J. Haematol, 104: 328–335, 1999.
Miyake et al., Cancer Res., 59: 8–13, 1999.
Nakayama et al., Blood, 92: 4296–4307, 1998.
Osawa et al., Science, 273: 242–45, 1996.
Persons et al., Blood, 90(5):1777–1786, 1997.
Podda et al., PNAS USA, 89:9676–80, 1992.
Robinson et al., Biochemistry, 30: 11169–78, 1997.
Ross et al., Blood, 96(1):365–368, 2000.
Schinkel et al., PNAS USA, 94: 4028–33, 1997.
Shimizu et al., Blood, 91: 3688–92, 1998.
Smyth et al., PNAS USA, 95: 7024–29, 1998.
Sorrentino et al., Science, 257: 99–103, 1992.
Sorrentino et al., Blood, 86: 491–501, 1995.
Spencer et al., Blood, 87: 2579–87, 1996.
Tisdale et al., Blood, 92: 1131–41, 1998.
Traycoff et al., Exp. Hemotol., 26:53–62, 1998.
Zandstra et al., Proc. Natl. Acad. Sci. USA, 94:4698–4703, 1997.
Zanjani et al., Exp. Hematol., 26: 353–60, 1998.
Ziegler et al., Science, 285: 1553–8, 1999.

* cited by examiner

*Primary Examiner*—Anne-Marie Falk
(74) *Attorney, Agent, or Firm*—Licata & Tyrrell P.C.

(57) ABSTRACT

The present invention includes methods of performing ex vivo expansion of gene-modified hematopoietic stem cells which are useful for many applications involving bone marrow transplantation and ex vivo gene therapy. The present invention further includes the gene-modified hematopoietic stem cells that are used and produced by such methods. Such gene-modified hematopoietic stem cells can also contain a second heterologous gene. In addition, the present invention also includes methods of engrafting the gene-modified hematopoietic stem cells of the present invention into animals, including for ex vivo gene therapy and for reconstitution of hematopoietic cells in ablated mammals. The present invention also provides a method of isolating stem cells.

15 Claims, 29 Drawing Sheets

FIG. 1A

Total Cells
- ● MDR-transduced
- ○ DHFR-transduced

Fold Expansion vs Days of Culture

FIG. 1B

Drug-Resistant CFU-Cs
- ● MDR-transduced
- ○ DHFR-transduced

Fold Expansion vs Days of Culture

FIG. 3A
FIG. 3B
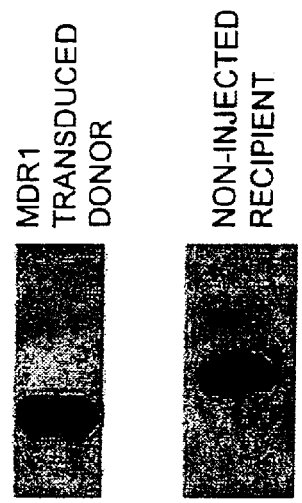
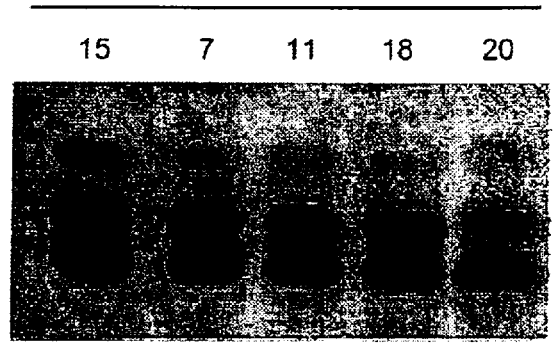
RECIPIENTS INJECTED WITH
MDR1 EXPANDED MARROW
15  7  11  18  20
FIG. 3C
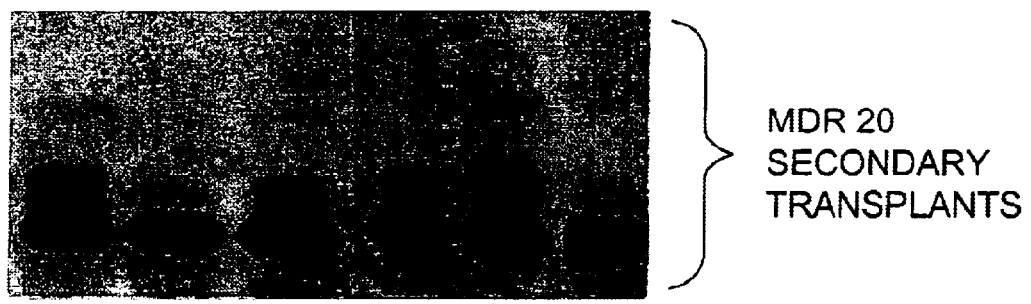
MDR 20
SECONDARY
TRANSPLANTS

EVENTS

EVENTS

EVENTS

EVENTS

EVENTS

PgP Fluoresence

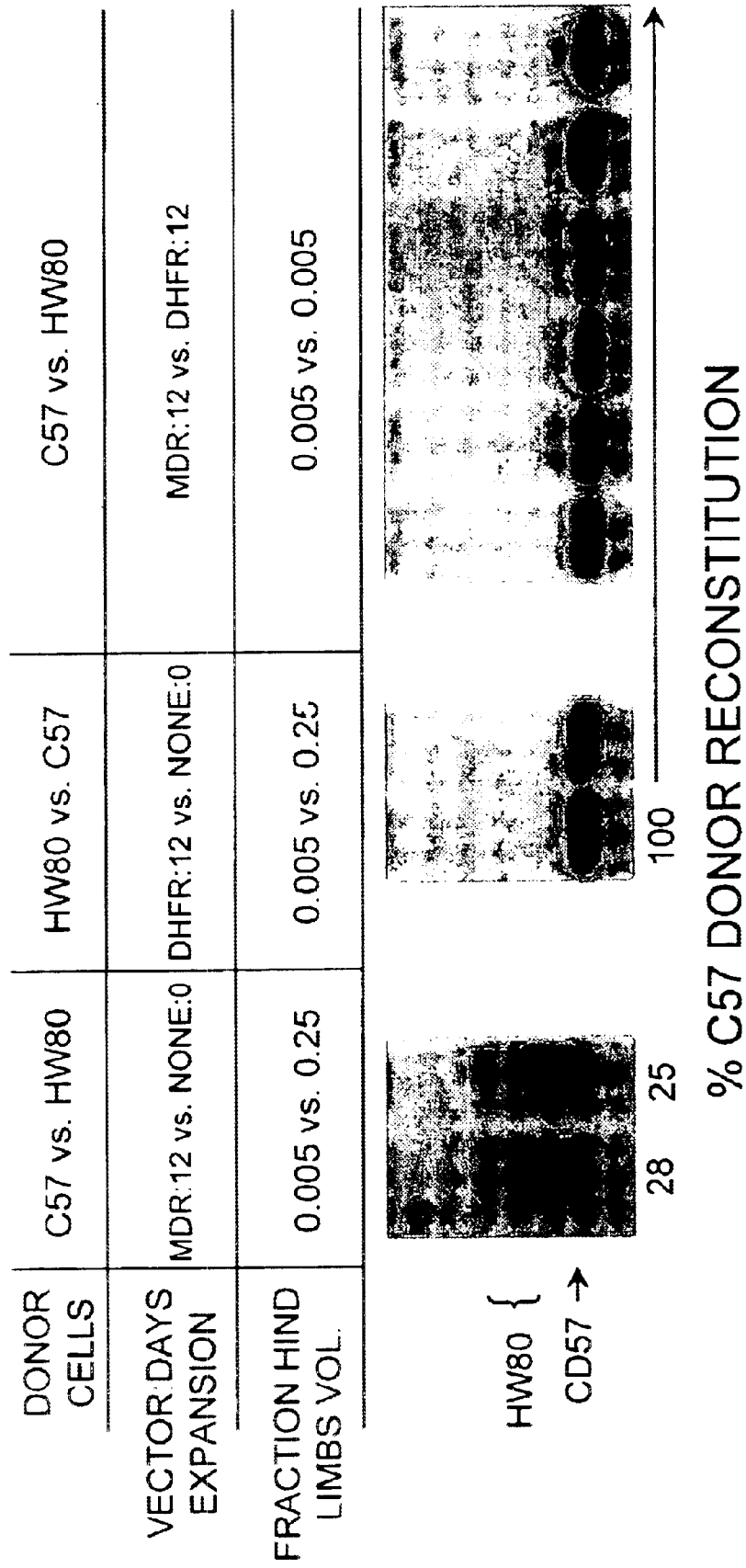

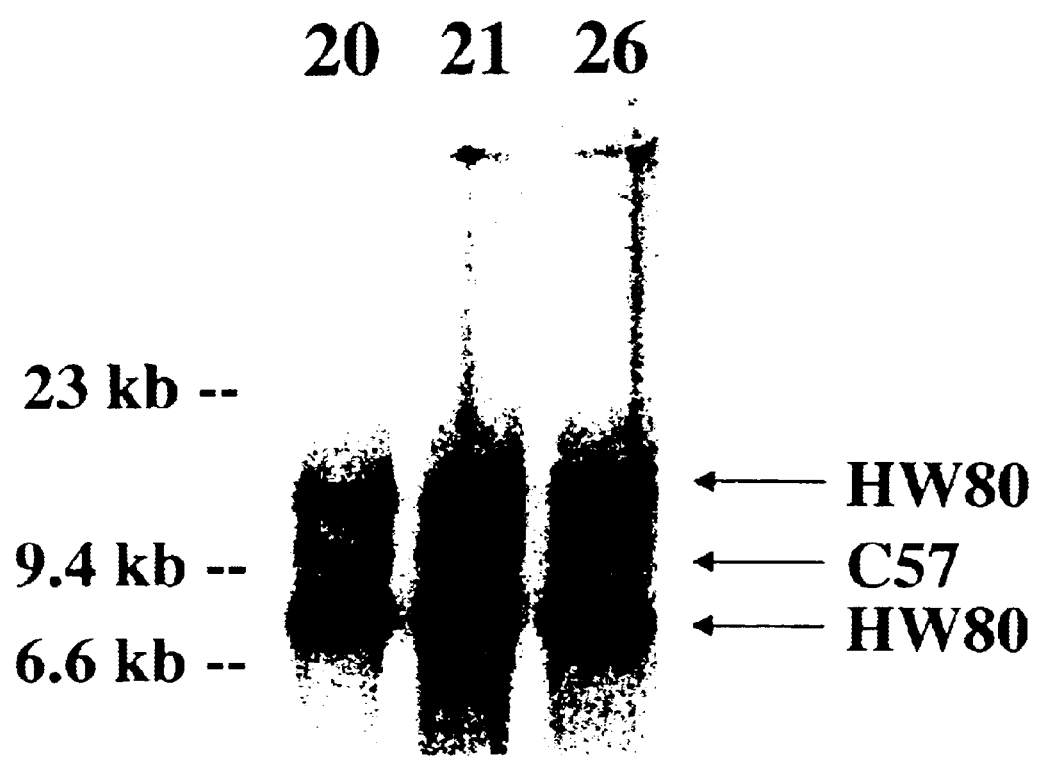

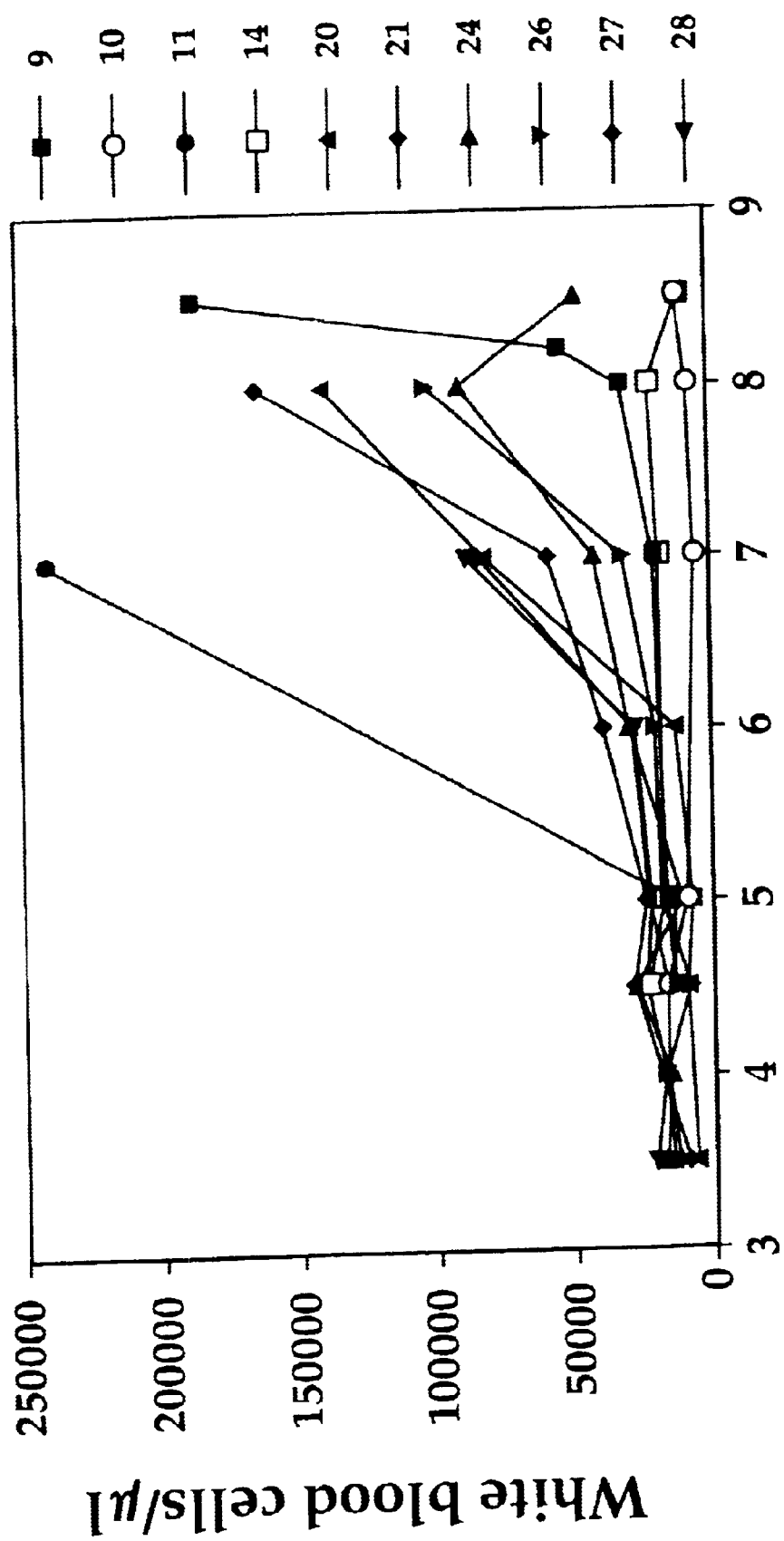

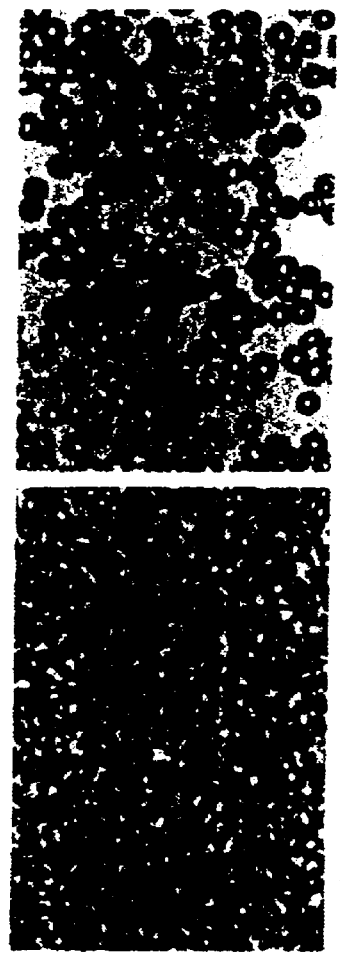
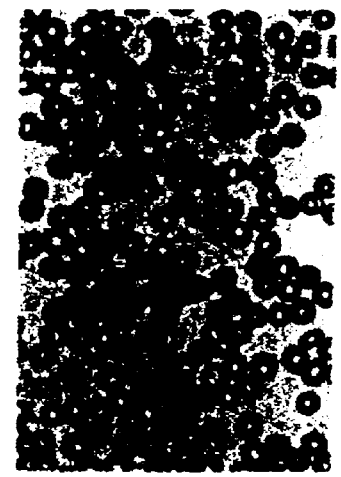
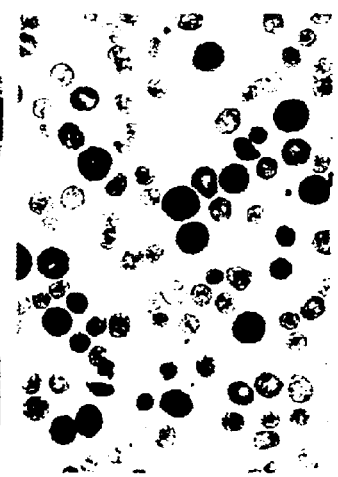
FIG. 7B-1 Normal
FIG. 7B-2 Normal
FIG. 7B-3 Abnormal
FIG. 7B-4 Abnormal
FIG. 7B-5 Abnormal
FIG. 7B-6 Abnormal FIG. 9A
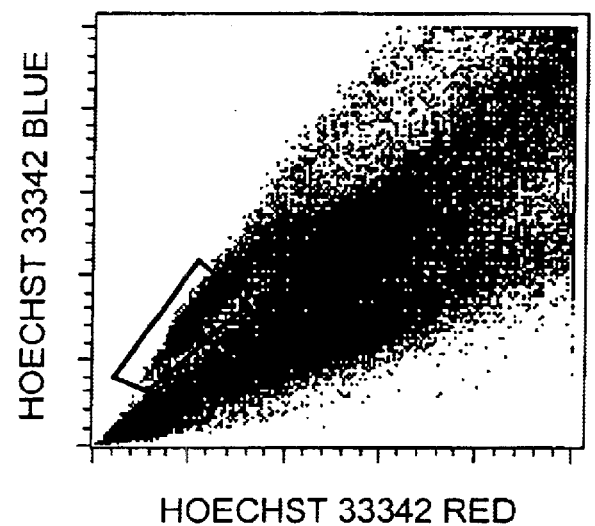
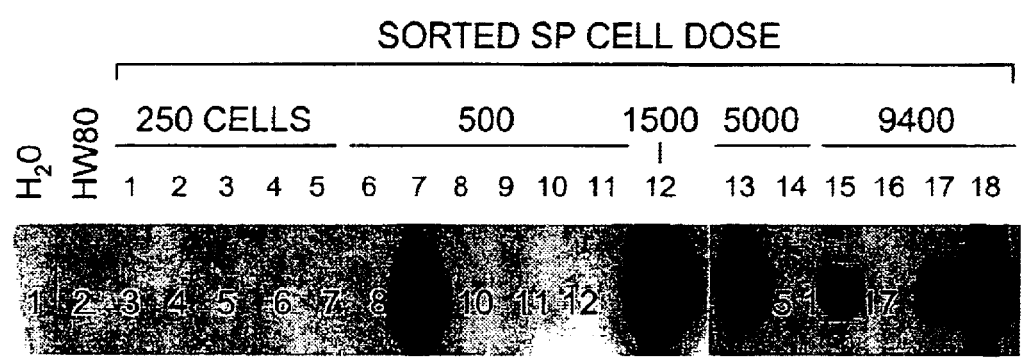

*

FIG. 22A
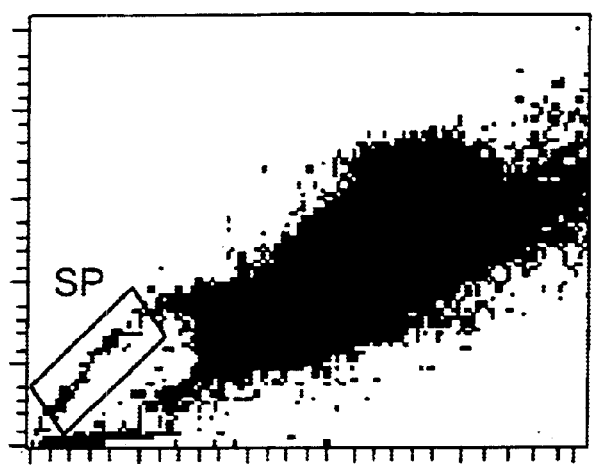
FIG. 22B  SP  FIG. 22C  Non-SP
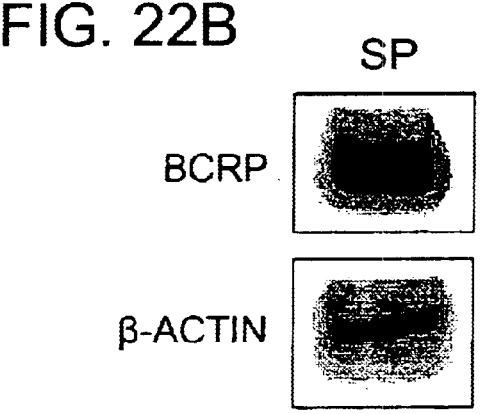
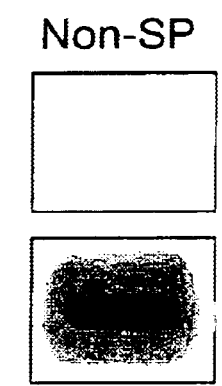
FIG. 22D
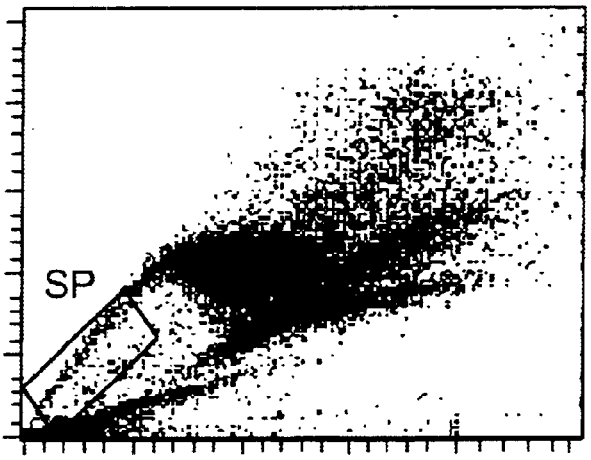
FIG. 22E
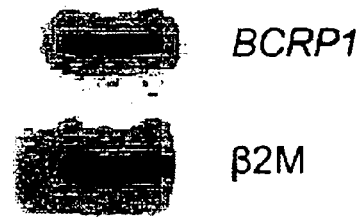

M5, (9;11)　　M1, (46XX)　　M1, (5;6)(7;13)　　M5, (46XX)
90% BLASTS　　83% BLASTS　　94% BLASTS　　91% BLASTS

RELATIONSHIP OF ABC TRANSPORT PROTEINS WITH HEMATOPOIETIC STEM CELLS AND METHODS OF USE THEREOF

CROSS-REFERENCE TO RELATED APPLICATIONS

The present Application is a Continuation-In-Part of co-pending International Application No. PCT/US99/11825 filed May 27, 1999, which claims the priority of provisional U.S. Ser. No. 60/086,988 filed May 28, 1998, the disclosures of which are hereby incorporated by reference in their entireties. Applicants claim the benefits of these Applications under 35 U.S.C. §§120 and 119(e).

RESEARCH SUPPORT

The research leading to the present invention was supported in part by the National Institutes of Health Grant No: PO1 53749-04. The government may have certain rights in the present invention. Support for this invention was also provided by the AMERICAN LEBANESE SYRIAN ASSOCIATED CHARITIES.

FIELD OF THE INVENTION

The present invention concerns methods of performing ex vivo expansion of gene-modified hematopoietic stem cells which are useful for many applications involving bone marrow transplantation and ex vivo gene therapy. The present invention also includes the gene-modified hematopoictic stem cells. The present invention further provides a method of isolating sten cells.

BACKGROUND OF THE INVENTION

Hematopoietic stem cells (HSCs) are primitive cells that generate all the formed elements of the blood and immune system. These cells are functionally defined based on their capacity for self-renewal divisions, which leads to the continuous generation of new HSCs over the lifetime of an animal, and by their potential for pluripotent hematopoietic differentiation. There are three possible general outcomes for the resulting daughter cells when a hematopoietic stem cell divides: (i) differentiation, (ii) self-renewal, or (iii) apoptosis. Despite the extensive study of HSCs, due to its relevance to bone marrow transplantation, gene therapy, and basic hematopoiesis, the mechanisms controlling these three tightly regulated outcomes are poorly understood.

Purification strategies for HSCs have been developed for both mouse [Spangrude et al., Science 241:58–62 (1988): (published erratum appears in Science 244(4908):1030 (1989)); Uchida et al., J.Exp.Med. 175:175–184 (1992)] and humnans HSCs [Zanjani et al., J.Clin.Invest. 93:1051–1055 (1994), see comments; Larochelle et al., Nat.Med. 2:1329–1337(1996); Civin et al., Blood 88:4102–4109 (1996)]. Most of these strategies use antibodies directed against various cell surface antigens and multiparameter cell sorting to isolate phenotypically defined cell populations. This approach has allowed isolation of murine stem cell populations of sufficiently high purity to allow reconstitution of irradiated recipients with less than 10 cells [Morrison et al., Proc.Natl.Acati.Sci.USA 92:10302–10306 (1995); Osawa et al., Science 273:242–245 (1996)], while considerably greater numbers of sorted human cells have been required to reconstitute xenogeneic recipients [Larochelle et al., Nat.Med. 2:1329–1337 (1996); Zanjani et al., Exp.Hematol. 26:353–360 (1998), see comments].

Hematopoietic stem cells also represent attractive targets for genetic modification since their progeny make up the entire spectrum of the hematopoietic system. Gene therapy involving stem cells is thus an expanding field that potentially has important applications in the treatment of a wide range of diseases [Nienhuis et al., Cancer, 67:2700 (1991)]. However, due to the inherent quiescent nature of stem cells, retroviral gene transfer is limited since stable integration requires cell division. Improved transduction of this target cell population is thus one of the major goals of current gene therapy research. In the mouse, gene transfer and repopulation with genetically-modified bone marrow stem cells following transplantation has been reported [Lemischka et al., Cell, 45:917 (1986) and Dick et al., Cell, 42:71 (1985)]. Whereas the level of stem cell gene transfer and expression are relatively modest, it has been sufficient to investigate effects of gene expression on hematopoiesis [Persons et al., Blood 90:1777 (1997)]. In humans, only an extremely low number of transgenic stem cells persist on a long-term basis [Brenner et al., Lancet, 342:1134 (1993) and Brenner, et al., Lancet, 341:85 (1993) and Rill et al., Blood, 84:380 (1994)]. Therefore there is a need for increasing the proportion of such transduced stem cells through ex vivo expansion following transduction and/or through in vivo selection approaches.

Most current protocols for transduction of stem cells employ in vitro liquid suspension culture with hematopoietic growth factors. It is now well established that culturing murine bone marrow cells for 4 days in the presence of defined concentrations of interleukin-3, interleukin-6, and stem cell factor does not adversely effect overall stem cell survival and function. However, expansion beyond this point has not proven to be beneficial and results in depletion of the reconstitution potential of the bone marrow graft. Cytokine-stimulated stem cells cultured in expansion conditions typically either undergo differentiation or programmed cell death (apoptosis). More mature populations such as the CFU-S and CFU-C, however, are capable of significant expansion in culture. However, these cells are distinct from stem cells and only provide short to moderate-term repopulating ability in transplanted mice. In humans, the long-term culture-initiating cell (LTC-IC) can be expanded in vitro with appropriate combinations and amounts of growth factors. LTC-ICs have recently been shown to be more mature than the SCID mouse repopulating cell (SRC) [Dick et al., Cell 42:71 (1985)]. SRCs are depleted in cultures that are more than 4 days old, which is consistent with the SRC being a more primitive cell type. More recently, culturing hematopoietic stem cells derived from the AGM (a pre-liver intraembryonic site) has been reported [Dzierzak et al. WO 98/12304, hereby incorporated by reference in its entirety]. However, the prior art teaches at most a four-fold expansion of human hematopoietic cells [Bhatia et al., J. Exp. Med., 186:619–624 (1997)].

The human MDR1 gene and its murine homologs were originally identified based on the ability of their expressed products, collectively referred to as P-glycoproteins (P-gps), to extrude a wide variety of cytotoxic drugs from the cell interior [Gros et al., Cell, 47:371–380 (1986) and Chen et al., Cell, 47:381–389 (1986)]. It is now known that the MDR1 gene belongs to a superfamily of transport proteins that contain a conserved ATP-binding cassette (ABC) which is necessary for pump function [Allikmets et al., Hum. Mol. Genet. 5:1649–1655 (1996)]. Numerous studies have clearly shown that P-gp expression plays an important role in the resistance of human tumor cells to cancer chemotherapy [Pastan and Gottesman, Annu. Rev. Med., 42:277–286 (1991)]. Considering that P-gps are also expressed in a wide variety of normal tissues, more recent studies have examined the normal physiologic functions of MDR1-like genes. Murine gene disruption experiments have demonstrated that expression of various P-gps is necessary for biliary excretion [Smit et al., *Cell,* 75:451–462 (1993)], maintenance of the blood-brain barrier [Schinkel et al., *Cell,* 77:491–502 (1994)], and elimination of drugs [Schinkel et al., *Proc.Natl.Acad.Sci. USA,* 94:4028–4033 (1997)]. P-gps can also mediate more general cellular functions including the translocation of lipids across the cell membrane [van Helvoort et al., *Cell,* 87:507–517 (1996)] and modulation of specific apoptosis pathways [Johnstone et al., *Blood,* 93:1075–1085 (1999) and Smyth et al., *Proc.Natl.Acad.Sci.USA,* 95:7024–7029 (1998)].

P-gp is expressed in a variety of hematopoietic cell types [Drach et al., *Blood,* 80:2729–2734 (1992)], including human CD34+ stem cells [Chaudhary and Roninson, *Cell,* 66:85–94 (1991)] and murine c-kit+ stem cells [Sorrentino et al., *Blood,* 86:491–501 (1995)]. Several lines of evidence suggest that P-gp expression is functionally conserved in hematopoietic stem cells.

Another ATP transport protein that contains a conserved ATP-binding cassette is the gene product of the Bcrp1/Mxr/Abcp gene (referred to as Bcrp and BCRP hereafter). The BCRP cDNA was originally cloned from several different human tumor cell lines that were resistant to multiple drugs including doxorubicin, topotecan, and mitoxantrone [Doyle et al., *Proc.Natl.Acd.Sci.USA* 95:15665–15670 (1998): (published erratum appears in *Proc Natl Acad Sci USA;* 96(5):2569 (1999)); Maliepaard et al., *Cancer Res.* 59:4559–4563 (1999); Miyake et al., *Cancer Res.* 59:8–13 (1999)]. A highly related mouse homologue (Bcrp1) was cloned from fibroblasts selected for multidrug resistance [Allen et al., *Cancer Res.* 59:4237–4241 (1999)]. In contrast to the structure of the MDR1 gene, which consists of two duplicated halves, the predicted structure of BCRP is that of a "half transporter", with a single ATP binding cassette and transmembrane region. The expression pattern of BCRP is highly restricted in normal human tissues, with the highest levels of mRNA detected in the placenta, and much lower levels detected in adult organs [Doyle et al., *Proc.Natl.Acad.Sci.USA* 95:15665–15670 (1998):(published erratum appears in *Proc.Natl.Acad.SciUSA.* 96(5):2569 (1999)); Allikmets et al., *CancerRes.* 58:5337–5339 (1998)].

Hematopoietic stem cells can be identified based on their ability to efflux fluorescent dyes that are substrates for P-gp, such as Rhodamine (Rho) 123 [Spangrude and Johnson, *Proc.Natl.Acad.Sci.SA,* 87:7433–7437 (1990); Fleming et al., *J. Cell Biol.,* 122:897–902 (1993); Orlic et al., *Blood,* 82:762–770 (1993); and Zijlmans et al., *Proc.Natl.Acad.Sci.USA,* 92:8901–8905 (1995)] and Hoechst 33342 [McAlister et al., *Blood,* 75:1240–1246 (1990); Wolf et al., *Exp. Hematol.,* 21:614–622 (1993); and Leemhuis et al., *Exp. Hematol.,* 24:1215–1224 (1996)]. One particular approach for purifying stem cells is based on Hoechst dye-staining of bone marrow cells to identify a minor fraction of side population (SP) cells that are highly enriched for repopulating activity [Goodell et al., *J. Exp. Med.,* 183:1797–1806 (1996)]. This SP phenotype identifies a primitive subset of stem cells present in multiple mammalian species [Goodell et al., *Nat. Med.,* 3:1337–1345 (1997)], and based on verapamil inhibition studies, may be due to expression of P-gp or another ABC transporter [Goodell et al., *J. Exp. Med.,* 183:1797–1806 (1996)].

Methodology for enriching pluripotent stem cells in culture could have a major impact on treatment of blood and immune-system disorders. For example, bone marrow transplantation is often the only option for persons having hematopoietic and immune-system dysfunctions caused by congenital disorders and or chemotherapy or radiation therapy. In addition, enriching pluripotent stem cells should greatly enhance the treatment of immunodeficency disorders. Furthermore, the effectiveness of the treatment of blood diseases by ex vivo gene therapy, e.g., treating sickle cell anemia or thalassemia, could also be substantially enhanced. Therefore, expansion of primitive stem cells in culture should be a major advance for all aspects of bone marrow transplantation as well as gene therapy applications. Unfortunately, despite the clear need for such methodology, heretofore, it has not been realized.

In addition, whereas a recent report demonstrates that sorting for expression of the vascular endothelial growth factor receptor can enrich human stem cells to near purity [Ziegler et al., *Science* 285:1553–1558 (1999)], there still remains a general need for better and more specific markers of human HSCs.

The citation of any reference herein should not be deemed as an admission that such reference is available as prior art to the instant invention.

SUMMARY OF THE INVENTION

The present invention provides a method of performing ex vivo expansion of a gene-modified hematopoietic stem cell. One embodiment of this type comprises transducing a hematopoietic stem cell with a nucleic acid encoding a transmembrane efflux pump (an ABC transporter) and then culturing the transduced cell, i.e., the gene-modified hematopoietic stem cell, ex vivo, thereby expanding the gene-modified hematopoietic stem cell. In a preferred embodiment, the gene-modified hematopoietic stem cell is expanded at least 10-fold.

As exemplified below, in one embodiment the transmembrane efflux pump can be human multidrug resistance-1 (i.e., MDR1, the P-glycoprotein) which is encoded by the nucleotide sequence of SEQ ID NO:1 and has the amino acid sequence of SEQ ID NO:2. In another embodiment the transmembrane efflux pump is murine MDR1 which is encoded by the nucleotide sequence of SEQ ID NO:5 and has the amino acid sequence of SEQ ID NO:6. In yet another embodiment the transmembrane efflux pump is murine MDR-3 which is encoded by the nucleotide sequence of SEQ ID NO:7 and has an amino acid sequence of SEQ ID NO:8. In still another embodiment the transmembrane efflux pump is the human Bcrp1/Mxr/Abcp gene product (BCRP) which is encoded by the nucleotide sequence of SEQ ID NO:9 and has the amino acid sequence of SEQ ID NO:10. In yet another embodiment the transmembrane efflux pump is a murine BCRP which is encoded by the nucleotide sequence of SEQ ID NO: 13 and has the amino acid sequence of SEQ ID NO: 14. In still another embodiment the transmembrane efflux pump is a murine BCRP which is encoded by a nucleotide sequence comprising SEQ ID NO:11 and has an amino acid sequence comprising SEQ ID NO:12.

In a particular embodiment inhibitors of P-glycoprotein, such as PSC833, are added to the expansion culture. In yet another embodiment the transmembrane efflux pump is MRP (multidrug resistant protein). In still another embodiment, the transmembrane efflux pump is the cystic fibrosis membrane transporter.

In one embodiment, the method comprises culturing the gene-modified hematopoietic cell in the presence of one or more cytokines. In one such embodiment the culture contains 5 to 300 ng/ml of the cytokine. In a particular embodiment the culture contains 10 to 50 ng/ml of the cytokine. In another embodiment the culture contains 0.5 to 10 ng/ml of the cytokine.

In one embodiment the cytokine is an early-acting hematopoietic cytokine. In a particular embodiment the cytokine is interleukin-3. In another embodiment the cytokine is interleukin-6. In still another embodiment the cytokine is stem cell factor. In still another embodiment the cytokine is G-CSF. In yet another embodiment the cytokine is GM-CSF. In still another embodiment the cytokine is the FLT-3 ligand. In yet another embodiment the cytokine is interleukin-1. In still another embodiment more than one of these cytokines are present. In a particular embodiment interleukin-3, interleukin-6, and stem cell factor are all present.

In another embodiment of the method of performing ex vivo expansion of a gene-modified hematopoietic stem cell, the cell is expanded for at least 3 days. In alternative embodiment the gene-modified hematopoietic stem cell is expanded for at least 6 days. In a particular embodiment the gene-modified hematopoietic stem cell is expanded for at least 9 days. In a preferred embodiment the gene-modified hematopoietic stem cell is expanded for at least 12 days. In a related embodiment the gene-modified hematopoietic stem cell further comprises a second heterologous gene.

In still another embodiment of the method of performing ex vivo expansion of a gene-modified hematopoietic stem cell the hematopoietic stem cell is a mammalian hematopoietic stem cell. In a particular embodiment the mammalian hematopoietic stem cell is a murine hematopoietic stem cell. In a preferred embodiment the mammalian hematopoietic stem cell is a human hematopoietic stem cell. In another preferred embodiment the gene-modified hematopoietic stem cell expresses a splice-corrected version of the human MDR1, as exemplified below.

A particular method of the present invention comprises transducing the hematopoietic stem cell with a viral vector that comprises a nucleic acid encoding a transmembrane efflux pump. In one such embodiment the transmembrane efflux pump is MDR1. In another embodiment the transmembrane efflux pump is BCRP. In a particular embodiment the viral vector is a herpes simplex viral vector. In another embodiment the viral vector is an adenoviral vector. In still another embodiment the viral vector is an adeno-associated viral vector (AAV). In a preferred embodiment the viral vector is a defective virus, more preferably not encoding a gene for a functional viral protein.

In an alternative embodiment of the method, the viral vector is a retroviral vector. In one such embodiment the retroviral vector is an HIV retroviral vector. In another embodiment the vector is a VL 30 vector. In yet another embodiment the vector is a MSCV retroviral vector. As exemplified below the retroviral vector can be a Harvey Murine Sarcoma Vector. In one such embodiment the hematopoietic stem cell is transduced by being co-cultured with a retroviral producer cell line. In still another embodiment of the method, transducing the hematopoietic stem cell with a transmembrane efflux pump, e.g., MDR1 or BCRP, is performed with a DNA vector (i.e., a naked DNA) that comprises a nucleic acid encoding the transmembrane efflux pump.

In a particular embodiment the nucleic acid encoding a transmembrane efflux pump, e.g., MDR1 or BCRP, is introduced into the hematopoietic stem cell with a non-integrating vector e.g., an adenoviral vector. Such an adenoviral vector would only be expressed transiently, during the period of in vitro expansion. This contrasts with the retroviral vector exemplified below which is integrated and expressed continuously in vivo. In another embodiment, the nucleic acid encoding MDR1 or BCRP, for example, is introduced into the hematopoietic stem cell with Murine Stem Cell Virus which lacks the VL30 sequences in the Harvey Murine Sarcoma vector [Hawky et al., *Gene Therapy* 1:136 (1994)].

The present invention further provides a gene-modified hematopoietic stem cell that has been transduced with a nucleic acid encoding a transmembrane efflux pump, e.g. MDR1 or BCRP, and has been expanded. In one embodiment the hematopoietic stem cell is a mammalian hematopoietic stem cell. In a particular embodiment the hematopoietic stem cell is a murine hematopoietic stem cell. In a preferred embodiment the mammalian hematopoietic stem cell is a human hematopoietic stem cell. In another preferred embodiment the gene-modified hematopoietic stem cell expresses a splice-corrected version of the human MDR1 as exemplified below.

In one embodiment the gene-modified hematopoietic stem cell has been expanded for at least 3 days. In another embodiment the gene-modified hematopoietic stem cell has been expanded for at least 6 days. In a particular embodiment the gene-modified hematopoietic stem cell has been expanded for at least 9 days. In a preferred embodiment the gene-modified hematopoietic stem cell of has been expanded for at least 12 days. In a particular embodiment of this type the gene-modified hematopoietic stem cell has been expanded for 16 days or more. In a related embodiment the gene-modified hematopoietic stem cell further comprises a second heterologous gene.

Methods of engrafting an animal with the gene-modified hematopoietic stem cell of the present invention are also provided. Preferably. the gene-modified hematopoietic stem cell has been expanded as taught herein. One embodiment comprises placing the expanded gene-modified hematopoietic stem cell into an animal. In one such method, placing the cell into the animal is performed by injection. In a particular embodiment more than one injection is made. In another embodiment multiple injections are made over the course of several days (e.g. in humans 1 to 20 days appears to be a reasonable range). In one embodiment the animal is a mammal. In a particular embodiment the mammal is a mouse. In a preferred embodiment the mammal is a human. Preferably the engrafted cell is stable for at least three months, and more preferably six months, or a year or even longer.

The present invention further provides methods of treating an animal in need of treatment for a hematopoietic stem cell deficiency using a method of engrafting of the present invention. In one embodiment of this method the hematopoietic stem cell is transduced ex vivo with a nucleic acid encoding a transmembrane efflux pump, e.g. MDR1 or BCRP. The transduced hematopoietic stem cell (a gene-modified hematopoietic stem cell) is expanded and then engrafted into the animal. In a preferred embodiment, the hematopoietic stem cell is obtained from the animal in need of treatment, and then after being transduced with a nucleic acid encoding MDR1 or BCRP and expanded, the resulting gene-modified hematopoietic stem cell is placed back into the animal. In a particular embodiment the animal is a mammal. In a preferred embodiment of this type, the mammal is a human.

A gene-modified hematopoietic stem cell used in a method of engrafting an animal of the present invention can further comprise a second heterologous gene. Such methods include ex vivo gene therapy which may be used to treat diseases involving a dysfunctional cell that is derived from an hematopoietic stem cell. Thus, any genetic defect that could be corrected by bone marrow transplantation can be treated by the methods described herein. In one such embodiment, the second heterologous gene encodes a functional β-globin. In another embodiment, the second heterologous gene encodes a functional adenosine deaminase. In still another embodiment, the second heterologous gene encodes a functional glucocerebrosidase.

The present invention further provides the use of the expression of a transmembrane efflux pump, as a means to purify stem cells. Indeed, the present invention discloses that BCRP expression is a specific marker for stem cells e.g., hematopoietic stem cells, and side population (SP) stem cells from other organs. The present invention therefore provides methods for isolating primitive stem cells based on the detection of BCRP expression, which as disclosed herein, is a functional determinant for the SP cell phenotype.

Therefore, the present invention provides methods of identifying stem cells. One such embodiment comprises obtaining a cell sample which contains (or is suspected to contain) stem cells and detecting the expression of BCRP in the cell sample. A cell is is identified as a stem cell if BCRP is expressed by the cell. The detection of the expression of BCRP can be performed via its specific pumping activity. Preferably the detecting of the expression of BCRP is performed with an anti-BCRP antibody which binds to BCRP (more preferably the extracellular portion of BCRP). Stem cells are identified due to their binding to the anti-BCRP antibody. The cell sample can be obtained from any animal, but preferably a mammal and more preferably a human.

The identification and isolation of stem cells via the methods of the present invention extend beyond hematopoietic stem cells and comprises all stem cells, including muscle stem cells, and even brain stem cells. The present invention also provides methods of using these isolated stem cells including the use of muscle stem cells in the treatment of diseases such as muscular dystrophy, and Parkinson's Disease. In addition, the hematopoietic stem cells can be used in bone marrow transplants (e.g., for treatment of leukemia) as well as for ex vivo gene therapy for treatment of blood diseases such as sickle cell anemia and thalassemia.

The present invention therefore also provides methods of isolating stem cells. One such embodiment comprises obtaining a cell sample which contains (or is suspected to contain) stem cells and contacting them with an antibody that binds to BCRP (preferably an extracellular portion BCRP). Cells that bind to the antibody are then isolated. These isolated cells are identified as isolated stem cell due to their binding to the anti-BCRP antibody. The cell sample can be obtained from any animal, but preferably a mammal and more preferably a human. In a preferred embodiment of the present invention the isolation of the stem cells is performed by flow cytometry. In particular embodiment, the antibody has a fluorescent label and the isolation of the stem cells is performed by fluorescent-activated cell sorting (FACS).

In another embodiment, the anti-BCRP antibody is placed on a solid support. The solid support can then be contacted/incubated with a sample of cells, such that the cells can associate with the solid support by binding to the anti-BCRP antibody. The solid support is then washed to remove cells that bind non-specifically. The remaining cells are eluted from the solid support (by an excess of free antibody, for example). Based on their ability to bind anti-BCRP antibody with specificity, the eluted cells are identified as isolated stem cells. In a particular embodiment, the solid support is an immunomagnetic bead (e.g., MILTENYI MINIMACS™, DYNABEADS™). The anti-BCRP antibody is placed on the immunomagnetic beads which are then contacted/incubated with a sample of cells, as indicated above, such that the cells can associate with the beads by binding to the anti-BCRP antibody. Preferably after an appropriate incubation period, the immunomagnetic beads can then be separated from the sample of cells with a magnet. The immunomagnetic beads are then washed to remove cells that bind non-specifically. The remaining cells are eluted from the immunomagnetic beads as indicated above. Again, based on their ability to bind anti-BCRP antibody, the isolated cells are identified as stem cells.

The present invention also provides a method of diagnosing and/or prognosing human acute myelogenous leukemia (AML) through assaying BCRP expression in leukemic cells, e.g., blast cells from individuals having or suspected of having AML. Such diagnosis can be used to tailor a therapeutic regimen so as to contain drugs that are not susceptible to the counter-effects of the BCRP (such as being pumped out of the cell by this transmembrane efflux pump). In addition, the detection of the expression of BCRP in cells from a bone marrow sample or a blood sample can lead to the early diagnosis and/or prognosis of AML. Such early diagnosis and/or prognosis could lead to particular treatments such as an earlier bone marrow transplantation. The detection of BCRP expression in the cells can be performed with an anti-BCRP antibody using flow cytometry and/or immunocytochemistry.

Therefore, the present invention provides methods of diagnosing AML in a human subject. A particular embodiment of this type comprises obtaining a leukemic cell from the subject and then determining whether BCRP is overexpressed in the leukemic cell. When BCRP is determined to be overexpressed in the leukemic cell, the patient is diagnosed as having AML. In a preferred embodiment the leukemic cell is a blast cell.

Accordingly, it is a principal object of the present invention to provide a method of expanding hematopoietic stem cells ex vivo.

It is a further object of the present invention to provide an expanded hematopoietic stem cell.

It is a further object of the present invention to provide a method for reconstituting bone marrow cells in an animal subject after the animal has undergone chemotherapy or radiation therapy.

It is a further object of the present invention to provide a method for providing bone marrow cells for a human subject while the human is undergoing chemotherapy.

It is a further object of the present invention to provide a method of engrafting a gene-modified hematopoietic stem cell into an animal subject.

It is a further object of the present invention to provide a method of performing ex vivo gene therapy on an animal subject by engrafting an expanded gene-modified hematopoietic stem cell into the animal subject wherein the gene-modified hematopoietic stem cell further comprises a therapeutic gene.

It is a further object of the present invention to provide a method of obtaining purified stem cells.

It is a further object of the present invention to provide the purified stem cells.

It is a further object of the present invention to provide methods of using the purified stem cells in the treatment of diseases in which one or more specific cell tapes are being adversely depleted and/or become dysfunctional.

It is a further object of the present invention to provide methods of using the purified stem cells for gene therapy.

It is a further object of the present invention to use BCRP as a marker for diagnosing dysfunctional cells in humans.

It is a further object of the present invention to use BCRP as a marker for prognosing the progression of AML.

These and other aspects of the present invention will be better appreciated by reference to the following drawings and Detailed Description.

BRIEF DESCRIPTION OF THE DRAWINGS

FIGS. 1A–1B show the expansion kinetics for total cells (FIG. 1A) and drug-resistant progenitors (FIG. 1B) following retroviral transduction. Cells were maintained in liquid suspension cultures with addition of murine IL-3, human IL-6, and rat SCF. FIG. 1A shows a typical cell expansion for cells from either MDR1 or DHFR co-cultures. No significant difference in cell expansion was noted between these groups. Cells were removed at 6 day intervals and assayed for clonogenic progenitors in methylcellulose. Selective concentrations of taxol or trimetrexate were used to determine MDR1 or DHFR expressing progenitor cells respectively. FIG. 1B shows the drug-resistant progenitor population was found to expand extensively and typically reached 100-fold by 2 weeks.

FIGS. 3A–3C show representative hemoglobin electrophoresis gels from non-irradiated mice engrafted with expanded bone marrow (5 months post-BMT for MDR 20 and 7 months post-BMT for all others). C57 bone marrow was used as the donor marrow for transduction and expansion. Recipient mice were HW80. The differing hemoglobin patterns are indicated in FIG. 3A. Primary recipients shown in FIG. 3B are MDR 7, 11, 18, 20 from expt. #1 and MDR 15 from expt. #2. Secondary irradiated recipients were transplanted with marrow cells from MDR 20 demonstrating persistence of donor engraftment following secondary transplant, (a formal proof of stem cell engraftment) as shown in FIG. 3C.

FIG. 4 shows the competitive repopulation assay to determine the relative stem cell content of ex vivo expanded bone marrow versus fresh non-expanded marrow. C57 donor bone marrow cells were transduced with HaMDR1. HW80 donor bone marrow cells were transduced with HaDHFR. Cells were expanded for 12 days in culture then combined according to hind limb volume. 0.005 vols. expanded cells were competed against 0.25 vols. of fresh competing marrow. MDR1 expanded cells effectively competed against fresh HW80 marrow (FIG. 4A, left). DHFR-expanded marrow was completely out competed by fresh C57 marrow (FIG. 4A, middle). When MDR1 (C57) was competed against DHFR (HW80) at equal vols. mice reconstituted solely with MDR1 marrow, indicating a much greater stem cell content (FIG. 4A, right). The comparison of the bands for the distinctive Hb patterns of C57 and HW80 are shown in FIG. 4B. FIG. 4C shows the Hb patterns in recipient mice (lanes 1–10) as analyzed by Hb electrophoresis.

FIG. 5 shows the secondary CFU-S analysis for HaMDR1 marked primitive hematopoietic cells. At time points from 10 to 24 weeks post-tran splant, primary recipients from MDR vs. DHFR competitive repopulation mice (n=6) and MDR 15 were sacrificed and bone marrow cells were injected into secondary recipients. Day 12 CFU-S were harvested and DNA was prepared for Southern blot analysis. DNA was restricted with EcoR1 and probed with an MDR1 specific probe. A band of the correct size was seen in all CFU-S examined (88/88) from 7 individual mice. 56 representative examples are shown. Negative controls included CFU-S from mice transplanted with untransduced bone marrow. All 10 of these (4 shown) did not contain HaMDR1 retroviral DNA.

FIG. 6B shows Southern blot analysis of hemoglobin DNA for multilineage engraftment. DNA was prepared from the peripheral blood of mice #20, 21, and 26. DNA was restricted with EcoRI and probed with a hemoglobin-specific probe. The appropriate bands are indicated by an arrow for both C57 (single) and HW80 (diffuse). The level of lympho-myeloid engraftment determined by DNA analysis correlates very well with the level of engraftment determined in the erythroid lineage by hemoglobin electrophoresis.

FIG. 7A shows the kinetics of white blood cell elevation in mice engrafted with expanded bone marrow. The WBC count for all 10 engrafted mice from FIGS. 6A–6B are shown as they were examined serially. Mice typically had a long latent period of above normal to normal WBC counts followed by a rapid phase observed from 5 to 8 months later. Two mice from this experiment maintain long-term engraftment and continue to have normal WBC counts at time points 8.5 months post-transplant.

FIG. 7B–1 to 7B–6 show Wright-stained peripheral blood smears from mice displaying an abnormal cell population. A normal mouse smear at the indicated magnifications is shown (top). The second example demonstrates the most common morphology seen (middle). In a few rare cases, the third blast-like phenotype was seen indicating probable transformation from a myeloproliferative disorder into a leukemia (bottom).

FIGS. 9A–9B show the limiting dilution transplant analysis of MDR1-transduced SP cells isolated from 12 day expansion cultures. HaMDR1-transduced BM cells (C57BL/6 background) were placed into liquid suspension culture and expanded for 12 days. On day 12, the SP cell fraction was isolated by flow cytometry using the sorting gate shown in FIG. 9A. The sorted cells were then injected into lethally irradiated recipient mice at the indicated doses, along with a 2×10$^5$ fresh BM cells (HW80 background). FIG. 9A depicts the results 16 weeks following transplant, peripheral blood leukocyte DNA was prepared and analyzed by PCR for the presence of the HaMDR1 proviral genome. A water-only control and a non-transplanted mouse control (HW80) are shown on the left as negative controls. Transplanted mice received cell doses ranging from 250 to 9400 cells as indicated above the lanes. The numbers 1–18 correspond to individual recipient mice. FIG. 9B depicts the results when the reconstitution was also measured using hemoglobin electrophoresis. Erythroid cells derived from the sorted SP cells are identified by the faster migrating, C57BL/6-derived hemoglobin isoform. The animal numbers are the same as in panel A, and samples from untransplanted C57BL/6 and HW80 mice are shown on the right. The asterisks indicate samples where there were detectable amounts of C57BL/6-derived hemoglobin.

FIGS. 14A and 14B show SP cell analyses performed after 7 days of expansion. FIGS. 14C and 14D show a second independent experiment analyzed after 13 days of culture. The percentage of cells in the SP cell gate is indicated in each panel. In experiment 2, propidium iodide was added before flow cytometry analysis to exclude dead cells from the initial gated population.

FIG. 15A shows the hemoglobin electrophoresis of 12-day expanded cells competed against fresh bone marrow cells. C57BL/6 cells were transduced with either the HaMDR1 vector (left lanes), or with the HaMDR1Δ34 vector (right lanes), and competed against fresh HW80 bone marrow cells at a femur volume ratio of 0.02 transduced to 0.25 fresh. Sixteen weeks after transplant into irradiated recipient mice, hemoglobin electrophoresis was performed to monitor engraftment from the two donor sources. Each lane represents the results from an individual transplanted mouse. FIG. 15B shows the PCR analysis of DNA from peripheral leukocytes of mice transplanted with equal volumes of HaMDR1 and HaMDR1Δ34-transduced marrow. The single primer set was used that flanked the "Δ34" deletion, and amplified a 692 bp and 590 bp fragment from the HaMDR1 and the HaMDR1Δ34 proviral genomes respectively. From the left, the first lane is from a mock transduced mouse, the second lane from a mouse that received only HaMDR1Δ34-transduced cells, and the third lane from a mouse that received only HaMDR1-transduced cells. All the rest of the lanes are from 2 independent experiments where mice were transplanted using 0.02 femur volumes from each expanded graft. The three mice in the first experiment were analyzed 11 weeks after transplant, and the last 6 lanes are from mice from a second experiment analyzed 18 weeks after transplant.

FIGS. 16A–16B show the efflux of Rho 123 in peripheral blood leukocytes from wild type (FIG. 16A) and knockout mice (FIG. 16B). FIGS. 16C–16D depict the SP cell analyses of bone marrow cells from wild type (FIG. 16C) and knockout mice (FIG. 16D). The arrows show the SP cell fraction in each case.

FIGS. 22A–22E depict Bcrp1 expression in Rhesus monkey bone marrow SP cells and in muscle-derived SP cells. FIGS. 22A–22C show an SP analysis f Rhesus bone marrow cells with the sorting gates used for the SP (R2) and non-SP cells (R3). RNA was amplified by RT-PCR from 2000 sorted SP cells and 10,000 non-SP cells at the indicated number of cycles using β-actin or BCRP primers, as indicated. Roughly equivalent points on the β-actin amplification curve are shown for both samples. FIGS. 22D–22E show murine skeletal muscle cells which were stained with Hoechst dye and SP cells that were isolated by sorting. RNA was prepared from the sorted SP cells, and analyzed for expression of Brcp1 and β2 microglobulin by RT-PCR.

DETAILED DESCRIPTION OF THE INVENTION

Figure 2A:
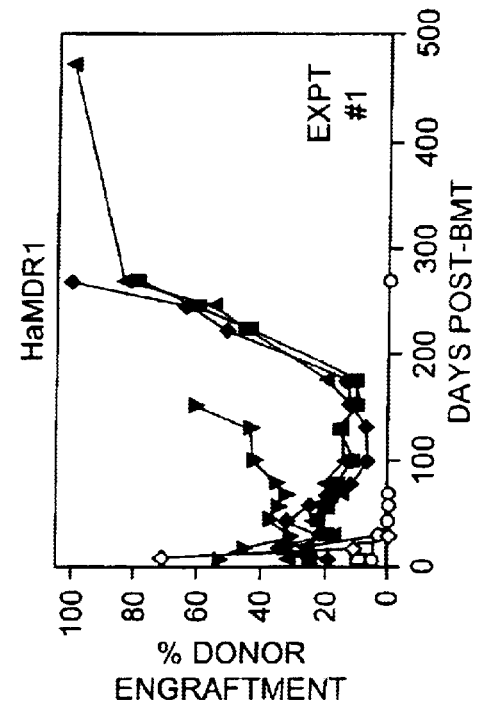
FIGS. 2A–2D show the long-term analysis of engraftment with donor bone marrow in non-irradiated recipients. HW80 recipient mice were injected for 5 consecutive days with transduced bone marrow cells (C57) which had been expanded in culture for 12 to 16 days. Later the same day, mice were treated with trimetrexate (130 mg/kg) and NBMPR-P (20 mg/kg). Beginning at 1 week post-transplant, donor C57 hemoglobin levels were quantitated by electrophoresis on cellulose acetate gels. Persistent engraftment was only seen in mice receiving expanded bone marrow cells transduced with HaMDR1 (5/12) as shown in FIG. 2B. Engrafted mice included: MDR 7 (■), MDR 11 (▲), MDR 18 (♦), MDR 20 (▼) and from the second experiment MDR 15 (●). No stable engraftment was seen in mock-transduced (0/8) or DHFR-transduced (0/8) expanded bone marrow as shown in FIG. 2A. Shown in FIGS. 2A–2B are mice from 2 independent expansion experiments.
Figure 2C:
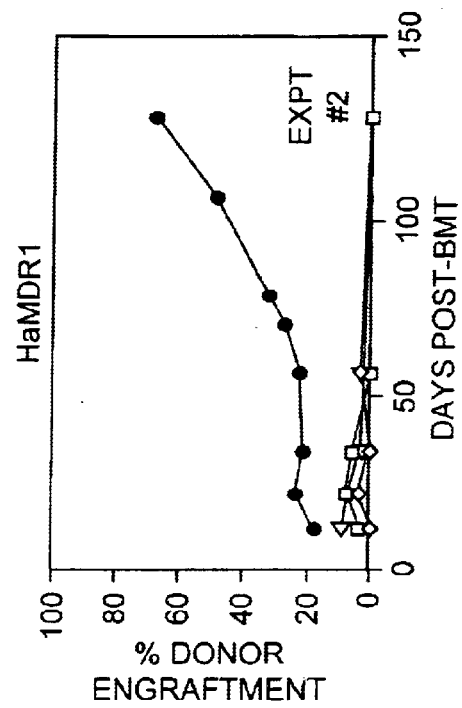

The present invention provides methods of performing ex vivo expansion of gene-modified hematopoietic stem cells which are useful for many applications including bone marrow transplantation, and ex vivo gene therapy. In addition, the present invention provides methods of engrafting the gene-modified hematopoietic stem cells of the present invention into animals, including for bone marrow transplantation and ex vivo gene therapy. Therefore the present invention provides methods of treating an animal in need of treatment for a hematopoietic stem cell deficiency using a method of engrafting the expanded gene modified hematopoietic stem cells of the present invention. In one such embodiment the hematopoietic stem cell is transduced ex vivo with a nucleic acid encoding a transmembrane efflux pump, e.g. MDR1. The transduced hematopoietic stem cell (i.e., a gene-modified hematopoietic stem cell) is expanded and then engrafted into the animal. Preferably the hematopoietic stem cell used is matched with the recipient animal to minimize and/or prevent host rejection. Thus, the hematopoietic stem cell is preferably obtained from the animal in need of treatment, and then after being transduced with a nucleic acid encoding MDR1 and expanded, the resulting gene-modified hematopoietic stem cell is placed back into the animal. The treatments as described herein may be used for any hematopoietic stem cell deficiency including that due to radiation therapy and/or chemotherapy, e.g., as used in cancer treatments. One particular advantage for treating a hematopoietic stem cell deficiency due to chemotherapy with a method of the present invention is that a gene-modified hematopoietic stem cell transduced with a nucleic acid encoding MDR1 will also be protected from the chemotherapeutic and its adverse effects. Therefore, the engrafting of the gene-modified hematopoietic stem cell into the recipient animal can be perfomied concomitantly with the chemotherapy.

The ex vivo gene therapy methodology of the present invention can be used for treating any disorder (particularly a genetic disorder) that involves a defect in a cell derived from a hematopoietic stem cell including but not limited to the treatment of thalassemia (e.g., with an expanded modified hematopoietic stem cell encoding human β-globin), Gaucher's disease (e.g., with an expanded modified hematopoietic stem cell encoding glucocerebrosidase), sickle cell anemia, and leukemia.

The present invention further provides the expanded gene-modified hematopoietic stem cells used and/or produced by such methods. Such expanded gene-modified hematopoietic stem cells can also contain a second heterologous gene.

In addition, the ability of expanding the otherwise rare hematopoietic stem cells provided by the present invention provides a source of hematopoietic stem cells which is large enough in quantity to allow standard biochemical analysis to be performed on this relatively unstudied cell type. Indeed, the present invention results in the capability of the expanding of human hematopoietic stem cells that is greatly increased from the maximum of about four-fold expansion taught in the prior art. Thus, the present invention provides a means for performing facile assays for identifying factors involved in the regulation of the proliferation versus differentiation of hematopoietic stem cells, particularly human hematopoietic stem cells. Such assays, for example, can be based on the experimental conditions taught herein and the administration of fractionated cellular extracts. Naturally occurring factors can be identified by such assays and then isolated by convention biochemical procedures. Alternatively, chemical libraries and or phage libraries can be used in an analogous drug screening assays. These naturally occurring factors and drugs can then be used to manipulate the fate of hematopoietic stem cells initially in vitro and eventually in vivo. Indeed, currently there are no known factors which specifically lead to the proliferation of hematopoietic stem cells in the absence of differentiation.

In Example 1, below, bone marrow cells were transduced with a Harvey (Ha)/MDR1 retrovirus and expanded for 12 days in the presence of interleukin (IL)-3, IL-6, and stem cell factor (SCF). Long-term engraftment in non-irradiated mice was observed after transplantation of the cells which were transduced with Ha/MDR1. To compare relative repopulating activities of expanded vs. unexpanded cells, competitive repopulation experiments in irradiated recipients were performed. These results showed at least a 10-fold increase in the absolute number of repopulating cells relative to fresh untransduced marrow. The results demonstrate that MDR1 overexpression allows dramatic cytokine-driven expansion of hematopoietic stem cells in vitro.

In Example 2 it is shown that MDR1-mediated stem cell expansion is associated with an increase in "side population" (SP) stem cells, defined by Hoechst dye staining. Transduction of murine bone marrow cells with an MDR1 retroviral vector resulted in an almost 2 log increase in SP cell numbers over 12 days in culture, while there was a rapid loss of SP cells from control cultures. Stem cell amplification was not limited to ex vivo expansion cultures, but was also evident when MDR1-transduced cells were directly transplanted into irradiated mice. In these cases, stem cell expansion was associated with relatively high vector copy numbers in stem cell clones. As previously indicated herein, some cases were associated with a characteristic myeloproliferative syndrome. A functionally inactive MDR1 mutant cDNA was used to show that P-gp pump function was required both for amplification of phenotypically-defined SP cells, and functionally-defined repopulating cells. These results further support the concept that ABC transporter function can have important effects on hematopoietic stem cell development.

The universal presence of transporter activity and expression in hematopoietic stem cell, and the generally observed down regulation of transporter expression that occurs with differentiation, can he explained by a functional role for ABC transporters in promoting self-renewal outcomes. Based on Example 1 below, showing that enforced MDR1 expression causes stem cell expansion in a variety of settings, and recently published studies showing that MDR1 expression can inhibit apoptosis in hematopoietic cell lines [Johnstone et al., *Blood* 93:1075–1085 (1999)], MDR1 expression appears to promote stem cell self-renewal by causing a relative block to apoptosis during stem cell division. This function could reflect the normal role for endogenous transporter expression in stem cells, as well as indicate a role for dysregulated transporter expression in leukemogenesis. Interestingly, the present invention discloses that the MDR1 genie is not necessary for dye efflux in HSCs, or for the SP phenotype.

As shown herein, the Bcrp gene is expressed at relatively high levels both in primitive CD34-murine HSCs and in SP cells from the bone marrow. In contrast, the expression of other known ABC transporters in the highly enriched CD34- stem cell population is low to absent. A retroviral vector expressing the human BCRP cDNA has been constructed as described below to study the functional properties of BCRP. Fibroblasts expressing this vector gain the capacity to efflux Hoechst dye, a prerequisite property for establishment of the SP phenotype. Furthermore, when primary bone marrow cells are transduced with the BCRP vector, there is a large expansion of SP cells over time in culture. SP cells from the muscle also express Bcrp at high levels. Indeed, BCRP mRNA expression is highly restricted in normal tissues, and cannot be detected in adult tissues at the Northern blot level. Furthermore, as disclosed herein, Bcrp expression is relatively restricted to the hematopoietic stem cell compartment in mice. These data indicate that Bcrp expression may be a universal marker for stem cells from various organs, and may be the critical molecule for conferring the dye efflux phenotype to stem cells. Therefore, the present invention provides a method of identifying stem cells by their expression of BCRP. Such identification can then be used to isolate the stem cells.

In addition, both MDR1 and BCRP appear to be able to promote stem cell amplification and self-renewal by decreasing the probability of apoptosis as an outcome of stem cell division. HSCs therefore, appear to require expression of at least one of these transporters to sustain normal hematipoiesis time.

Since tightly regulated expression of ABC transporters appears to be required for normal hematopoiesis, it follows that dysregulated expression could lead to hematopoietic abnormalities, or even contribute to leukemogenesis. Such effects in mice transplanted with MDR1 vectors are demonstrated below, in an experimental setting where expression of P-gp is abnormally increased in primitive cells and proper developmental regulation of P-gp is over-ridden. Indeed, when the expression of P-gp was abnormally increased, a significant proportion of transplanted mice developed a myeloproliferative syndrome characterized by peripheral blood leukocytosis, an increase in immature myeloid forms in the circulation, and significant degrees of splenomegaly (see Example 1 below). This syndrome developed slowly, with the first cases being noted two to three months after transplant, and with the incidence increasing to about 50% by six to nine months. The delayed pattern observed is consistent with the acquisition of a second genetic lesion that is required for development of the syndrome. This second lesion seems to be related to the prior degree of stem cell expansion conferred by the MDR1 vector because mice transplanted with ex vivo expanded cells showed a higher incidence of myeloproliferation than mice transplanted with freshly transduced, unexpanded cells (Example 2 below).

Furthernore, early myeloproliferation is associated with a relatively high vector copy number in transduced stem cell clones (see Example 2 below), indicating that development of the syndrome may be dependent on a high threshold level of expression of the transferred MDR1 gene. Altogether, these data show that dysregulated MDR1 expression can contribute to leukemogenesis, and they also indicate that dysregulated expression of other ABC transporters may also lead to disordered hematopoiesis.

In addition, expression of other uncharacterized ABC transporters occurs in acute myelogenous leukemia (AML) with significant frequency. For example, dysregulated BCRP expression is likely to be involved in at least some of these cases, based on its known capacity for dye efflux, and its tightly regulated expression pattern during normal myeloid development (see Example 3). Furthermore, given the capacity of BCRP to confer resistance to anthracycline drugs [Miyake et al., *Cancer Res.* 59:8–13 (1999)], BCRP expression may directly confer resistance to AML induction chemotherapy. Indeed, BCRP expression in AML blasts appears to be associated with a drug resistant phenotype and thereby predict a poor prognosis. Therefore, the present invention also provides a method of diagnosing/prognostigating pediatric patients with AML, e.g., by examining/monitoring blast cells from such pediatric patients.

Therefore, if appearing herein, the following terms shall have the definitions set out below.

A "hematopoietic stem cell" is a pluripotent cell that is able to either replicate itself with self-renewal divisions or to differentiate along a number of pathways and thereby generate erythrocytes, granulocytes, monocytes, mast cells, lymphocytes, and megakaryocytes. These stem cells occur with a frequency of about 1 stem cell per $10^4$ bone marrow cells.

A "heterologous gene" as used herein is a gene that is introduced into a stem cell (e.g., a hematopoietic stem cell) through a molecular biological manipulation. As defined herein, this molecular biological manipulation is made such that the heterologous gene is inserted into the stem cell. The heterologous gene need not be expressed in the stem cell as long as it is expressed in the progeny of the stem cell. The coding sequence of the heterologous gene is operatively linked to an expression control sequence. Generally a heterologous gene is first placed into a vector. The heterologous gene is not necessarily naturally contained by the vector, though a heterologous gene can encode a protein that is native to the stem cell. For example, the heterologous gene can encode a functional protein and be used in ex vivo gene therapy to replace the corresponding defective gene in a stem cell, e.g., an hematopoietic stem cell. The heterologous gene will usually be flanked by DNA that does not flank the genomic DNA in the genome of the source organism. Alternatively, the heterologous gene may not be naturally found in the stem cell, such as the gene for human MDR1 introduced into a murine hematopoietic stem cell.

A cell has been "transduced" by a heterologous gene such as the MDR1 gene (i.e. a nucleic acid encoding MDR1), when the gene has been introduced inside the cell and the coding sequence of the gene is operatively linked to an expression control sequence. The transducing gene is carried by a vector and the gene may or may not be integrated (covalently linked) into chromiosional DNA making up the genome of the cell. A stably transduced cell is one in which the transducing gene has become integrated into a chromosome so that it is inherited by daughter cells through chromosome replication. This stability is demonstrated by the ability of the cell to establish cell lines or clones comprised of a population of daughter cells containing the transducing gene. A "clone" is a population of cells derived from a single cell or common ancestor by mitosis. A "cell line" is a clone of a primary cell that is capable of stable growth in vitro for many generations.

As used herein a "gene-modified hematopoietic stem cell" is a hematopoietic stem cell that has been transduced by a heterologous gene. A gene-modified hematopoietic stem cell transduced with a nucleic acid encoding MDR1 (the mdr1 gene) is exemplified below.

As used herein the "expansion" of an hematopoietic stem cell indicates that there is an increase in the absolute number of hematopoietic stem cells, i.e., during the culturing of the cells. Analogously, an hematopoietic cell that has undergone such expansion has been "expanded".

As used herein "engrafting" a stem cell, preferably an expanded hematopoietic stem cell, means placing the stem cell into an animal, e.g., by injection, wherein the stem cell persists in vivo. This can be readily measured by the ability of the hematopoietic stem cell, for example, to contribute to the ongoing blood formation.

As used herein an "ABC transporter" is used in the conventional sense and is used to describe a protein that is a transport ATPase. ABC transporters are members of a large family of transport proteins that are ATP-dependent. The name is derived from a highly conserved ATP-binding cassette contained by all of the members. [See, Alberts et al., *Molecular Biology of the Cell*, 3rd edition, Garland Publishing Inc. (New York) Pages 519–522 (1994)]. MDR1 and BCRP are two transmembrane efflux pumps that are part of the family of ABC transporters.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment. The term "vector" can also refer to a recombinant virus or defective virus containing a replicon to which another DNA segment may be attached.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

A "coding sequence" is a nucleic acid sequence which can be reverse transcribed (i.e., when part of a retroviral vector) and/or transcribed and then translated into a polypeptide in vitro and/or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g. mammalian) DNA, and even synthetic DNA sequences. A polyadenylation signal and transcription termination sequence will usually be located 3' to the coding sequence.

A nucleic acid sequence is "operatively linked" to an expression control sequence when the expression control sequence controls and regulates the transcription and/or translation of that nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal for example, such a start signal can be inserted in front of the gene.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. Eukaryotic promoters will often, but not always, contain "TATA" boxes and "CAT" boxes.

A coding sequence is "under the control" of transcriptional and translational control sequences in a cell when RNA polymerase transcribes the coding sequence into mRNA, which is then translated into the protein encoded by the coding sequence.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma, adenovirus, herpes virus and other sequences known to control the expression of genes of mammalian cells, and various combinations thereof.

In selecting an expression control sequence, a variety of factors will normally be considered. These include, for example, the relative strength of the system, its controllability, and its compatibility with the particular DNA sequence or gene to be expressed, particularly as regards potential secondary structures. Considering these and other factors a person skilled in the art will be able to construct a variety of vector/expression control sequence combinations that will express the heterologous genes used in the present invention.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes. For instance, alpha-factor, a native yeast protein, is secreted from yeast, and its signal sequence can be attached to heterologous proteins to be secreted into the media (See U.S. Pat. No. 4,546,082, EPO 0 116 201, publication date Jan. 12, 1983; U.S. patent application Ser. No. 522,909, filed Aug. 12, 1983). Further, the alpha-factor leader and its analogs have been found to secrete heterologous proteins from a variety of yeast, such as Saccharomyces and Kluyveromyces, (EPO 88312306.9 filed Dec. 23, 1988; U.S. patent application Ser. No. 139,682, filed Dec. 30, 1987, and EPO Publication No. 0 301 669, publication date Feb. 1, 1989).

The phrase "pharmaceutically acceptable" refers to molecular entities and compositions that are physiologically tolerable and do not typically produce an allergic or similar untoward reaction, such as gastric upset, dizziness and the like. when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saliine solutions and aqueous dextrose and glycerol solutions are preferably employed as carriers, particularly for injectable solutions.

The phrase "therapeutically effective amount" is used herein to mean an amount sufficient to reduce by at least about 15 percent, preferably by at least 50 percent, more preferably by at least 90 percent, and most preferably prevent and/or treat, a clinically significant deficit in the activity, function and response of the host. Alternatively, a therapeutically effective amount is sufficient to cause an improvement in a clinically significant condition in the host.

Vectors

According to the present invention, the vector for ex vivo administration of the gene encoding an ABC transporter such as MDR1 or BCRP (i.e., a nucleic acid encoding MDR1 or BCRP respectively) and/or an alternative heterologous gene can be introduced via any strategy. Vectors can be introduced to transduce the desired host cells ex vivo by methods known in the art, e.g., transfection, electroporation, microinjection, cell fusion, DEAE dextran, calcium phosphate precipitation, lipofection (lysosome fusion), use of a gene gun, using a viral vector, with a DNA vector transporter, and the like. Alternatively, the vector can be introduced by lipofection.

Viral vectors are commonly used for ex vivo targeting and therapy procedures; these include DNA-based vectors and retroviral vectors. Methods for constructing and using viral sectors are known in the art [see, e.g., Miller and Rosman, *BioTechniques* 7:980–990 (1992)]. DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. In addition, different viral vectors may exhibit specificity for one or another cell type. Examples of particular vectors include, but are not limited to, a defective herpes virus 1 (HSV1) vector [Kaplitt et al., *Molec. Cell. Neurosci.* 2:320–330 (1991)], defective herpes virus vector lacking a glyco-protein L gene [Patent Publication RD 371005 a], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Stratford-Perricaudet et al. [*J. Clin. Invest.* 90:626–630 (1992); see also La Salle et al., *Science* 259:988–990 (1993)]; and a defective adeno-associated virus vector [Samulski et al., *J. Virol.* 61:3096–3101 (1987); Samulski et al., *J. Virol.* 63:382–3828 (1989); Lebkowski et al., *Mol. Cell. Biol.* 8:3988–3996 (1988)]. Herpes virus vectors are preferred for dendritic cells.

In another embodiment, the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; International Patent Publication No. WO 95/07358, published Mar. 16, 1995, by Dougherty et al.; and Kuo et al., 1993, Blood 82:845. International Patent Publication No. WO 95/07358 describes high efficiency transduction of primary B lymphocytes. In a specific embodiment, exemplified below, a Harvey murine retroviral vector is used to transduce hematopoietic stem cells. Retroviral vectors can be constructed to function as infectious particles or to undergo a single round of transfection. In the former case, the virus is modified to retain only those genes responsible for packaging and replication and to express the heterologous gene. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional virus.

For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo or ex vivo transfection of a gene encoding a marker [Felgner et. al., *Proc.Natl.Acad.Sci.USA* 84:7413–7417 (1987); see Mackey et al., *Proc.Natl.Acad.Sci.USA* 85:8027–8031 (1988); Ulmer et al., *Science* 259:1745–1748 (1993)]. The use of cationic lipids may promote encapsulation of negatively charged nucleic acids, and also promote fusion with negatively charged cell membranes [Felgner and Ringold, *Science* 337:387–388 (1989)].

It is also possible to introduce the vector as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990; Williams et al., *Proc.Natl.Acad.Sci. USA* 88:2726–2730 (1991)].

The present invention includes vectors containing a gene (i.e., a nucleic acid) encoding a transmembrane efflux pump, e.g., MDR1 or BCRP. Also included are truncated forms, analogs and derivatives of the transmembrane efflux pump, e.g., MDR1 that have essentially the same or improved functional activity as MDR1, for example. Therefore, the production and use of derivatives and analogs related to MDR1 or BCRP, for example, are within the scope of the present invention. In a specific embodiment, the derivative or analog is functionally active, i.e., capable of exhibiting one or more functional activities associated with a full-length, wild-type MDR1 protein.

In particular, MDR1 or BCRP derivatives, for example, can be made by altering encoding nucleic acid sequences by substitutions, additions or deletions that provide for functionally equivalent molecules. Preferably, derivatives are made that have enhanced or increased functional activity as it relates to the present invention, relative to the native MDR1 or BCRP, for example.

Due to the degeneracy of nucleotide coding sequences, other DNA sequences which encode substantially the same amino acid sequence as an ABC transporter gene, may be used in the practice of the present invention. These include but are not limited to nucleotide sequences comprising all or portions of the ABC transporter genes which are altered by the substitution of different codons that encode the same amino acid residue within the sequence, thus producing a silent change. Likewise the ABC transporter derivatives of the invention include, but are not limited to, those containing, as a primary amino acid sequence, all or part of the amino acid sequence of the ABC transporter protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosirie, asparagine, and glutamine. The positively charged (basic) amino acids include arginine, lysine and histidine. The negatively charged (acidic) amino acids include aspartic acid and glutamic acid.

Additionally, the nucleic acid sequence encoding the transmembrane efflux pump, such as BCRP, can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated BCRP gene product, for example. Any technique for mutagenesis known in the art can be used, including but not limited to, in vitro site-directed mutagenesis [Hutchinson, et al., *J. Biol. Chem.* 253:6551(1978),): Zoller and Smith, *DNA* 3:479–488 (1984); Oliphant et al., *Gene* 44:177 (1986); Hutchinson et al., *Proc.Natl.Acad.Sci. USA* 83:710 (1986), use of TAB® linkers (Pharmacia), etc. PCR techniques are preferred for site directed mutagenesis [see Higuchi, "Using PCR to Engineer DNA", in *PCR Technology: Principles and Applications for DNA Amplification,* H. Erlich, ed., Stockton Press, Chapter 6, pp. 61–70 (1989)].

Expression vectors containing a transmembrane efflux pump gene, such as the MDR1 gene, inserts can be identified by many ways including: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of a MDR1 gene inserted in an expression vector can be detected by nucleic acid hybridization using probes comprising sequences that are homologous to an inserted MDR1 gene. In the third approach, the recombinant vector/host system can be identified and selected based upon the presence or absence of certain "marker" gene functions (e.g., β-galactosidase activity, thymidine kinase activity, resistance to antibiotics, transformation phenotype, occlusion body formation in baculovirus, etc.) caused by the insertion of foreign genes in the vector. In the fourth approach, recombinant expression vectors can be identified by assaying for the activity and/or presence of the MDR1 gene product expressed by the recombinant.

Promoters

According to the present invention, the gene encoding an ABC transporter such as MDR1 or BCRP, and/or a second heterologous gene can be under the control of any promoter. In a specific embodiment, the human cytomegalovirus (CMV) immediate early promoter is used to effect transient expression of the ABC transporter. Alternatively, an inducible promoter can be used. However, the present invention contemplates use of any promoter to control expression of the ABC transporter. Selection of the promoter depends on the desired use. For example, expression of the ABC transporter may be controlled by any promoter/enhancer element known in the art, but these regulator elements must be functional in the host or host cell selected for expression. Promoters which may be used to control the ABC transporter gene expression include, but are not limited to, the SV40 early promoter region [Benoist and Chambon, Nature 290:304–310 (1981)], the promoter contained in the 3' long terminal repeat of Rous sarcoma virus [Yamamoto et al., Cell 22:787–797 (1980)], the herpes thymidine kinase promoter [Wagner et al. Proc. Natl. Acad. Sci. USA 78:1441–1445 (1981)], the regulatory sequences of the metallothionein gene [Brinster et al., Nature 296:39–42 (1982)]; and using a transcriptional control region such as the beta-globin gene control region which is active in myeloid cells [Mogram et al., Nature 315:338–340 (1985); Kollias et al., Cell 46:89–94 (1986)]. Alternatively, expression of the the ABC transporter gene can be under control of an inducible promoter, such as metallothionein promoter, which is induced by exposure to heavy metals.

Bone Marrow Transduction

Bone marrow cells can be obtained from any number of sources from an animal, including a human subject. For example, the cells can be harvested from iliac bone marrow. Alternatively, hematopoietic stem cells can be obtained from umbilical chord cells. Another source for hematopoietic stem cells is from circulating fetal blood cells. In addition, a human subject, for example, can be treated with a cytotoxic drug and/or a hematopoietic stem cell stimulating cytokine (e.g., G-CSF). Mononuclear cells can then be collected by leukophoresis and the hematopoietic stem cells can be isolated from the peripheral blood cells by their selective binding to an antibody raised against CD34.

In Example 1 below, bone marrow cells were flushed from the hind limbs of a laboratory animal and prestimulated for 48 hours in an appropriate medium. Dulbecco's modified essential medium supplemented with 15% fetal bovine serum, 100 units/ml penicillin, and 100 ng/ml streptomycin (P/S; Gibco-BRL) was also used in Example 1 below.

Growth factors can also be included in the suspension culture at the appropriate concentration. Following prestimulation cells can be co-cultured on irradiated retroviral producer cell lines (e.g., ecotropic producer cell lines for mice and amphotropic producer cell lines for humans) for 48 hours in the presence of the same growth factor combination but also with added 6 mg/ml polybrene (Sigma) to enhance transduction.

Ex Vivo Culture and Expansion of Myeloid Progenitors

After transduction, cells can be cultured. In Example 1 below, culturing was performed in the presence of interleukin-3, interleukin-6, and stem cell factor. Any other cytokine which supports the proliferation of hematopoietic stem cells could be used, including but not limited to GM-CSF, G-CSF and FI.T-3 ligand. It is preferred that when the hematopoietic stem cell is a human cell and/or the recipient is a human subject that the cytokines used also be the human homolog.

Cells are typically resuspended at $1\times10^6$ cells/ml every 3–6 days for at least 12 days of expansion. Aliquots of cells can be removed for CFU-C analysis at various time points. The percentage of drug-resistant progenitors can calculated by plating cells in methylcellulose (Stem Cell Technologies) for example, in the presence of selective concentrations of drugs. The percentage of transduced cells are generally found to remain constant throughout expansion.

Non-irradiated Recipient Bone Marrow Transplants

For bone marrow transplants into non-irradiated recipients, mice can receive from 1 to 10 daily intravenous injections with a vector containing a nucleic acid encoding MDR1, e.g., a total of $20\text{--}40\times10^6$ cells for the 5 day period exemplified below. (Humans can receive from 1 to 20 such daily intravenous injections, preferably 5 to 10 daily intravenous injections). Following a five day treatment course in Example 1 below, the presence of a donor marker protein, Hb as exemplified below, can be monitored in recipient animal (as exemplified below the monitoring began at one week after the last injection), and then followed for as long as appropriate, (8 to 14 months in Example 1 below).

Transduction of Murine Bone Marrow Cells with ABC Transporter Vectors

HSC expansion, the development of abnormal myeloproliferation and overexpression, of ABC transporters: Retroviral vectors that express ABC transporters such as those constructed to encode BCRP and MRP4 can be used to transduce murine bone marrow cells. These transduced grafts can then be evaluated for stem cell expansion in competitive repopulation studies to determine if HSCs are amplified in vitro or in vivo. Transplanted mice can be followed over time for evidence of abnormal peripheral blood counts and myeloproliferation. ABC transporters are identified that can efflux Hoechst dye and mediate the SP cell phenotype. The cDNAs that encode the ABC transporters can then be tested in the retroviral vector system as described herein.

Resistance to apoptosis and/or differentiation: Murine bone marrow cells can be transduced with the HaMDR1sc vector, and grown for 6 days in culture in the presence of cytokines and serum. Then, the cells can be replated in media that contains no serum or cytokines to induce apoptosis. Annexin and tunnel staining can be performed to determine the number of cells undergoing apoptosis, and the survival of clonogenic cells under apoptosis-inducing conditions can be determined by colony growth in methycellulose-containing media. When an anti-apoptotic effect is demonstrated, the mechanism by which apoptosis is inhibited can be determined. One such method includes looking for the activation of members of the caspase pathway, and determining the distribution of phosphotidylserine in the cell membrane of transduced, sorted cells. When no effects on apoptosis are observed, it can be determined whether ABC transporter expression is leading to an accumulation of HSCs by inducing a differentiation block. FDCP-Mix cells can be transduced with HaMDR1sc and evaluated for changes in cytokine-induced differentiation. Primary murine HSCs can also be studied by evaluating transduced and control cultures for the number of lineage-, CD34-, kit+, sca1+ cells in cultures at various time points in culture. Loss of cells bearing this primitive stem cell phenotype has been reported using normal cells, and is thought to be due to differentiation of HSCs in culture. Any vector comprising an ABC transporter can be evaluated in this way including the HaMDR1 vector and vectors comprising BCRP or MRP4. The results can also be re-evaluated in human bone marrow CD34+ cells using an RD18-derived HaMDR1sc vector, for example.

Defining the downstream changes in gene regulation associated with MDR1-mediated HSC expansion: The ability to isolate expanding stem cells in MDR1-transduced cultures allows the evaluation of changes in gene expression that are associated with stem cell expansion. Thus, murine bone marrow cells can be transduced, and expanded in culture in parallel with mock-transduced cells. After 6 days of expansion, SP cells can be isolated by cell sorting from the transduced population. SP cells generally are not expected in the mock-transduced population at after 6 days, so as control population for subtractive analysis, Sca1-, lineage negative cells, for example, can be isolated from the cultured mock population. RNA can be isolated from both populations, and analyzed by hybridization with matrix-based gene arrays. RNA can be isolated to make suitable fluorescent probes. Alternatively, a sensitive PCR-based subtraction method can be used to identify genes that are upregulated in the transduced, expanding stem cells. Differentially expressed products can be sequenced, and used to generate probes for further expression in normal stem cell populations. Genes encoding upregulated and downregulated mRNAs can be selected and cloned, and functionally analyzed in overexpression experiments using retroviral vectors similar to those described herein.

Antibodies to the ABC Transporters of the Present Invention

According to the present invention, ABC transporters as produced by a recombinant source, or through chemical synthesis, or an ABC transporter isolated from a natural source; and derivatives or analogs thereof, including fusion proteins, may be used as an immunogen to generate antibodies that recognize an ABC transporter such as BCRP. Although exemplified for BCRP, the methodologies regarding making antibodies, as discussed below, are applicable for all of the ABC transporters of the present invention. Such antibodies include but are not limited to polyclonal, monoclonal, chimeric including humanized chimeric, single chain, Fab fragments, and a Fab expression library.

In a particular embodiment an antibody is raised to an external epitope of BCRP. In a particular embodiment the epitope is derived from the extracellular portion of BCRP. Such an antibody can be used to sort living cells on a flow cytometer. These antibodies can be used, for example, to sort hematopoietic cells based on BCRP (bcrp) expression. Such antibodies also may be used to detect BCRP as a marker for repopulating activity.

The anti-BCRP antibodies of the invention may be cross reactive, that is, they may recognize a BCRP derived from a different source, e.g., an anti-human BCRP antibody may recognize both human and mouse BCRP. Polyclonal antibodies have greater likelihood of cross reactivity. Alternatively, an antibody of the invention may be specific for a single form of a BCRP, such as the hBCRP having the amino acid sequence of SEQ ID NO:10.

Various procedures known in the art may be used for the production of polyclonal antibodies to BCRP, for example, or derivative or analog thereof. For the production of antibody, various host animals can be immunized by injection with the BCRP, or a derivative (e.g., or fusion protein) thereof, including but not limited to rabbits, mice, rats, sheep, goats, etc. In one embodiment, the BCRP can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the BCRP, or analog, or derivative thereof, any technique that provides for the production of antibody molecules by continuous cell lines in culture may be used. These include but are not limited to the hybridoma technique originally developed by Kohler and Milstein [*Nature*, 256:495–497 (1975)], as well as the trioma technique, the human B-cell hybridoma technique [Kozbor et al., *Immunology Today*, 4:72 (1983); Cote et al., *Proc. Natl. Acad. Sci. USA*, 80:2026–2030 (1983)], and the EBV-hybridoma technique to produce human monoclonal antibodies [Cole et al., in *Monoclonal Antitibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.*, 159:870 (1984); Neuberger et al., *Nature*, 312:604–608 (1984); Takeda et al., *Nature* 314:452–454 (1985)] by splicing the genes from a mouse antibody molecule specific for a BCRP together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves. In a particular embodiment, the BCRP-expressing producer cells of the present invention are used to raise monoclonal antibodies to external cell surface epitopes. Antibody producer clones can be screened for differential staining of producer cells versus their parental packaging cells.

According to the invention, techniques described for the production of single chain antibodies [U.S. Pat. Nos. 5,476, 786 and 5,132,405 to Huston; U.S. Pat. No. 4,946,778] can be adapted to produce for example, BCRP-specific single chain antibodies. An additional embodiment of the invention utilizes the techniques described for the construction of Fab expression libraries [Huse et al., Science, 246:1275–1281 (1989)] to allow rapid and easy identification of monoclonal Fab fragments with the desired specificity for a BCRP, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example). Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of BCRP, one may assay generated hybridomas for a product which binds to the BCRP fragment containing such epitope and choose those which do not cross-react with BCRP. For selection of an antibody specific to a BCRP from a particular source, one can select on the basis of positive binding with BCRP expressed by or isolated from that specific source.

The foregoing antibodies can be used in methods known in the art relating to the localization and activity of the BCRP, e.g., for Western blotting, imaging BCRP in situ, measuring levels thereof in appropriate physiological samples, etc, using any of the detection techniques mentioned herein or known in the art. In a specific embodiment, antibodies that agonize or antagonize the activity of BCRP can be generated. Such antibodies can be tested using the assays that measure the drug pumping ability of BCRP, for example.

The antibodies to the ABC transporters can be labeled. Suitable labels include enzymes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. In the instance where a radioactive label, such as the isotopes $^3H$, $^{14}C$, $^{32}P$, $^{35}S$, $^{125}I$, and $^{131}I$, are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. ultraviolet light to promote fluorescence. Among examples of colored labels, which can be used according to the present invention, include metallic sol particles, for example, gold sol particles such as those described by Leuvering (U.S. Pat. No. 4,313,734): dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70:419–439 (1980) and in U.S. Pat. No. 4,857,453.

Suitable enzymes include, but are not limited to, alkaline phosphatase and horseradish peroxidase. In addition, an antibody can be modified to contain a marker protein such as green fluorescent protein as described in U.S. Pat. No. 5,625,048 filed Apr. 29, 1997, WO 97/26333, published Jul. 24, 1997 and WO 99/64592 all of which are hereby incorporated by reference in their entireties. Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

Antibodies also can be labeled by metabolic labeling. Metabolic labeling occurs during in vitro incubation of the cells that express the protein in the presence of culture medium supplemented with a metabolic label, such as [$^{35}S$]-methionine or [$^{32}P$]-orthophosphate. In addition to metabolic (or biosynthetic) labeling with [$^{35}S$]-methionine, the invention further contemplates labeling with [$^{14}C$]-amino acids and [$^3H$]-amino acids (with the tritium substituted at non-labile positions).

Stem Cell Purification

After an appropriate antibody is identified, mouse bone marrow cells, for example, can be depleted of lineage positive cells, and the lin—cells can be sorted for BCRP expression. Competitive repopulation assays can then be used to demonstrate the enrichment ofstem cell activity in the BCRP-expressing fraction. BCRP sorting experiments can also be performed in lin-, ckit+, sca1+ cells, and in CD34– cells to determine if these populations can be further enriched for stem cell activity. An analogous procedure can be performed using an alternative cell source, e.g., human cord blood cells.

Thus, BCRP sorting experiments can be performed using Lin-, CD34– cells, as well as CD34+, 38– cells to determine the amount that BCRP expression enriches for repopulating activity in these stem cell populations. Sorted cells then can be injected into NOD/SCID mice in limiting dilution analyses to quantity the stem cell frequencies in these populations. This procedure can be repeated using bone marrow cells and cytokine-mobilized peripheral blood stem cells to demonstrate the utility of the procedure in various clinical stem cell sources. For example, SP cells were isolated from mouse muscle satellite cells and RT-PCR and FACS analysis was used to demonstrate that Bcrp is also expressed in these cells (see Example 3 below). Reconstitution studies can also be performed using sorted bcrp-expressing muscle cells. Sorted donor cells can be identified after transplant using a GFP-transgenic mouse line for donor cells, for example, and analyzing recipients for GFP+ SP cells in the muscle.

Therefore, the present invention provides a functional basis for identifying SP stem cells, and furthermore, provides a new way to isolate stem cells both for research and clinical applications. For example, the present invention provides a method of isolating stem cells using an anti-RCRP antibody. These stein cells can originate from any tissue that contains stem cells including from bone marrow cells, muscle cells and even brain cells. Any method that allows the separation of cells that can be distinguished by their ability to bind a particular antibody can be employed. For example, to isolate hematopoietic stem cells, bone marrow cells can be obtained from an animal subject, (preferably a human). Single cell suspensions can then be prepared. An anti-BCRP antibody can be incubated with the cells and the cells can be isolated using standard cell sorting methodology e.g., by fluorescent cell sorting [Bhatia et al., *Nat. Med.* 4:1038–1045 (1998)]. In a related embodiment, muscle stem cells can be isolated from a muscle cell sample [Gussoni et al., *Nature* 401:390 (1999)]. Alternatively, stem cells can be distinguished from non-stem cells by the specificity of the drug-pumping activity of BCRP.

Antisense and Gene Targeting

Given the highly specific expression of Bcrp1 in hematopoietic stem cells, and the association of enforced ABC transporter expression with stem cell expansion, either the Bcrp1 and/or mdr1a/b genes appear to be required for normal stem cell function. Furthermore, the functional activity of an ABC transporter, and in particular BCRP or MRR1 can be evaluated with transgenic, knockout, or knockin animals. Therefore, the present invention provides transgenic, knockin, and knockout animals. In one embodiment of this type the knockin animal is a mouse. In another embodiment the animal is a knockout mouse. One embodiment comprises a disruption in an endogenous alleles encoding BCRP, which prevents the expression of functional BCRP from that individual allele. In another embodiment, the disruption is in both endogenous alleles that encode BCRP, preventing the knockout animal from expressing functional endogenous BCRP. Although a transgenic/knockin/knockout mouse is preferred other rodents such as rats and rabbits, or mammals such as pigs, goats, sheep, and monkeys can also be used.

The present invention also includes non-human transgenic or knockin animals that comprise cells that express an ABC transporter variant of the present invention. For example, a mouse comprising the HaMDR1Δ34 described in the Examples below. Such a transgenic or knockin animal can be used as a control, for example when identifying and testing drugs that can be useful treating leukemia for example. Thus the transgenic, knockin, and knockout animals of the present invention can be used in drug screens and the like. Cells from the transgenic, knockin and knockout mice are also part of the present invention, as are cells that are made in situ to overexpress or alternatively, to not express the ABC transporters of the present invention.

The ABC Transporter genes such as the Bcrp gene also call be used in complementation studies employing transgenic mice. Transgenic vectors, including viral vectors, or cosmid clones (or phage clones) corresponding to the wild type locus of candidate gene, can be constructed using the isolated Bcrp gene. Cosmids may be introduced into transgenic mice using published procedures [Jaenisch, *Science,* 240:1468–1474 (1988)]. In a particular embodiment, a mouse Bcrp gene can be placed into a transgenic or knockin mouse and compared with a wild-type mouse. Similarly, transgenic or knockin animals other than mice may also be generated and used.

A transgenic or knockin animal can thus be prepared that expresses a recombinant BCRP or a fragment thereof Such transgenic animals can be obtained through gene therapy techniques described above or by microinjection of a nucleic acid [such as a bacterial artificial chromosome (BAC) that encodes a BCRP variant] for example, into an embryonic stem cell or an animal zygote. Microinjection of BACs has been shown to be successful in a number of animals including rats, rabbits, pigs, goats, sheep, and cows [in *Transgenic Animals Generation and Use* ed., L. M. Houdebine, Harwood Academic Publishers, The Netherlands (1997)]. Methods of constructing BACs [or other DNAs such as bacteriophage P1 derived artificial chromosomes (PACs)] that encode specific nucleic acids through homologous recombination have recently been described in great detail [Heintz et al., PCT/US98/12966, (1998) the contents of which are hereby incorporated by reference in its entirety]. Alternatively, a yeast artificial chromosome (YAC) that encodes a BCRP variant for example, can be used. In a preferred embodiment the transgenic animal is a mouse.

Alternatively, an animal model can be prepared in which expression of the BCRP gene is disrupted. Gene expression is disrupted, according to the invention, when no functional protein is expressed. One standard method to evaluate the phenotypic effect of a gene product is to employ knock-out technology to delete a gene as described in U.S. Pat. No. 5,464,764, Issued Nov. 7, 1995; and U.S. Pat. No. 5,777, 195, Issued Jul. 7, 1998 (both of which are hereby incorporated by reference herein in their entireties.)

In a specific embodiment, PCR can be used to generate a probe encompassing the first 500 basepairs, for example, of the Bcrp1 cDNA. This probe can be used to screen a commercially available library of bacterial artificial chromosomes (BACs). The BAC comprising the corresponding Bcrp1 gene is then used in typical gene targeting methodology.

The knockout mice can be constructed by replacing the ATP-binding cassette of Bcrp with $Neo^R$ targeting constructs for example. The resulting Bcrp knockout mice can be analyzed for hematopoietic function using standard assays, and for stem cell content using competitive repopulation assays. Hematopoiesis can also be assessed in the embryo and transplant studies can be perform with fetal liver cells. Alternatively, conditional knockouts can be prepared in which the ATP-hydrolysis region is flanked by LoxP sites. Bone marrow cells from the adult mice then can be transduced with a retroviral vector that expresses both Cre recombinase, and a linked marker gene, e.g., green fluorescent protein. Transduced cells are sorted for marker expression. Quatitative repopulating studies can be performed to correlate loss of Bcrp expression with defects in stem cell function.

The BCRP knockout mice also can be crossed with mdr1a/1b knockout mice. Mrp4 mice also can be crossed either with Bcrp −/−, with the mdr1a/1b knockout mice or with the Bcrp −/−, mdr1a/1b triple knockout mice. These mice can be used to determine whether one or more of the particular ABC transporters are required for stem cell function, since the absence of repopulating stem cells in any of the particular knockout mice will indicate that the corresponding ABC transporter(s) is indeed required. In addition, other ABC transporters from sorted SP cells can be expression cloned and studied as described above.

In yet another aspect of the invention a knockin animal is made. A knockin animal is prepared in an analogous manner as a knockout animal except a variant/modified exon or gene is substituted for the exon or gene of interest through homologous recombination, rather than disrupting the gene. A gene-targeting strategy can be used that utilizes a replacement vector containing a particular point mutation and a neo gene flanked by loxP sites to construct the mutation in mice. This procedure is known as the Pointlox procedure [Giese et al. *Science* 279:870–873 (1998)].

The present invention also extends to the preparation of antisense nucleotides and ribozymes that may be used to interfere with the expression of the Bcrp gene. These approaches utilize either an antisense nucleic acid to block translation of a specific mRNA, by masking that mRNA with an antisense nucleic acid or a ribozyme that specifically cleaves the mRNA.

Antisense nucleic acids are DNA or RNA molecules that are complementary to at least a portion of a specific mRNA molecule [See Weintraub, *Sci. Amer.* 262:40–46 (1990); Marcus-Sekura, *Nucl. Acid Res,* 15: 5749–5763 (1987); Marcus-Sekura *Anal.Biochem.,* 172:289–295 (1988); Brysch et al., *Cell Mol. Neurobiol* 14:557–568 (1994)]. Preferably, the antisense molecule employed is complementary to a substantial portion of the mRNA. In the cell, the antisense molecule hybridizes to that mRNA, forming a double stranded molecule. The cell does not translate an mRNA in this double-stranded form. Therefore, antisense nucleic acids interfere with the expression of mRNA into protein. Preferably a DNA antisense nucleic acid is employed since such an RNA/DNA duplex is a preferred substrate for RNase H. Oligomers of greater than about fifteen nucleotides and molecules that hybridize to the AUG initiation codon will be particularly efficient. Antisense methods have been used to inhibit the expression of many genes ice vitro [Marcus-Sekura, *Anal.Biochem.,* 172:289–295 (1988); Hambor et al., *Proc. Natl. Acad. Sci. USA* 85:4010–4014 (1988)] and in situ [Arima et al., *Antisense Nucl. Acid Drug Dev.* 8:319–327 (1998); Hou et al., *Antisense Nucl. Acid Drug Dev.* 8:295–308 (1998)]. The DNA sequences of BCRP included herein may thus be used to prepare antisense molecules against mRNAs encoding the BCRP protein.

BCRP Expression and AML

A significant number of AML blasts can efflux fluorescent dyes, despite the absence of MDR1 and MRP1 expression. A substantial proportion of these cases may be due to the overexpression of BCRP. AML blasts from newly diagnosed pediatric patients can be assayed using flow cytometry after staining with a specific anti-BCRP antibody. In cases where BCRP expression is dysregulated, it can be determiied whether the overexpression BCRP is due to mutations in the promoter, hypomethylation of promoter sequences, or due to changes in the transcription factor environment. The correlation between BCRP expression the response to induction treatment, and the prognosis can then be made.

The present invention may be better understood by reference to the following non-limiting Examples, which are provided as exemplary of the invention. These examples are presented in order to more fully illustrate the preferred embodiments of the invention. They should in no way be construed, however, as limiting the broad scope of the invention.

EXAMPLE 1

Ex Vivo Expansion of Murine Hematopoietic Stem Cells Transduced with an MDR1 Retroviral Vector Introduction Initial studies were intended to determine whether gene-modified progenitors could be expanded in culture and whether these relatively mature transduced cells would be useful for chemoprotection against myelosuppression in mice receiving antifolate chemotherapy. This progenitor approach previously has been shown effective with vectors expressing methyguanine DNA methyltransferase [MGMT] and protective against 1,3-bis(2-chloroethly)-1-nitrosourea [BCNU] mediated delayed myelosuppression. Unexpectedly, mice receiving bone marrow transduced with an MDR1 retrovirus showed sustained engraftment in non-irradiated recipients. In addition, subsequent quantitation of the stem cell content by competitive repopulation experiments in lethally-irradiated mice indicated a large increase in the repopulation potential with expanded MDR1 marrow. Such results were surprising since there had been numerous observations of negative effects of the expansion of stem cells when alternative gene-modified progenitors had been generated. A myeloproliferative disorder did result in some cases, since a fraction of mice engrafted with MDR1 marrow developed a myeloproliferative disorder characterized by high peripheral white blood cell counts and splenomegaly. This disorder, howvever, was not found to be absolutely linked to the stem cell expansion described herein.

Methods

Retroviral producer cell lines and vector constructs: The Harvey (Ha)MDR1 and HaDHFRL22Y vectors and ecotropic producer cell lines were generated as described previously [Sorrentino et al., Science 257: 99–103 (1992); Galipeau et al., *Human Gene Therapy* 8:1771–1783 (1997), hereby incorporated by reference in their entireties]. The MDR1 protein (encoded by SEQ ID NO:1 and having the amino acid sequence of SEQ ID NO:2) contains a wild-type glycine 185 amino acid. Wild-type MDR1 shows increased resistance to etoposide and decreased resistance to vinca alkaloids when compared with the valine 185 mutant (encoded by SEQ ID NO:3 and having the amino acid sequence of SEQ ID NO:4). The MDR1 cDNA has been previously splice-corrected to allow for optimal levels of active protein expression in transduced cells [Galipeau et al., *Human Gene Therapy* 8:1771–1783 (1997)]. The DHFRL22Y protein contains a leucine to tyrosine mutation at codon 22 (L22Y) which greatly optimizes resistance to trimetrexate [Spencer et al., *Blood* 87:2579–2587 (1996)].

Retroviral-mediated bone marrow transduction: Bone marrow cells were flushed from the hind limbs of either C57/B16 (C57) or B6.C-H1/BY (HW80) congenic mouse strains (day −4) and prestimulated for 48 hours in Dulbecco's modified essential medium (DMEM; BioWhittaker, Walkersville, Md.) supplemented with 15% fetal bovine serum, 100 units/ml penicillin. and 100 ng/ml streptomycin (P/S; Gibco-BRL). Growth factors were also included in the suspension culture at the following concentrations; 20 ng/ml murine IL-3 (Amgen), 50 ng/ml human IL-6 (Amgen), and 50 ng/ml murine SCF (Amgen and R & D Systems) as previously described. Following prestimulation (day −2), cells were co-cultured on irradiated (1500 rads) GP+E86 ecotropic producer cell lines for 48 hours in the presence of the same growth factor combination but also with added 6 mg/ml polybrene (Sigma) to enhance transduction. C57/B16 donor mice have a single hemoglobin (Hb) pattern while HW80 have a diffuse Hb pattern when separated on cellulose acetate gels (Helena Laboratories, Beaumont, Tex.). These Hb patterns were subsequently utilized for characterization of engraftment.

Ex vivo culture and expansion of myeloid progenitors: Following transduction (day 0), cells were cultured in the presence of the growth factor combination described above. Cells were resuspended at $1 \times 10^6$ cells/ml every 3–6 days for at least 12 days of expansion. Aliquots of cells were removed for CFU-C analysis at various time points. The percentage of drug-resistant progenitors was calculated by plating cells in methylcellulose (Stem Cell Technologies) in the presence of selective concentrations of drugs. MDR-transduced progenitors were resistant to 50 ng/ml taxol and DHFR-transduced progenitors were resistant to 25 to 50 nM trimetrexate. These concentrations of trimetrexate completely killed non-transduced background cells when plated in thymidine phosphorylase-treated methylcellulose. The percentage of transduced cells was found to remain constant through expansion. Average progenitor transduction efficiencies were: MDR1 Taxo1R (40.3+10.2%), DHFR TrimetrexateR (39.6+17.8%).

Non-irradiated recipient bone marrow transplants: During bone marrow transplant into non-irradiated recipients, mice received 5 daily intravenous injections with either MDR- or DHFR-transduced bone marrow cells (total of $20-40 \times 10^6$ cells for the 5 day period). Later each day mice also received intraperitoneal injection with trimetrexate (130 mg/kg) and the nucleoside transport inhibitor nitrobenzylmercaptopurine riboside phosphate (NBMPR-P; 20 mg/kg). Following this five day treatment course, the presence of donor Hb was monitored in recipient mice beginning at one week and followed for 8 to 14 months. Trimetrexate-glucuronate was received as the base from the Drug Synthesis and Chemistry Branch, Developmental Therapeutics Program, Division of Cancer Treatment, NCI. It was converted to the glucuronate form as described previously [Spencer et al., *Blood* 87:2579–2587 (1996)].

Competitive repopulation assays: Expanded MDR1 transduced cells were mixed either with the indicated donor hind limbs volume of 12 day expanded DHFRL22Y transduced cells or with freshly harvested marrow. Cells were mixed thoroughly and injected via the tail-vein into lethally-irradiated (925–1000 rads) recipient mice. Beginning at 10 weeks post-transplant, Hb patterns were analyzed by electrophoresis on cellulose acetate gels to calculate the relative proportions of single and diffuse donor hemoglobin in reconstituted nice. The results of these analyses were quantitated by densitometry.

Secondary bone marrow transplants: Bone marrow was harvested from primary recipients from 10 to 24 weeks following transplant and injected into lethally-irradiated secondary recipients. Secondary transplanted mice received at least $5 \times 10^6$ bone marrow cells. Hb patterns were monitored in secondary recipients after reconstitution (8 to 10 weeks). Secondary CFU-S wvere harvested 12 days following injection of $1-5 \times 10^4$ cells and DNA was prepared for Southern blot analysis for the presence of the MDR1 transgene.

Southern blot analysis: DNA was prepared as previously described [Sorrentino et al., Science 257: 99–103 (1992)]. Typically 10 to 20 mg of genomic DNA was restriction digested with either EcoR1 or NheI, and separated on a 1% agarose gel. Gels were blotted overnight onto Hybond N+ nylon membrane (Amersham), UV crosslinked, and hybridized with either MDR1 or hemoglobin-specific [32P]-labeled probes. Blots were washed extensively at 65° C., exposed overnight, and analyzed on a phosphorimager (Molecular Dynamics).

Detection of human p-glycoprotein on mouse erythrocytes: One microliter of murine whole blood containing approximately $6 \times 10^6$ erythrocytes was washed in PBS and resuspended in 0.5 ml of Fc-Block (Pharmingen, San Diego, Calif.) in a final volume of 20 ml of PBS. The red cells were washed and resuspended in PBS with 0.3 mg of unlabeled primary anti-human Pgp monoclonal murine antibody 4E3 (M3523, Dako Corporation, Carpinteria, Calif.). Cells were next incubated with primary antibody for 45 minutes at room temperature. Cells were then washed and incubated with a phycoerythrin-linked goat anti-mouse IgG antibody (Caltag Laboratories, Burinlgame, Calif.) for 30 minutes at room temperature. Cells were next washed and analyzed by flow cytometry. Red cells and platelets were identified by the characteristic forward and side scatter distribution. Red cells were gated and analyzed for PE. Leukocytes are located within the erythrocyte gate but these constitute less than 0.1% of all events.

Detection of human p-glycoprotein on mouse leukocytes: Murine whole blood was collected in heparinized tubes and diluted in PBS. Red blood cells were lysed in Gey's solution for 5 minutes on ice. White blood cells were blocked for 15 minutes in PBS/0.1% BSA/10% normal mouse serum followed by staining with a FITC-labeled murine monoclonal anti-human p-glycoprotein antibody (4E3-FITC; Signet Laboratories Inc., Dedham, Mass.) or with the isotype control. Cells were then analyzed by flow cytometry for FITC-positivity. Gates were drawn on the abnormal population apparent on forward and side scatter profiles in mice with a myeloproliferative disorder.

Assays for replication-competent retrovirus: Genomic DNA was prepared from either cultured producer cell lines, transduced 3T3 cells, or peripheral white blood cells. PCR was performed using primers specific for the 3' end of pol and the 5' end of env regions of the helper virus genome which have been previously described [Scarpa, *Virology* 180:849 (1991)]. PCR was performed under the following conditions: 94° C., 1.5 minutes denaturation; 55° C., 1.0 minute annealing; 72° C., 1.5 minutes extension; 28 cycles. In addition, marker rescue assays were performed on supernatant from producer cell lines and plasma samples from transplanted mice. A M.dunni/G1Na-transduced cell line was used as the target for marker rescue. Following addition of supernatant, M.dunni/G1Na cells were cultured for at least 2 weeks and supernatant from these cells was assayed at intervals for liberation of infectious retrovirus containing the neo gene. Supernatant were transferred to naive M.dunni cells for 48 hours followed by selection in 0.8 mg/ml G418 (active). No G418R colonies were obtained in multiple experiments at a concentration in which M.dunni/G1Na cells were highly resistant.

Stem cell expansion calculation: $0.005/0.25+0.005=0.02$ predicted engraftment percentage if no stem cell expansion had occurred. Observed engraftment levels 0.25 to 1.0 indicate an increase in stem cell content of at least 10-fold. It should be noted that engraftment levels were constantly increasing thus any single measurement likely underestimates the true stem cell expansion.

Results

Ex vivo expansion of retrovirally-transduced murine myeloid progenitors was performed as follows. Bone marrow cells were harvested front either C57/Bl6 (C57) or B6.C-H1/BY (HW80) mice (day −4) and transduced by co-culttire on retroviral producer cell lines. Producer cells included all MDR1sc producer which expresses the splice-corrected version of the human MDR1 cDNA and a resistance-conferring dihydrofolate reductase (DHFR) mutant referred to as DHFRL22Y. Following transduction (day 0), cells placed into liquid suspension culture for a period of 12 days expanded logarithmically (FIG. 1A). At three day intervals, an aliquot of cells was removed and plated in methylcellulose for assay of the progenitor content. Total progenitor and drug-resistant progenitor levels were calculated and monitored over time. The percentage of progenitors within the total cell population peaked at levels close to 20% between 3 and 6 days following, initiation of culture and then gradually declined with time. This transient relative enrichment in progenitors is likely due to death of differentiated cells and expansion of the progenitor pool. The absolute numbers of both drug-resistant and drug-sensitive progenitor populations expanded equally during culture. Thus, the relative percentage of drug-resistant progenitors remained constant throughout the 12 days in culture. Examples of representative expansions are shown for both MDR1 and DHFR-transduced drug-resistant progenitors (FIG. 1B). Typical expansions yielded a 100-fold increase by 2 weeks.

Figure 2B:
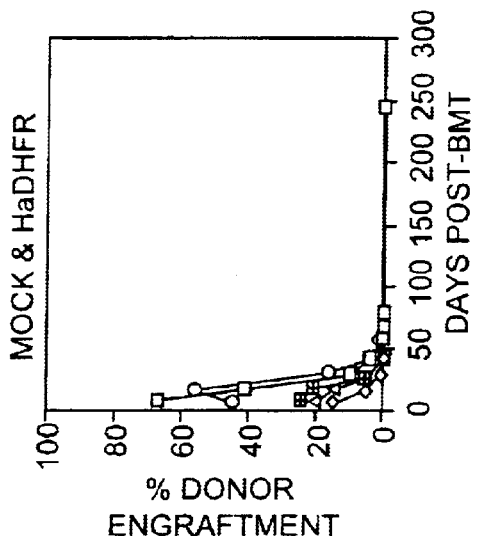
Figure 2D:
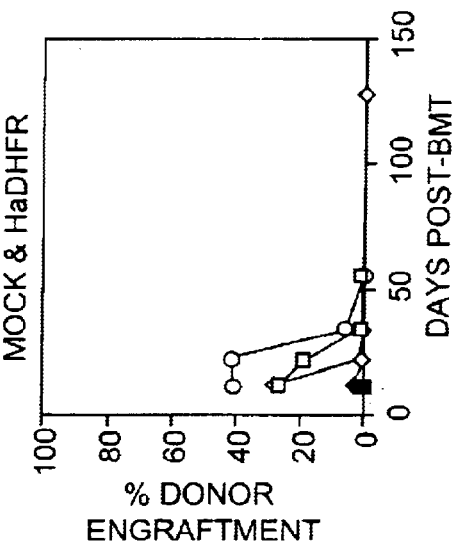
Figures 1, 3D:
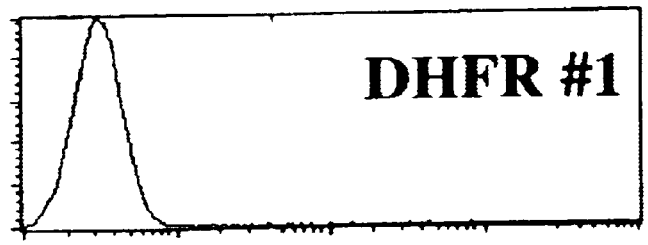
FIGS. 3D–1 to 3D–5 show the FACS analysis for P-glycoprotein (Pgp) expression in red blood cells from engrafted mice. Peripheral red blood cells were stained with a monoclonal antibody to human Pgp followed by FACS analysis for the PE chromophore. As a negative control, a mouse injected with HaDHFR-transduced marrow (DHFR #1) is shown. All 4 mice from expt. #2 analyzed at 10 weeks post-transplant demonstrate significant levels of Pgp positive red blood cells. When corrected for the percent donor red cells present at the time of analysis, levels of Pgp positivity approached 100% of circulating donor red blood cells.
Figures 2, 3D:
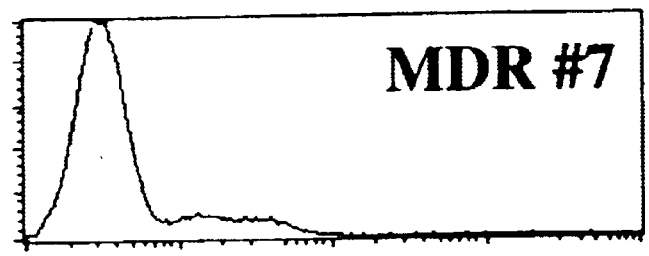
Figures 3, 3D:
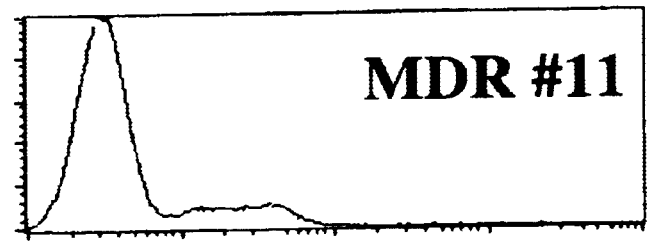

Long-term engraftment of MDR-transduced hematopoietic stem cells was observed in non-irradiated recipient mice. The expansion of cells capable of long-term engraftment in a non-irradiated mouse model was unexpected. MDR- or DHFR-transduced and expanded cells were initially injected into mice with the purpose of testing whether short-term engraftment of drug-resistant progenitors would be protective against antifolate-induced myelosuppression. Recipient mice were treated for 5 days with trimetrexate in combination with the nucleoside transport inhibitor nitrobenzylmercaptopurine riboside phosphate (NBMPR-P). Mice were injected with 12–16 day-expanded cells on each of the 5 days of drug treatment. Following transplant the donor hemoglobin (Hb) levels were monitored in the recipient mice beginning at 1 week and continued through greater than 1 year following injection (FIGS. 2A–2B). Donor Hb was present in varying, levels in all mice receiving cells as early as 1 week following injection (the earliest time point examined). However, this engraftment was only transient in mice receiving DHFR- or mock-transduced marrow (0/16; from 2 separate expansion experiments, FIG. 2A). By contrast, 5/12 mice which received MDR-transduced marrow showed long-term engraftment which was stable for more than 6 months post BMT (FIG. 2B), and up to 14 months in the latest time point obtained. Representative Hb electrophoresis profiles for primary engrafted recipients demonstrated the presence of C57 donor Hb at time points 5 to 7 months following injection (FIGS. 3A–3B). In addition, secondary recipients from mouse #20 showed a range from 50–100% C57 donor Hb 8 weeks after transplant indicating engraftment of the primitive long-term repopulating cells (FIG. 3C). High level expression of P-glycoprotein was seen in donor red blood cells at greater than 10 weeks following transplant in all 4 mice engrafted from experiment #1 (FIG. 3D). The FACS data shows expression in total red blood cells and when corrected for donor chimerism at the same day of analysis the levels were found to range from 80–100% positivity. DHFR mouse #1 served as a negative control for P-glycoprotein expression.

Figures 3, 3D, 4:
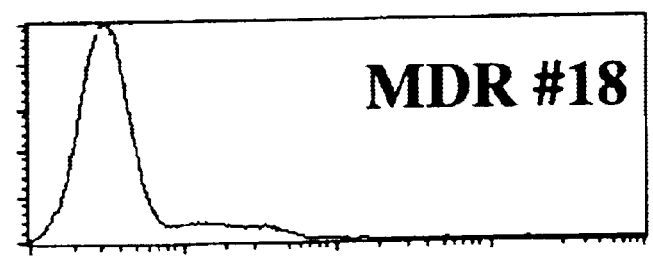

Expansion of the MDR-transduced hematopoietic stem cells was quantified by competitive repopulation assay. Thus, to examine whether stem cell expansion was responsible for the high levels of engraftment obtained in the non-irradiated model, a competitive repopulation model was used. MDR- and DHFR-transduced cells were expanded over a 12 day period as described in the Methods, above. Table 1 shows the calculation of the percent hind limbs volume remaining at various time points during the expansion. On day 12. MDR-transduced cells were mixed in an equal volume:volume ratio with expanded day 12 DHFR-transduced cells and injected into lethally-irradiated recipient mice (FIG. 4A, right). Also, expanded MDR cells (0.005 C57 donor volumes, FIG. 4A, left) or expanded DHFR cells (0.005 C57 donor volumes FIG. 4A, middle) were mixed with freshly isolated cells with the opposing Hb pattern (0.25 donor volumes) and injected into lethally-irradiated recipients. Beginning at 10 weeks the Hb patterns in recipient mice were analyzed by Hb electrophoresis (FIG. 4C). Interestingly, MDR-expanded marrow completely out competed identically expanded DHFR marrow in repopulation of recipient mice indicating a much higher stem cell content, (lanes 4–10 of FIG. 4C). But most surprising was the very high level of engraftment of MDR marrow when competed against fresh marrow (lanes 1 and 2 of FIG. 4C.). By contrast, when DHFR marrow was competed against fresh marrow it was completely outcompietd (lanes 3 and 4 of FIG. 4C). In addition, over time mice consistently lost their chimerism and approached 100%, donor as was seen in the unirradiated model.

TABLE 1

Calculation of Total Cell Expansion and Percent Hind Limbs Volume Remaining

| | HaMDR | | | HaDHFR | | |
|---|---|---|---|---|---|---|
| Day | Cell Number* | Volume fraction replated | Fraction hind limbs volume | Cell Number* | Volume fraction replated | Fraction hind limbs volume |
| 0 | $2.15 \times 10^7$ | 1.00 | 0.86 | $2.06 \times 10^7$ | 1.00 | 1.00 |
| 3 | $9.2 \times 10^7$ | 0.22 | 0.19 | $6.2 \times 10^7$ | 0.22 | 0.22 |
| 6 | $6.6 \times 10^7$ | 0.40 | 0.076 | $6 \times 10^7$ | 0.52 | 0.114 |
| 9 | $8 \times 10^7$ | 1.00 | 0.076 | $7.9 \times 10^7$ | 1.00 | 0.114 |
| 12 | $1.6 \times 10^7$ | — | 0.076 | $8.2 \times 10^7$ | — | 0.114 |

Figures 3, 3D, 4, 5:
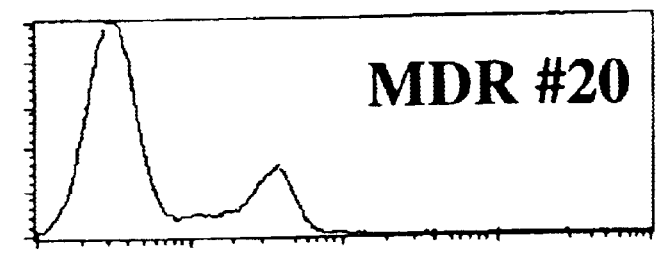
Figure 5:

Note:
On days 3 and 6 a fraction of the cells were replated while the rest were discarded. This is reflected in the fraction hind limbs volume remaining. After 12 days of expansion, 0.005 hind limb volumes were injected per mouse along with 0.25 for fresh competed marrow. The fraction at day 0 was determined by the percent of the total volume used following flushing the bone marrow from both fibias and femurs of a single mouse.
*Cell number values are those prior to cell replating Expanded stem cells are marked with MDR1 proviral DNA. To determine whether the engrafted donor cells were transduced with the MDR1 virus, secondary day 12 CFU-S were analyzed by southern blot (FIG. 5). Genomic DNA from individual CFU-S were digested with EcoR1 and probed with an MDR1 specific probe. A total of 88/88 CFU-S from 7 primary recipients (6 MDR vs. DHFR mice from competitive repopulation expt. #1, and MDR #15 from non-irradiated expt. #2) were shown to be positive by southern blot for the MDR1 provirus giving a band of the expected size (3464 bp). In addition, a subset of samples were digested with NheI which indicated the presence of the correct size full-length retroviral transcript (8580 bp). These data link the presence of the transgene and expansion of primitive stem cells.

Figure 6A:
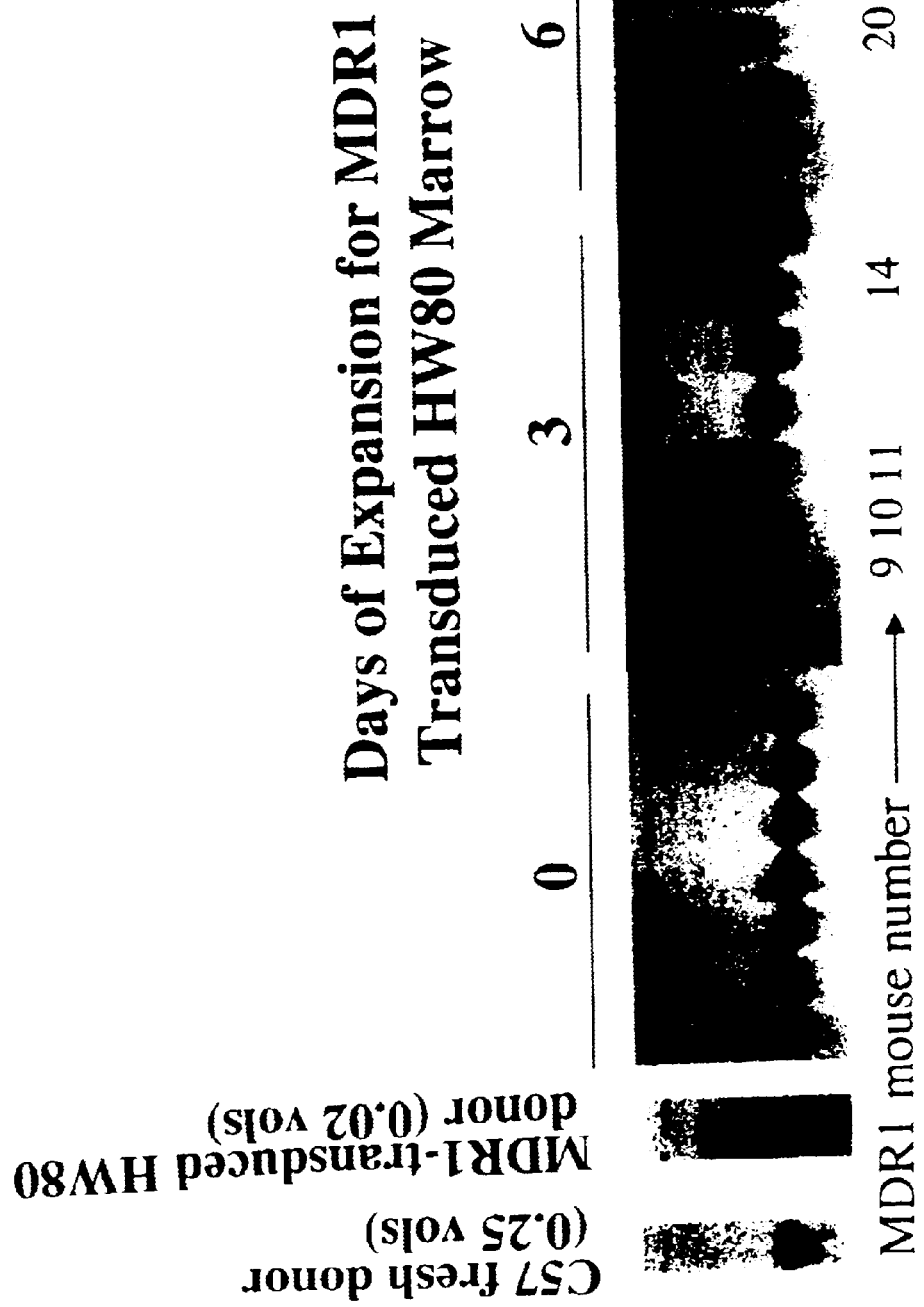
FIG. 6A shows the kinetic analysis of HaMDR1 transduced stem cell expansion. Bone marrow cells were transduced with the HaMDR-1 retrovirus and expanded for the indicated time points. HaMDR cells (0.02 vols/HW80 background) were combined with fresh competed marrow (0.25 vols/C57 background) and injected into lethally irradiated mice. Unexpanded MDR-1 bone marrow (day 0) did not out compete fresh marrow. However, expansion for 3 to 12 days resulted in a progressive increase in engraftment.

The correlation of the stem cell expansion with period of time in culture was next investigated. To determine the kinetics of stem cell expansion during culture, an additional competitive repopulation experiment was performed. For this experiment, the donor and recipient hemoglobins were switched to eliminate any possibility that engraftment was related to the donor Hb pattern. Following transduction with the MDR1 retrovirus, cells were cultured and aliquots competed at a ratio of 0.02 vol. MDR (HW80)/0.25 vol. fresh (C57) on days 0, 3, 6, and 12. Engraftment of MDR1 marrow was only seen following at least 3 days of expansion post co-culture and engraftment increased with increasing time in culture (FIG. 6A). In order to determine whether the high levels of engraftment shown in the erythroid lineage by hemoglobin electrophoresis were also maintained in other lineages, Southern blot analysis was performed on peripheral blood DNA. Blots were treated with the restriction enzyme EcoR1 and probed with a hemoglobin allele-specific probe (FIG. 6B). The results shown in FIG. 6B demonstrate that the levels of donor hemoglobin seen in the peripheral blood and the levels of lympho-myeloid reconstitution represented in the peripheral blood cell DNA are in full agreement.

In some of the transplanted mice a myeloproliferative disorder was observed providing the first evidence that overexpression of MDR1, and perhaps other ABC transporters is directly involved in leukemogenesis. Enrafted mice were therefore, analyzed serially to monitor the level of engraftment over time. In some mice, it was noticed that the peripheral white blood cell (WBC) counts began to rise to abnormal levels (FIG. 7A). Shown in FIG. 7A are 10 representative engrafted mice from the competitive repopulation experiment #2, above, 2/10 of these mice retain normal WBC counts at the present time despite a very large stem cell expansion. In most of the cases the elevation was extremely rapid and could increase by as much as 10-fold within a few days. Then, after a lag phase of 2–6 months after transplant, a number of mice developed marked peripheral blood leukocytosis, with white blood cell counts that ranged between 100,000 and 450,000 cells per 1. Analysis of Wright-stained blood smears (FIG. 7B) showed a relative increase in an abnormal cell population (bottom 2 panels relative to normal mouse in the top panel).

The disease was found to be transplantable into secondary recipients which rapidly developed the same increases in white cell counts. Analysis of the peripheral blood film showed features similar to early stage chronic myelogenous leukemia in about ⅔ of cases, with immature myeloid forms seen without an increase in blast cells (FIG. 7B). Immunophenotyping of these cells showed a high percentage of Gr-1+ and Mac1 cells. In about ⅓ of the cases, large blast-like cells were present that did not stain with any known lineage markers, giving a picture that resembled acute myelogenous leukemia (FIG. 7B). With both of these phenotypes, massive splenomegaly was invariably seen, with spleen weights ranging from 8–15 times normal size. The disease was found to be transplantable to secondary recipients, confirming that the disorder was occurring at the stem cell level.

The incidence of the myeloproliferative disorder was related both to the length of time following transplant, and to the preceding degree of stem cell expansion. In mice transplanted with freshly transduced cells, the syndrome developed relatively late after transplant and with a relatively low incidence. In contrast, mice transplanted with transduced cells that had been expanded for 12 days developed the syndrome earlier and at a higher incidence at equivalent time points. These results suggest that the robust stem cell amplification achieved during ex vivo culture accelerated the development of the myeloproliferative disorder, perhaps by increasing the risk for a second genetic mutation to be acquired during proliferation in the stem cell pool.

Replication-competent retrovirus (RCR) assays were also performed extensively on both cell lines and plasma from mice with the myeloproliferative disorder. A very sensitive PCR assay for helper virus failed to detect the helper genome but was highly positive when using positive control monkey DNA. In addition, marker rescue assays on Mus dunni cells eliminated the possibility of contamination with retroviruses of a wide host range. These data indicate that the stem cell expansion and subsequent myeloproliferative disorder are not due to a contamination of helper virus.

In addition to the elevated WBC count, the number of clonogenic progenitors in the peripheral blood and spleen increased dramatically. Typical progenitor numbers in the blood of a normal animal were 1–4/105 cells. Progenitor counts in some mice ranged from 57 to 1290/105 cells. Splenomegaly was also seen in mice with the myeloproliferative disorder. Spleen weights ranged from 483 to 834 mg compared to 106+48 mg for normal mice. The progenitor content in the spleen was concomitantly increased from a normal of 3.3–18/105 to 180/105 cells.

On the one hand, the myeloproliferative disorder is not a necessary consequence of the engraftment of the expanded gene-modified hematopoietic stem cells transduced with a nucleic acid encoding MDR1. However, on the other hand, the results disclose herein, indicate that emergence of a single, high copy number stem cell clone with relatively high degrees of MDR1 expression can be an initial step in the development of the myeloproliferative syndrome.

Importantly, despite the abnormal hematologic phenotype, the mice appeared grossly normal and healthy even with the highest white blood cell counts. Analysis of the bone marrow revealed no morphological abnormalities consistent with leukemia. In addition, the mouse karyotype was normal and there were no chromosome translocations present in peripheral blood metaphases from the two representative mice examined. These data are consistent with a prolonged period of abnormal myeloproliferation with transformation to leukemia in only a minority of mice. Peripheral blood cells from several diseased mice were also injected into SCID mice without the development of tumors. Importantly, a percentage of mice have shown large increases in stem cell content and have maintained normal hematologic parameters for as long as 9 to 14 months following transplant. The myeloproliferative syndrome can be dissociated from the hematopoietic stem cell expansion as shown by a significant number of healthy transplanted mice in which there was no evidence of myeloproliferative syndrome.

EXAMPLE 2

Enforced P-glycoprotein Pump Function in Murine Bone Marrow Cells Results in Expansion of Side Population (SP) Cells In Vitro and Repopulating Cells In Vivo Introduction The human multidrug resistance-1 (MDR1) gene product, P-glycoprotein (P-gp), is well known for its ability to confer drug resistance, however recent evidence suggests that P-gp expression can have more general effects on cellular development. The presence of transport activity in hematopoietic stem cells suggests the possibility that ABC transporters such as MDR1 could have a functional role in stem cell regulation. Further support of this hypothesis is derived from Example 1 above, which disclosed the MDR1 overexpression in murine hematopoietic stem cells. These studies showed that enforced expression of the MDR1 gene, achieved using a retroviral vector, resulted in marked expansion of repopulating stem cells during 12 days of culture in cytokine-containing media [see also Bunting et al., Blood, 92:2269–2279 (1998)]. Some mice transplanted with these cells developed a myeloproliferative syndrome phenotypically resembling chronic myelogenous leukemia, demonstrating that dysregulated P-gp expression can adversely affect hematopoietic development.

Materials and Methods

Vector constructs and producer cell lines. The HaMDR1 retroviral vector was constructed using the Harvey (Ha) murine sarcoma virus backbone as has been previously described above [see Example 1 above, and see also. Bunting et al., Blood, 92:2269–2279 (1998)]. Note that this MDR1 cDNA differs from an earlier vector [Sorrentino et al., Science, 257:99–103 (1992)] in that the sequence for codon 185 has been changed to encode for a glycine residue, and aberrant splicing sites [Sorrentino et al, Blood, 86:491–501 (1995)] have been modified by two point substitutions in the wobble positions of codons 139 and 733 [Galipeau et al., Hum. Gene Ther., 8:1773–1783 (1997)]. All ecotropic producer cell lines were generated in the GP+E86 packaging cell line [Markowitz et al., J. Virol., 62:1120–1124 (1988)] using previously described methods [Persons et al., Blood Cells Mol. Dis., 24:167–182 (1998)], and were shown to be free of replication-competent retrovirus by both PCR and marker rescue assays. The biological titer of the HaMDR1 ecotropic retrovirus was $2 \times 10^5$ particles/mil of supenatant as determined by infection of 3T3 cells and quantitation of MDR1 transduction by Rho 123 efflux and by antibody staining (see below). The HaDHFR$^{1.22Y}$ vector was used as a control, and expresses a antifolate resistant variant of the human dihydrofolate reductase gene as has been previously described [Spencer et al., Blood, 87:2579–2587 (1996)].

The "pump dead" MDR1 vector: HaMDR1Δ34 utilized a mutant MDR1 cDNA encoding a 34 amino acid deletion in the linker region between the two ATP-binding cassettes [Hrycyna et al., Biochemistry, 37:13660–13673 (1998)]. This mutant cDNA was modified to eliminate potential aberrant mRNA splicing and to encode for glycine at codon 185 as described above, and then inserted into the Harvey murine sarcoma vector backbone. A polyclonal population of ecotropic producer cells was derived by transducing GP+E86 cells with a transient supernatant derived from transfected 293T cells. Vector-transduced producer cells were then isolated by cell sorting for surface P-gp expression as described below. The 4E3 antibody staining procedure was also used to titer the polyclonal HaMDR1Δ34 vector supernatants on 3T3 cells, and showved a titer of $2 \times 10^5$ particles per ml.

4E3 antibody and Rhodamine 123 staining: Producer cells were analyzed for P-gp expression by staining with a monoclonal mouse anti-human P-glycoprotein antibody (clone 4E3, DAKO, Carpinteria, Calif.). Adherent cells were trypsinized, and resuspended in 50 ul PBS containing 2% BSA and 0.1% NaN3. 5 ul of the 4E3 antibody was then added, incubated at room temp (RT) for 30 minutes, washed twice with phosphate buffered saline (PBS), and then resuspended in 50 ul PBS cuontaining 2% BSA and 0.1% NaN3.

After the primary antibody staining, 5 ul of PE-conjugated, rabbit anti-mouse antibody (DAKO) was added as a secondary stain. The cells were then incubated at RT for 30 minutes, washed twice with PBS, resuspended in PBS for FACS analysis.

Rhodamine 123 (Rho123) staining: Rho123 staining as done by trypsinizing cells, resuspending the cells in DMEM medium containing 10% FCS at a concentration of $1 \times 10^6$ cells ml, and adding Rho 123 (Sigma) at a final concentration of 1 ug/ml. The cells were then incubated at 37° C. for one hour in the dark, washed once with 10 mls of PBS, and resuspended in DMEM/10% FCS. The cells were then incubated at 37° C. for one hour to allow for efflux, spun down, and then resuspended in 1 ml of PBS for FACS analysis.

Retroviral-mediated gene transfer into murine hematopoietic stem cells: BM cells were harvested from C57BL/6 or B6.Ch-1<b>/By (referred to as "HW80") congenic mouse strains (Jackson Laboratories, Bar Harbor, Me. ) by standard methods. Following isolation, cells were placed into liquid suspension culture in Dulbecco's Modified Eagle's Medium (DMEM) (BioWhittaker, Walkersville, Md.) with 1% penicillin/streptomycin (Gibco/BRL, Grand Island, N.Y.), 15% fetal bovine serum (FBS; Hyclone, Logan Utah), 20 ng/ml murine interleukin (IL)-3®& D Systems, Minneapolis, Minn.), 50 ng/ml human IL-6 (Amgen, Thousand Oaks, Calif.), and 50 ng/ml murine stem cell factor ® & D Systems). The cells were initially plated at $1 \times 10^6$ cells/ml in 10 mls of medium. Following pre-stimulation for 48 hours, cells were replated onto confluent monolayers of irradiated ecotropic producer cell lines. The bone marrow cells were plated at the same density used in the pre-stimulation phase and in the same medium with 6 µg/ml polybrene added. Co-culture with producer cells was continued for 48 hours followed by harvest of bone marrow cells. A small sample of bone marrow cells were plated into methylcellulose to score drug-resistant myeloid progenitors. Using the HaDHFR$^{1.22Y}$ vector, 68–71% of progenitors were resistant to trimetrexate, and using the HaMDR1 vector, 47–62% of progenitors were resistant to Taxol (n=2 for both vectors), at drug concentrations that killed 100% of control colonies.

Bone marrow expansion cultures: Expansion cultures were initiated immediately after the coculture phase of transduction, which was designated as day 0 of expansion. Non-adherent bone marrow cells were gently removed by pipetting off the medium, followed by washing the producer cells twice with 5 mls of PBS. During these steps, care was taken not to disrupt the producer cell layer. Cells were then centrifuged, media removed, and the cells were replated in suspension culture dishes at a total of $1 \times 10^7$ cells in 10 mls of medium [Bunting et al., Blood, 92:2269–2279 (1998)]. The media used for expansion was DMEM that was supplemented with 15% heat inactivated fetal calf serum, and in some experiments, with a commercially available preparation of BSA, insulin, and soluble transferrin (BIT, Stem Cell Technologies, Vancouver, Canada). The media also contained 20 ng/ml of murine IL-3, 50 ng/ml human IL-6, and 50 ng/ml murine SCF. Cells were cultured in non-treated suspension dishes (Corning, Corning, N.Y.) and grown in 5% $CO_2$ at 37° C. in a standard humidified tissue culture incubator. The cells were split on days 3, 6, and 9 and re-seeded at $1 \times 10^6$ cells/ml in 10 mls.

Hoechst 33342 SP cell assay: Murine bone marrow cells were collected and resuspended at $1 \times 10^6$ cells/ml in DMEM plus 10 mM HEPES and 2%, FBS. In a water bath, the cells were allowed to equilibrate at 37° C., followed by addition of 5 µg/ml Hoechst 33342 (Fisher Scientific, Pittsburgh, Pa.) for 90 minutes as previously described [Goodell et al., *J. Exp. Med.*, 183:1797–1806 (1996)]. Cells were then centrifuged at 4° C. and resuspended in ice cold HBSS plus 10 mM HEPES and 2% FBS at $1 \times 10^7$ cells/ml. For flow cytometric analysis or sorting, a Becton Dickinson FACS Vantage flow cytometer (Becton Dickinson, San Jose, Calif.) was configured for dual emission wavelength analysis as previously described [Goodell et al., *J. Exp. Med.*, 183:1797–1806 (1996)]. Cells were gated based on forward and side light scatter to exclude debris. For experiment 2 using the HaMDR1Δ34 vector, propidium iodide staining (2 µg/ml) was utilized to derive a gate excluding dead cells. Cells were analyzed at approximately 5,000 cells/second until data from $1 \times 10^6$ cells were collected. The SP cell gate was defined based on normal fresh C57BL/6 bone marrow cells.

Analysis of sorted Hoechst 33342 SP cells for stem cell activity: Sorted SP cells were collected in 100 ml of FBS. For limiting dilution analyses, sorted SP cells from C57BL/6 mice were mixed with $2 \times 10^5$ fresh normal bone marrow cells from congenic HW80 mice to rescue mice from lethal irradiation (1100 rads; $^{137}$Cs source). Both hemoglobin electrophoresis [Whitney, *Biochem. Genet.*, 16:667–672 (1978)] and PCR of peripheral blood leukocytes for MDR1 vector sequences were performed to assay for reconstitution in mice 16 weeks following transplant. The P7 and P8 PCR primers and conditions used have been previously described [Sorrentino et al., *Blood*, 86:491–501 (1995)].

Transplants and competitive repopulation assays: Donor bone marrow cells were mixed at the indicated ratios and injected into the tail vein of HW80 recipient mice that had been lethally irradiated with 1100 cGy using a $^{137}$Cs γ-irradiator. Peripheral blood was obtained by retro-orbital bleeding in anesthetized mice at varying time points after reconstitution and analyzed by hemoglobin electrophoresis or DNA PCR. Hemoglobin electrophoresis was performed on cellulose acetate plates as previously described [Whitney, *Biochem. Genet.*, 16:667–672 (1978)] using a commercially available kit (Helena Laboratories, Beaumont, Tex.). For PCR, genomic DNA was isolated from the circulating leukocytes present in 70 µl of blood using the InstaGene Genomic DNA kit (BioRad, Hercules, Calif.), and resuspended in 20 µl of water. One µl of the DNA solution was amplified using a commercially available kit (Qiagen Inc., Valencia, Calif.) and the following parameters (35 cycles, 94° C.×1', 60° C.×1', 72° C.×1'. The PCR primers used to amplify fragments from the HaMDR1 and HaMDR1Δ34 vectors were as follows:

5' CCACGTCAGCCTTGGACACA 3' (SEQ ID NO:15)

5' GCCGCTTGGTGAGGATCTCT 3' (SEQ ID NO:16)

Results

The goal of the present example study was to further explore the effect of MDR1 gene expression on stem cell development. Considering the link between Side Population (SP) stem cells and transporter function, it was initially asked whether MDR1-mediated stem cell expansion was associated with an increase in SP stem cells in expansion cultures. It was also determined whether stem cell expansion was limited to ex vivo culture conditions. For instance, the mechanism of stem cell expansion could be due to efflux of some media component that had negative effects on stem cell proliferation. An alternative and more interesting possibility is that MDR1 gene expression could be acting at a more global level that is independent of ex vivo culture conditions. To distinguish between these possibilities, it was determined as to whether freshly transduced stem cells would have a direct proliferative advantage in vivo after transplantation. In addition, experiments were performed to determine whether these stem cell effects required the efflux-pump activity of P-gp, or whether the effects could be due to other properties of the experimental system. A vector encoding an expressed but functionally dead P-gp was tested in both the SP cell expansion assay and in vitro competitive repopulation assays. Altogether, these studies provide further evidence that enforced ABC transporter function can alter the proliferative and developmental fate of hematopoietic stem cells.

Figure 8:
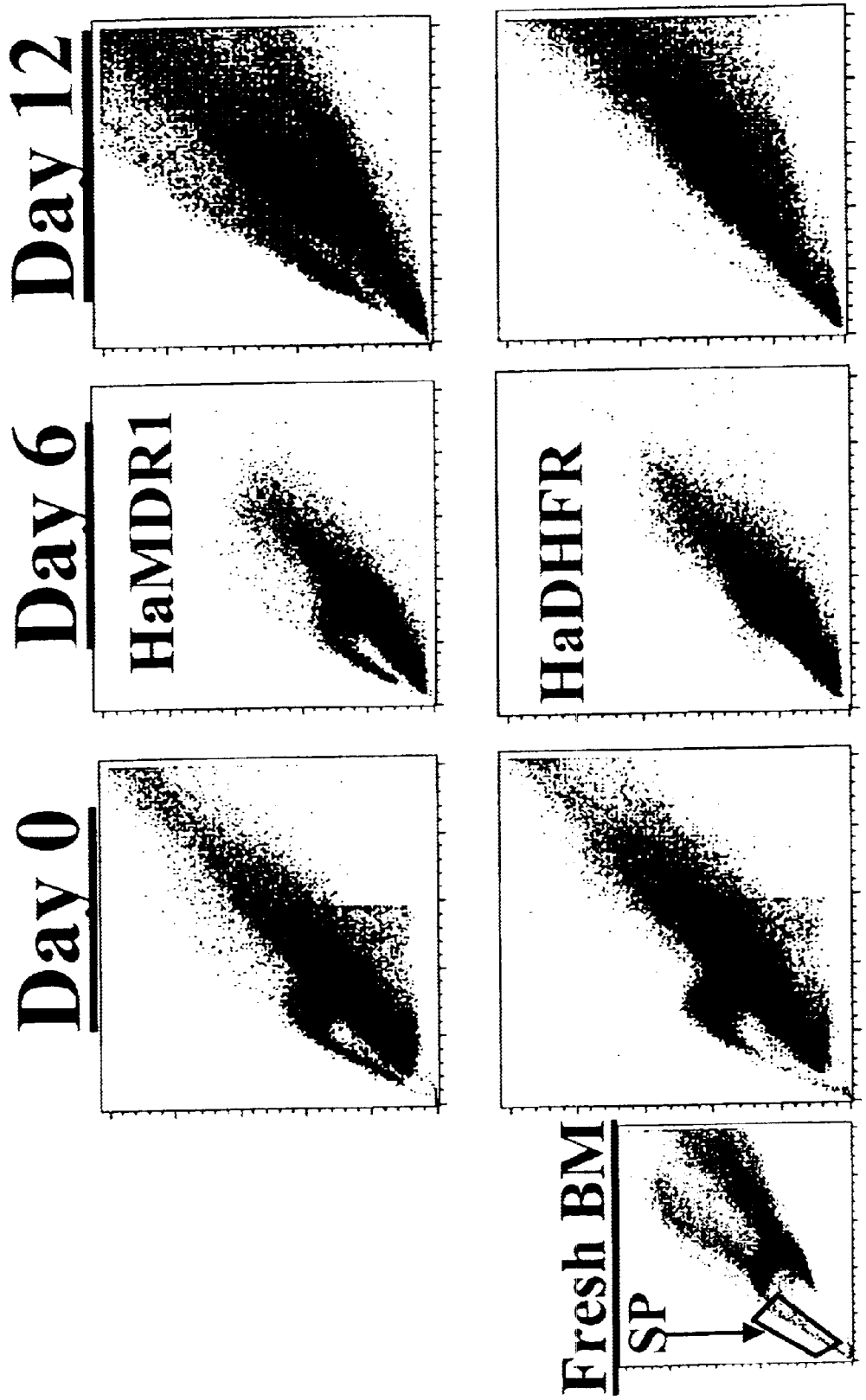
FIG. 8 shows the quantitation of Hoechst 33342 SP cells in hone marrow expansion cultures following MDR1 gene transfer. Murine bone marrow cells were prestimulated for 48 hours in the presence of growth factors and then retrovirally transduced with either the HaMDR1 or HaDHFR$^{L22Y}$ vector for another 48 hours. The time point immediately following co-culture was defined as day 0 of expansion. Transduced cells were then grown in suspension cultures for 12 days. Hoechst 33342 staining of BM cells was performed on dav 0, 6, and 12 to determine the frequency of SP cells within the expanding cell populations. FACS profiles representative of 3 independent expansion experiments are shown for BM cells transduced with either the HAMDR1 (top panels) or HaDHFR$^{L22Y}$ vectors (bottom panels). On the left, a sample of normal, freshly isolated C57BL/6 BM cells is shown with the SP gate indicated.

Expansion of MDR1-transduced SP cells during ex vivo culture: To determine whether enforced P-gp expression would result in an increase in SP cell numbers during ex vivo expansion cultures, murine BM cells were transduced with the HaMDR1 retroviral vector [Example 1, above; Bunting et al., *Blood*, 92:2269–2279 (1998)] and then cultured for 12 additional days in media containing fetal calf serum, IL-3, IL-6, and SCF. As a control, cells were transduced with a vector expressing a human dihydrofolate reductase gene (HaDHFR-$^{1.22Y}$) within the same vector backbone [Spencer et al., *Blood*, 87:2579–2587 (1996)]. SP cells were quantitated by Hoechst 33342 staining and flow cytometry after 0, 6, or 12 days of culture (FIG. 8). In populations of cells transduced with the HaDHFR$^{1.22Y}$ vector, a loss of cells in the lower part of the SP tail, corresponding to stem cells with long-term repopulating activity [Goodell et al., *Nat. Med.*, 3:1337–1345 (1997)], had already occurred immediately following the transduction procedure (day 0). After an additional 6 days of expansion, SP cells were no longer detectable in these control cultures. In contrast, cultures of cells that were transduced with the HaMDR1 vector showed preservation of SP cell numbers at early time points, with an increase in the absolute number of SP cells averaging 187-fold (n=3, standard error 161, range 38–380 fold) after 12 days of ex vivo culture. These data show that while SP cells were lost over time in extended bone marrow cultures, enforced expression of the MDR1 gene resulted in a large amplification of SP cells over a 12-day time period.

Repopulatating activity in 12 day-expanded, sorted SP cells. To determine if repopulating cells were present and enriched within the expanded SP population, limiting dilution transplant experiments were performed in irradiated mice using sorted SP cells. Control experiments with normal, fresh BM cells showed reconstitution with SP cell doses as low as 250 cells, consistent with previously reported values [Goodell et al., *J. Exp. Med.* 183:1797–1806 (1996)]. The repopulating cell frequency in the MDR1-transduced SP cell population was determined by transducing C5BL/6 BM cells with the HaMDR1 vector, expanding transduced cells for 12 days, and then sorting for SP cells by flow cytometry. These sorted SP cells were injected into lethally-irradiated recipient mice along with $2 \times 10^5$ fresh bone marrow cells (HW80 background), the latter used to confer radioprotection to the mice. Reconstitution analysis was done 16 weeks after transplant using a PCR assay to detect HaMDR1 vector sequences in total peripheral blood leukocyte DNA. Reconstitution was also studied using hemoglobin electrophoresis to determine the relative erythroid contributions arising from sorted SP cells.

Figure 9B:
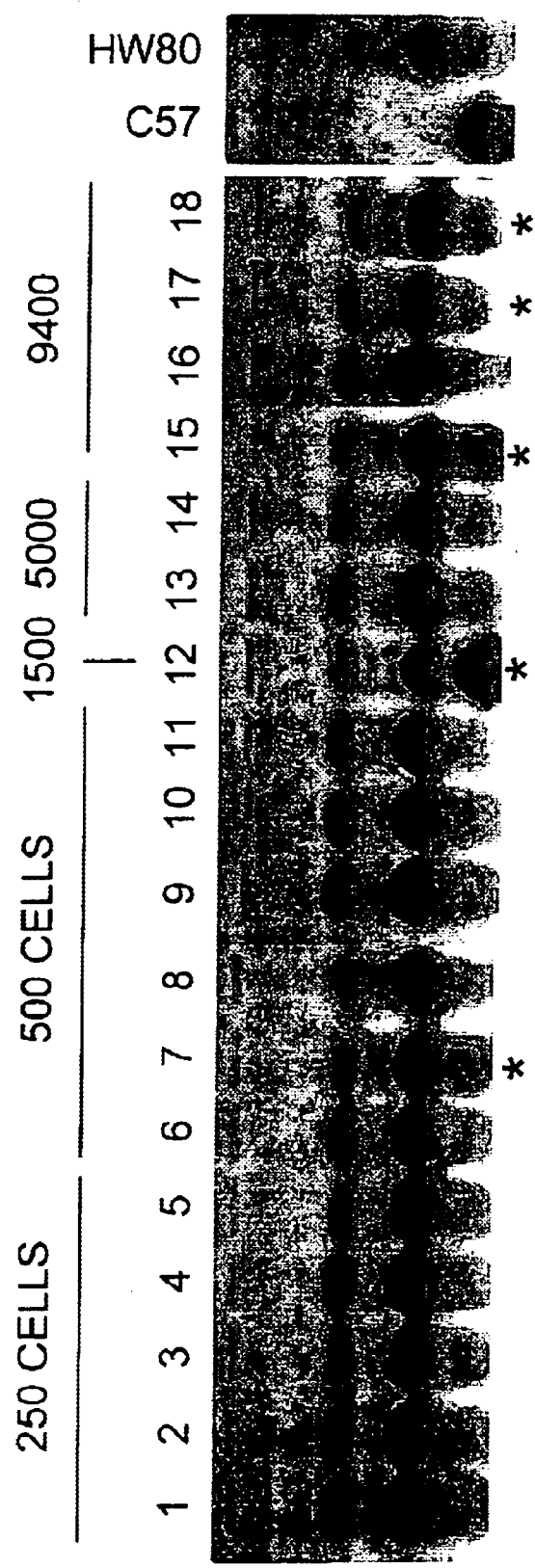

The PCR assay showed repopulation of recipient mice with SP cell doses as low as 500 cells, and vector-marked cells were present in the majority of mice receiving between 1500–9400 expanded SP cells (FIG. 9A). In most of these cases, the hemoglobin electrophoresis also showed contributions from the expanded SP cells derived from the C57BL/6 background, however the percent contribution was very low in the majority of mice (FIG. 9B). These data suggest that the expanded SP cell population may be somewhat enriched for repopulating cells relative to whole bone marrow, but that the frequency of repopulating cells in the expanded SP population is significantly less than that in fresh SP cells from normal bone marrow. The low degrees of chimerism for the expanded SP cells could reflect a limited repopulation capacity of the expanded cells, or simply a greater number of stem cells in the fresh HW80 graft used to provide radioprotection. This relative decrease in the concentration of repopulating cells in the expanded SP population suggests that a significant proportion of the expansion is due to a phenotypic change in the cells without a corresponding change in repopulation potential. This interpretation is consistent with previous results showing that the absolute numbers of functionally-defined repopulating cells increased 12–30 fold in MDR1-transduced whole bone cultures [Example 1 above; Bunting et al., *Blood*, 92:2269–2279 (1998)], while in this study, the absolute number of SP cells increased about 180 fold during the same culture period.

Expansion of MDR1-transduced stem cells in vivo. To determine whether the MDR1 vector wvas having a direct effect on stem cell proliferation, or whether the effect was specific to ex vivo expansion cultures, it was determined as to whether MDR1-mediated stem cell expansion would also occur directly in vivo. BM cells were transduced with either the HaMDR1 or the HaDHFR$^{1.22Y}$ vector, and these grafts were mixed immediately after transduction for competitive repopulation experiments. C57BL/6 BM cells were transduced with the HaMDR1 vector, and HW80 BM cells were transduced with the HaDHFR$^{1.22Y}$ vector. After transduction, equal donor volumes from each graft were mixed and transplanted into lethally irradiated recipient mice. Mice received between 2.3–5.1×10$^6$ HaDHFR$^{1.22Y}$-transduced cells, and between 1.8–2.5×10$^6$ HaMDR1-transduced cells. In one experiment, the recipient mice were divided into two cohorts. One group of mice received two 5-day courses of granulocyte colony-stimulating factor (G-CSF)/stem cell factor (SCF) growth factor treatment on weeks 5 and 8 following transplant as has been described [Bodine et al., *Blood*, 88:89–97 (1996)], and one group of mice was left untreated. Because treatment with these growth factors is known to cause a significant increase in stem cell content in vivo [Bodine et al., *Blood*, 88:89–97 (1996)], the treated mice might show an earlier outgrowth of the MDR1-transduced graft.

Figure 10A:
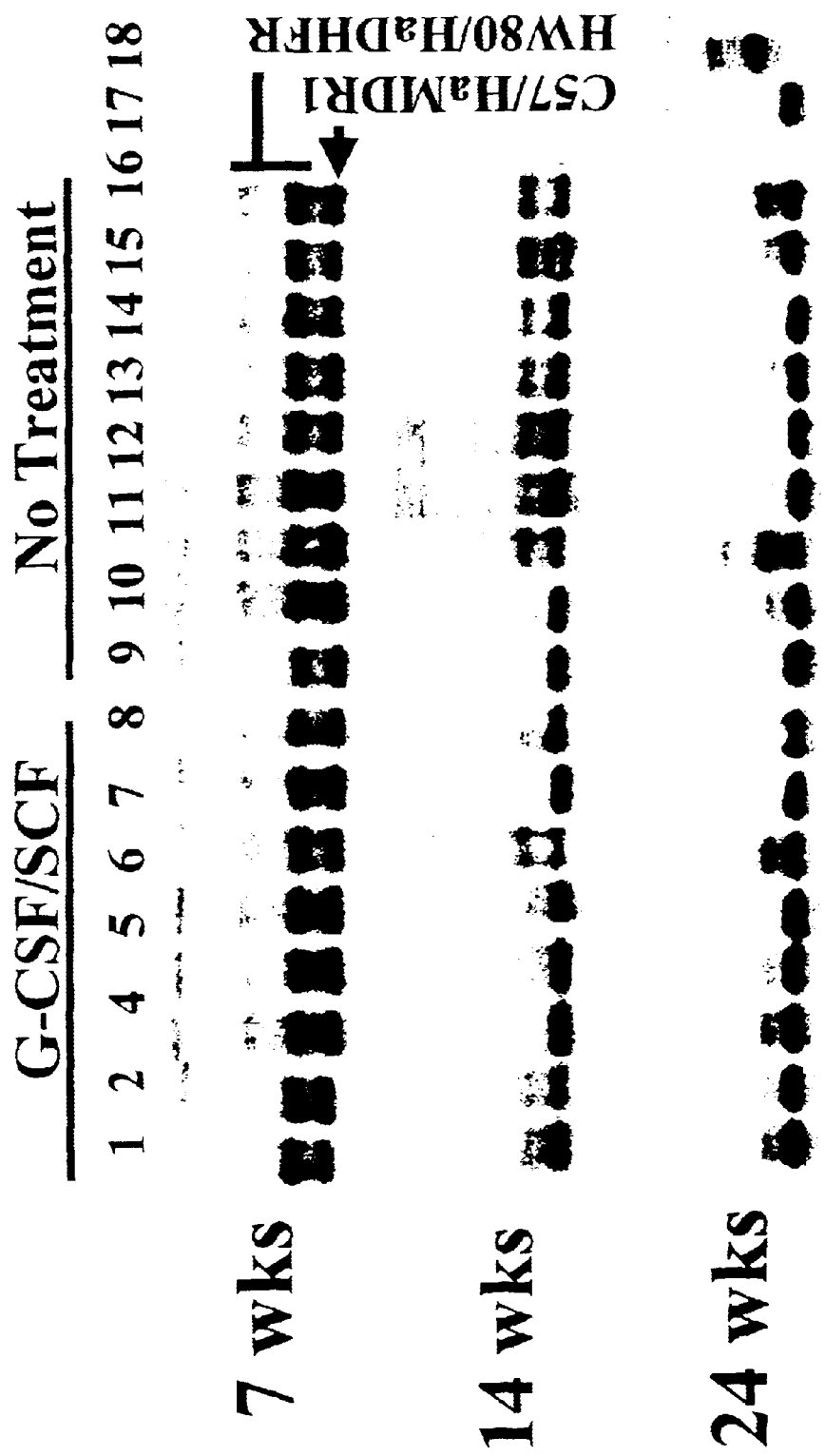
FIGS. 10A–10C show the results of the competitive repopulation assay in mice transplanted with equal donor volumes of HaMDR1- and HaDHFR$^{L22Y}$-transduced BM cells. BM cells from C57BL/6 mice were transduced with the HaMDR1 vector, and HW80 marrow cells with the HaDHFR$^{L22Y}$ vector. Immediately after the transduction, equal donor volumes from each transduced graft were mixed and transplanted into lethally-irradiated recipient mice. Engraftment was monitored by tracking the proportion of donor hemoglobin specific for either the HaMDR1—(lower band) or HaDHFR$^{L22Y}$—(upper two bands) transduced cells. Hemoglobin electrophoresis gels are shown in FIG. 10A for mice from expt. #2, obtained at 7, 14, and 24 weeks following transplant. These mice were divided into two groups, one receiving two 5-day courses of G-CSF/SCF treatment (left) and one untreated group (right). Each lane represents a sample from a single mouse. The hemoglobin pattern for the C57BL/6 and HW80 controls are shown on the right. Two independent mixing experiments were performed and the data for both of these are graphically shown in FIGS. 10B–10C. The y-axis represents the percentage of donor engraftment with MDR1-transduced cells as indicated by hemoglobin electrophoresis. Each line represents an individual mouse analyzed serially over time.
Figures 10B, 10C:
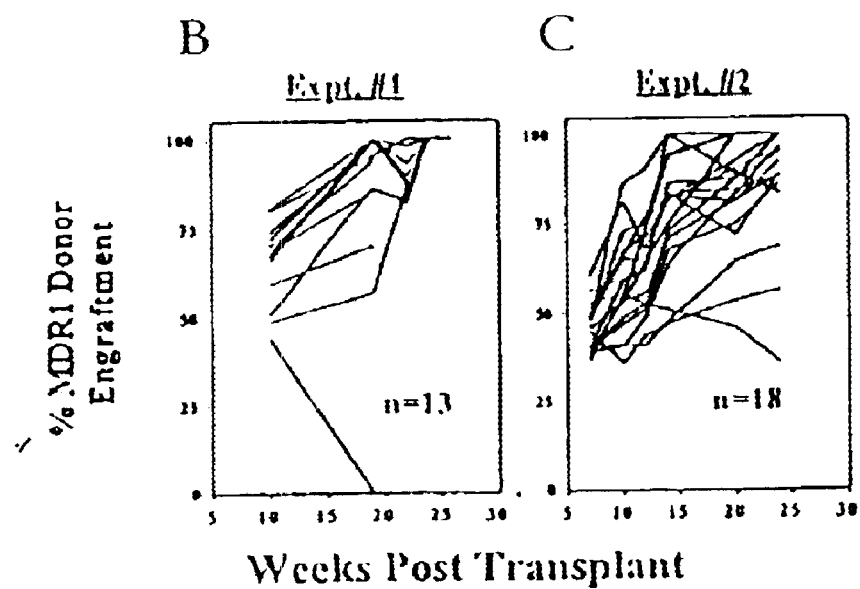

At 7 weeks following transplant, hemoglobin reconstitution patterns uniformly reflected the input ratio of the grafts, with a roughly 50/50 mix of the two hemoglobin patterns (FIG. 10A). At later time points, mice from both groups showed a gradual increase in the proportion of erythroid cells derived from the MDR1-transduced graft. At 14 weeks after transplant, the cytokind-treated group showted increased proportions of cells from the MDR1-transduced graft relative to the untreated group, but this did not reach statistical significance (p=0.094). At 24 weeks this difference was no longer apparent, and the MDR1-transduced BM graft had completely overtaken the control graft in most cases. Data from two independent experiments are graphically shown in FIGS. 10B–10C. The majority of mice showed a large and progressive shift towards MDR1-transduced donor cell engraftment over time. These experiments demonstrate that the capacity of MDR1 vectors to expand stem cells is not limited to the 12-day culture protocol.

Figure 11:
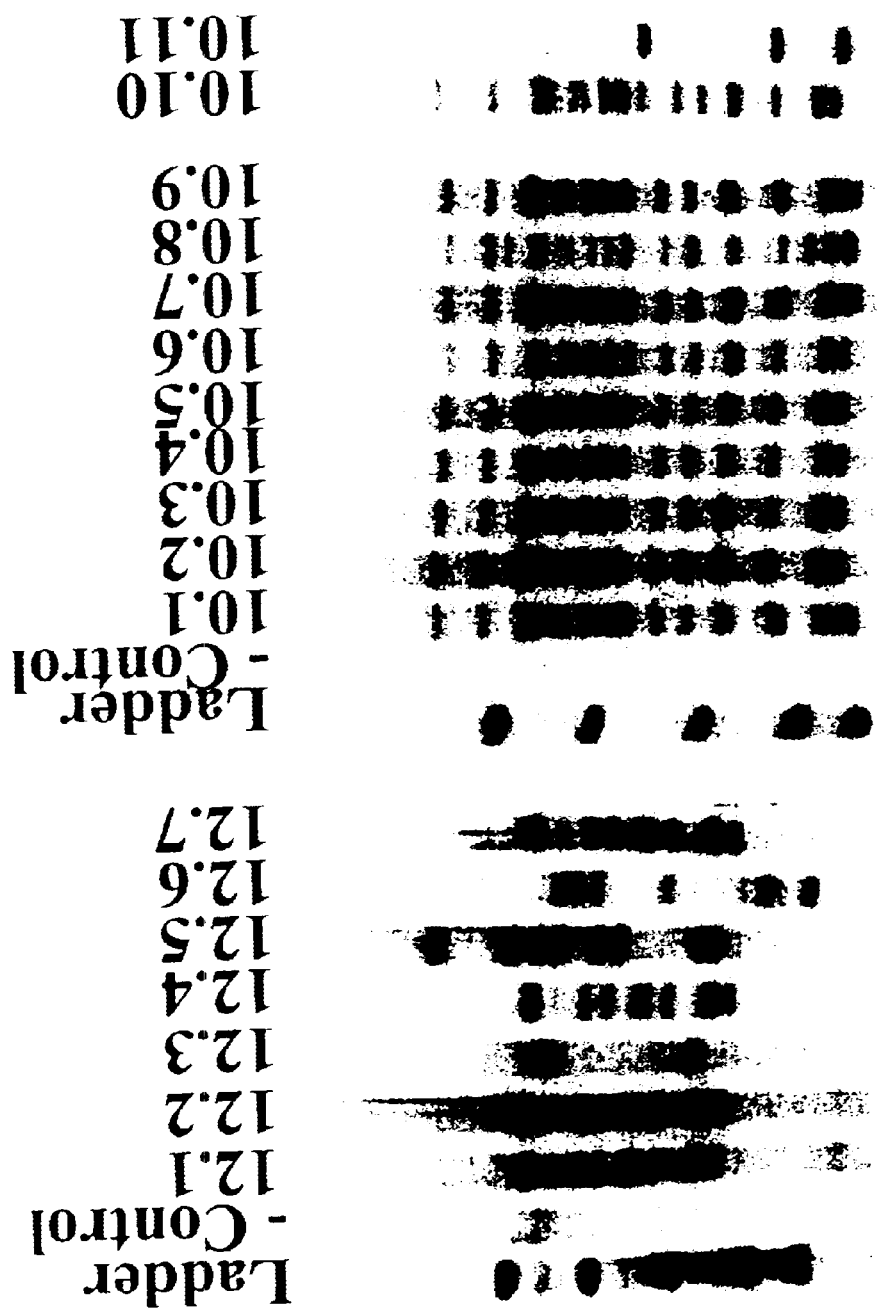
FIG. 11 depicts the clonality analysis of secondary CFU-S from mice transplanted with HaMDR1-transduced BM cells. Two mice from mixing experiment #1 were killed 24 and 20 weeks after transplant, and bone marrow-derived CFU-S colonies were harvested 12 days after injection into irradiated mice. DNA was prepared trom each CFU-S colony and analyzed for vector integration sites by Southern blot analysis. Because the probe is upstream of the 5' EcoRI site in the vector, each band represents a unique integration site within a CFU-S clone. The left panel shows the analysis of 7 clones derived from mouse #12, and the right panel shows 11 clones from mouse #10. DNA from a normal spleen (control) shows a faint endogenous band hybridizing with the MDR1 probe fragment. The DNA ladder is shown on each gel and the ladder marker sizes are indicated on the left. The small arrows in the right panel indicate unique retroviral integration sites in a parent stem cell clone.
Figures 12A, 12B, 12C, 12D:
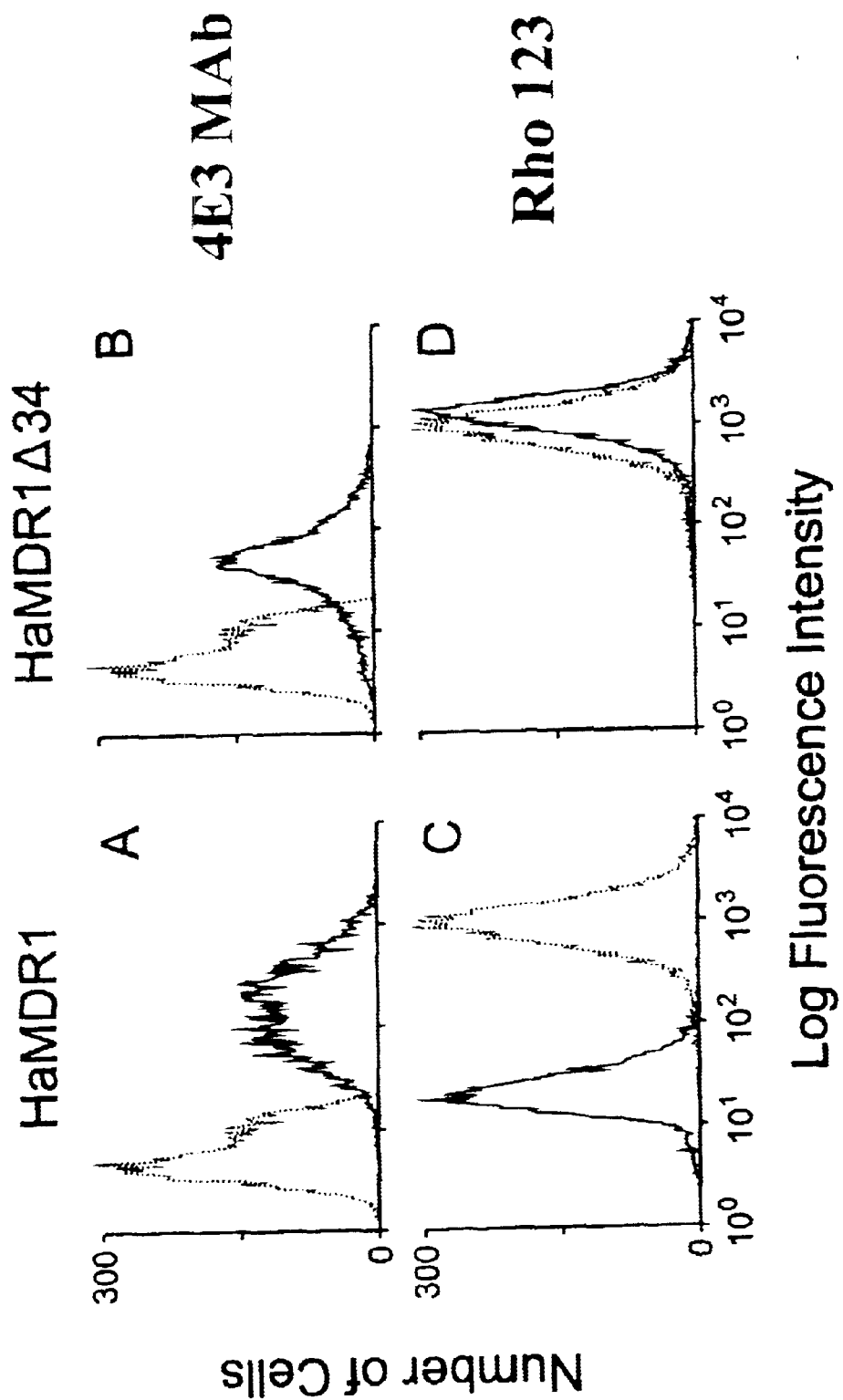
FIGS. 12A–12D depict the P-gp expression and function in producer cells transduced with the HaMDR1Δ34 vector. The monoclonal antibody 4E3 was used to detect cell surface expression of P-gp in GP-E86 cells transduced with the HaMDR1 vector in FIG. 12A or with the HaMDR1Δ34 vector in FIG. 12B. The heavy line represents results from the producer cell lines, while the lighter lines show negative controls using untransduced GP-E86 cells. Molecular pump function was also assayed in these cells using a Rhodamine exclusion assay (HaMDR1 in FIG. 12C, and HaMDR1Δ34 in FIG. 12D). The presence of cells with low fluorescence indicates rhodamine efflux activity due to P-gp expression. Again, the light lines are untransduced negative controls.

Clonality and copy number in transduced stem cell clones. It was next determined if the outgrowth of MDR1-transduced cells in vivo was due to polyclonal stem cell expansion. Six of the primary transplant recipients from expt.#1 were killed 20 to 26 weeks following transplant and the BM cells were injected into irradiated secondary recipients. Day 12 CFU-S colonies were then isolated and DNA was analyzed by Southern blotting for MDR1-vector integration sites. FIG. 11 shows two representative Southern blots showing the range of clonality observed in these mice. Mouse #12 showed 4 unique integration patterns within 7 individual CFU-S, indicating that hematopoiesis was polyclonal at a time when MDR1-transduced stem cells had expanded and outcompeted the control graft. It was noted that there was an increased number of clones with relatively high vector copy numbers (12.1, 0.2, 0.4. 0.5, and 0.7) versus low copy numbers (12.3 and 0.6). Mouse #10 showed oligoclonal hematopoiesis where all clones but one (10.11) show a highly uniform banding pattern with very high copy number (18 integrants). Some stem cell clones in mouse #10 showed unique integrations (arrows) in addition to the common integration sites. This is most likely due to self-renewing stem cell divisions that occurred during the 48-hour transduction period. Of the 6 primary mice that were analyzed, 3 showed polyclonal stem cell patterns, 1 was oligoclonal, and 2 showed a monoclonal pattern. The increased proportion of clones with relatively high copy numbers may reflect a proliferative advantage for stem cell clones with relatively high levels of P-gp expression.

Figure 13A:
FIGS. 13A–13B show the transduction efficiency of vectors in primary CFU-S. Whole bone marrow cells were transduced either with the HaMDR1Δ34 vector (FIG. 13A, top), or the HaMDR1 vector (FIG. 13B, bottom). The cells were then injected into irradiated recipients, and DNA was later prepared from day 14 CFU-S colonies. Southern blot analysis was performed to detect the proviral genome by digesting with EcoRI and probing with a full-length MDR1 cDNA. Each lane represents a sample from an individual colony. The lane marked by an asterisk is from an untransduced CFU-S colony, which serves as a negative control.
Figure 13B:

The development of a functionally inactivated MDR1 vector. It was next determined as to whether the expansion of SP cells and repopulating cells required the efflux-pump function of P-gp. A vector was constructed (HaMDR1Δ34) that was otherwise identical to HaMDR1 except for a coding region deletion resulting in loss of 34 amino acids in the linker region between the two ATP hydrolysis sites. As originally described [Hrycyna et al., *Biochemistry*, 37:13660–13673 (1998)], this mutant MDR1 cDNA expresses P-gp on the cell surface at relatively normal levels, but the mutant protein cannot act as an efflux pump. As expected, producer cells expressing the HaMDR1Δ34 vector had relatively high levels of P-gp expressed on the cell surface as detected by flow cytometry using the monoclonal antibody 4E3, but lacked the ability to efflux the P-gp substrate Rho 123 (FIGS. 12A–12D). The ability of the HaMDR1Δ34 vector to transduce early bone marrow cells was compared with the HaMDR1 vector by evaluating the transduction frequency of the two vectors in primary CRU-S. This analysis showed that the HaMDR1Δ34 vector was highly efficient at transducing CFU-S, and had a titer at least equivalent to the wild type HaMDR1 vector (FIGS. 13A–13B).

Figure 14A:
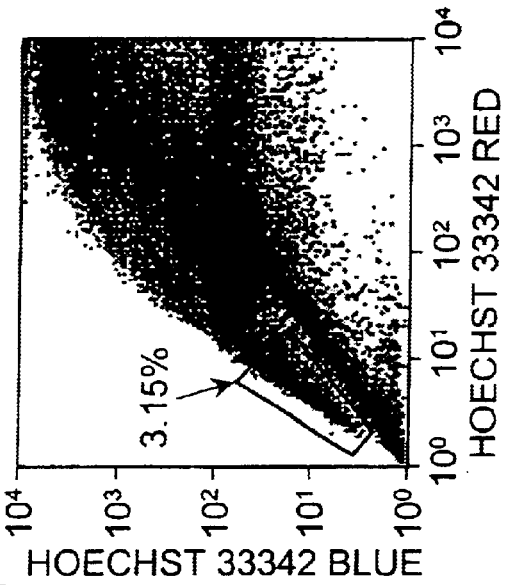
FIGS. 14A–14D depict the quantitation of SP cell expansion in cultures of cells transduced with the HaMDR1Δ34 vector. BM cells were transduced with either the HaMDR1Δ34 (in FIGS. 14A and 14C) or the HaMDR1 vector (14B and 14D), and then expanded in suspension cultures tor the indicated time periods.
Figure 14B:
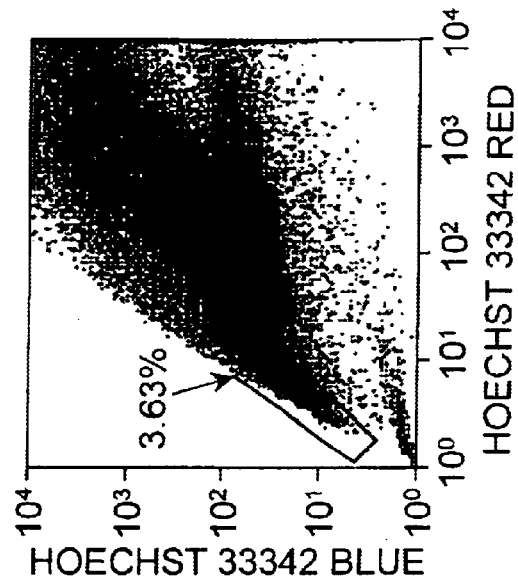
Figure 14C:
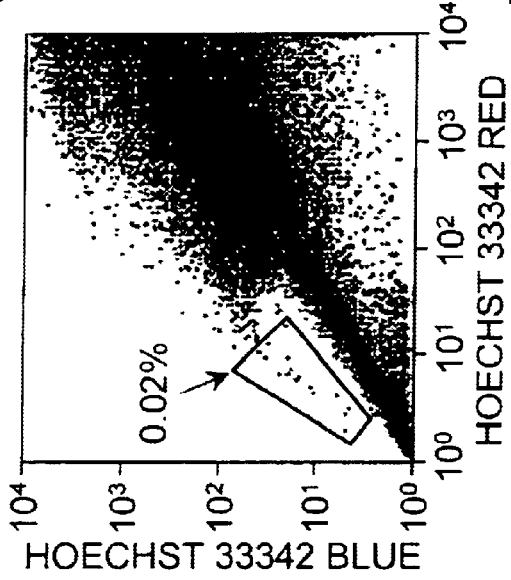
Figure 14D:
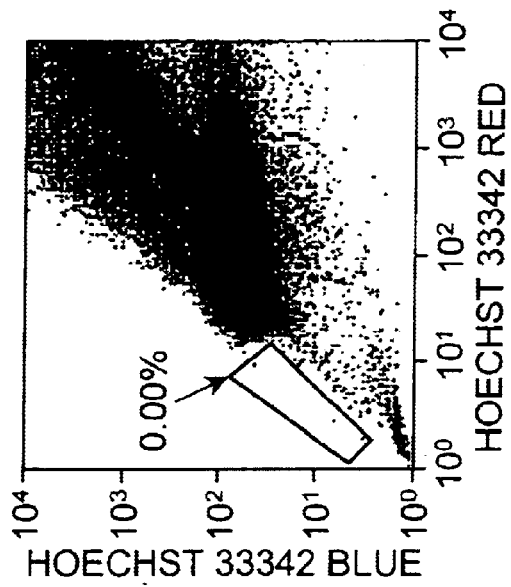

The requirement of P-gp pump function for SP cell expansion in vitro. In two separate experiments, bone marrow cells were transduced with the HaMDR1Δ34 vector, expanded in culture, and analyzed at various time points for changes in the number of SP cells. The first experiment was analyzed after 7 days of culture, and showed no SP cell expansion in cultures transduced with the HaMDR1Δ34 vector, while there was a marked expansion of SP cells using the HaMDR1 vector (compare FIGS. 14A and 14B). A second experiment showed a complete lack of SP cells in cultures transduced with the HaMDR1Δ34 vector and expanded for 13 days (compare FIGS. 14C and 14D). These experiments demonstrate that P-gp pump function was required for expansion of SP cells in culture.

Figure 15A:
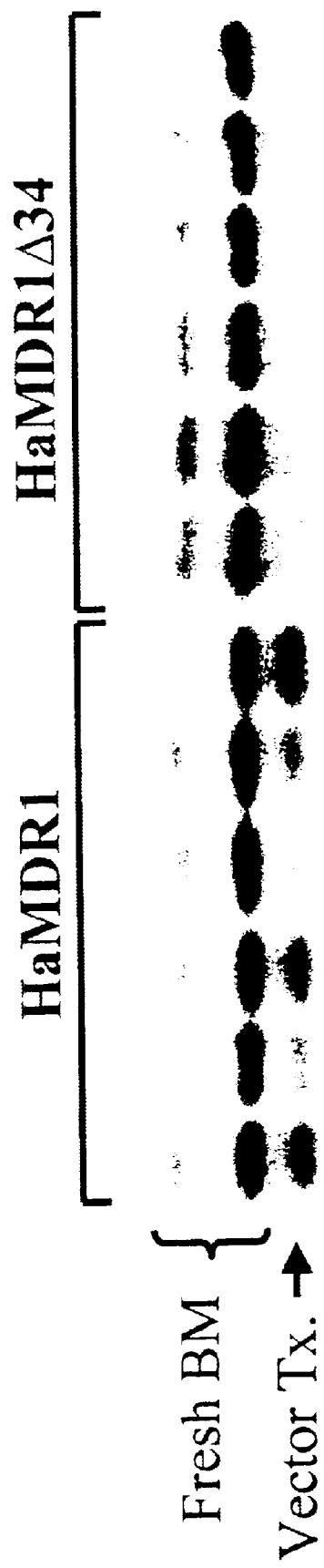
FIGS. 15A–15B show the competitive repopulation studies using cells transduced with the HaMDR1Δ34 vector.

The requirement of pump function for expansion of repopulating cells. The HaMDR1Δ34 vector was next evaluated in competitive repopulation experiments to determine if P-gp pump function was required for expansion of repopulating cells. Bone marrow from C57BL/6 mice was transduced with either the HaMDR1Δ34 or HaMDR1 vector, and then expanded in culture for 12 days. In one experiment, the expanded cells were competed against fresh bone marrow cells from HW80 mice. The input ratio used was 0.02 femur volumes of transduced, expanded marrow to 0.25 femur volumes of fresh HW80 marrow. Sixteen weeks after transplant, the recipient mice were analyzed by hemoglobin electrophoresis. All 6 mice transplanted with HaMDR1 transduced cells showed significant contributions from the transduced graft (FIG. 15A), despite the low input ratio of transduced cells. In contrast, there was no detectable donor contribution from the HaMDR1Δ34 transduced graft in any of the six mice that received HaMDRA1Δ34-tranisduced and expanded cells along with fresh bone marrow cells.

Figure 15B:
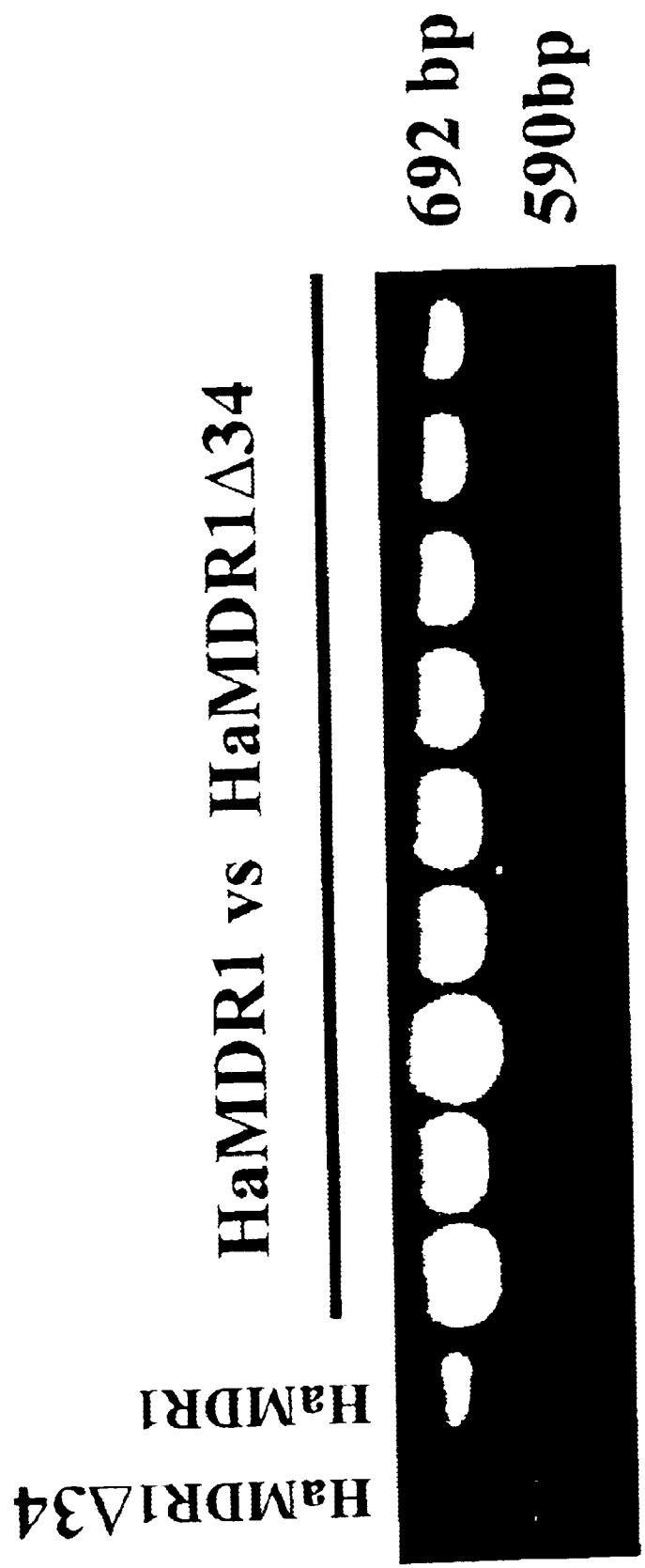

In addition, both transduced grafts were directly competed by transfusing equal volumes of each graft into irradiated recipients, and then using PCR to evaluate the relative contributions to engraftment in peripheral blood leukocytes. PCR primers were developed that flanked the 34 amino acid deletion, and therefore could co-amplify products of two different sizes from the HaMDR1 and HaMDR1Δ34 vectors (692 and 590 bp respectively). In 9 mice from two independent experiments, there was no detectable contribution from the HaMDR1Δ34 vector, while HaMDR1-transduced cells were readily detected (FIG. 15B). The presence of the HaMDR1Δ34-amplification product was easily detected in mice transplanted solely with unexpanded, transduced cells, ruling out a lack of stem cell transduction with HaMDR1Δ34 as the explanation for the competition result.

Myeloproliferative disorder in transplanted mice. Recipients of en vivo expanded HaMDR1-transduced BM cells developed a myeloproliferative disease [Example 1 above; Bunting et al., Blood, 92:2269–2279 (1998)]. In this study, the peripheral white blood cell counts of transplanted mice were analyzed at varying times following transplantation, looking for the characteristic leukocytosis that is associated with the myeloproliferative syndrome. In the two groups of mice transplanted with freshly transduced HaMDR1-transduced cells, 3/13 and 1/18 showed leukocyte counts greater than 20,000 cells/ul at 24 and 26 weeks post-transplant respectively. In contrast, in Example 1, above [see also Bunting et al., Blood, 92:2269–2279 (1998)] which used cells expanded for 12 days in vitro, leukocytosis was observed in 21/24 and 7/7 mice at 25 and 27 weeks respectively. The 4 mice transplanted exclusively with HaMDR1Δ34-transduced bone marrow cells have been followed for 15 weeks. and none have shown leukocytosis or any other abnormalities.

Discussion

Although it is well known that the MDR1 gene is expressed in primitive human hematopoietic cells [Chaudhary and Roninson, Cell, 66:85–94 (1991)], the functional importance of MDR1 gene expression has not been defined. There are several lines of evidence suggesting that expression of the MDR1 gene, or perhaps other ABC transporters, has an important functional role in stem cells. Repopulating stem cells from a variety of species can be purified based on their ability to exclude fluorescent dyes, a property at least partially attributable to transporter expression. This conservation of transporter expression in stem cells is consistent with an important functional effect. A more direct line of evidence comes from Example 1, above which shows that enforced expression of the MDR1 gene resulted in marked amplification of murine stem cells over a 12-day culture period [see also Bunting et al., Blood, 92:2269–2279 (1998)]. The data presented here confirm and extend that disclosed in Example 1 above, and provide further support for the concept that MDR1 transporter function can influence the replicative behavior of stem cells.

An intriguing link between MDR1 expression and normal stem cell function has been the identification of the SP stem cell phenotype. SP stem cells are found in the bone marrow from multiple mammalian species and express low to undetectable levels of the CD34 antigen [Goodell et al., Nat. Med., 3:1337–1345 (1997)], indicating that they may contain the primitive CD34-negative stem cells that have been recently described in xenograft transplantation experiments [Bhatia et al., Nat. Med., 4:1038–1045 (1998) and Zanjani et al., Exp. Hematol., 26:353–360 (1998)]. Because the SP phenotype can be abrogated with verapamil, a known inhibitor of P-gp, it has been suggested that the SP phenotype may be due to expression of the MDR1 gene, or perhaps another ABC transporter [Goodell et al., J. Exp. Med., 183:1797–1806 (1996)]. Results from experiments disclose herein demonstrate that enforced MDR1 expression resulted in a large amplification of SP stem cells in culture. These data strengthen the functional link between the SP stem cell phenotype and MDR1 gene expression. One possible mechanism for the MDR1-mediated expansion of stem cells is through a reduction of apoptosis in the cultures. CD34+ heniatopoietic cells normally undergo apoptosis during ex vivo expansion cultures [Traycuff et. al., Exp. Hematol., 26:53–62 (1998)]. It has recently been shown that P-gp can inhibit apoptosis in cultured hematopoietic cells [Johnstone et al., Blood, 93:1075–1085 (1999)], as well as in other cellular systems [Smyth et al., Proc.Natl.Acad.Sci.USA, 95:7024–7029 (1998); Robinson et al., Biochemistry, 36:11169–11178 (1997); and Gruol and Bourgeois, Biochem. Cell Biol., 72:561–571(1994)].

In contrast, when DHFR-transduced control cells were cultured, SP stem cells were proressively lost over time. This loss of SP cells correlates with the known loss of repopulating stem cells with extended culture periods [Bhiatia et al., J. Exp. Med., 186:619–624 (1997); Tisdale et al., Blood, 92:1131–1141 (1998); and Shimizu et. al., Blood, 91:3688–3692 (1998)]. Deleterious effects on SP stem cells were even noted in control cultures immediately after the 4-day transduction period. The relative loss of long term repopulating stem cells during transduction with the DHFR control vector may in part explain the difficulty in obtaining durable gene marking in large animal models. Culture conditions have recently been identified that minimize the loss and differentiation of repopulating stem cells [Bhatia et al., J. Exp. Med., 186:619–624 (1997) and Glimm and Eaves, Blood, 94:2161–2168 (1999)], and it may be that these methods result in a relative preservation of SP stem cells.

To determine if MDR1-mediated stem cell amplification was restricted to the setting of ex vivo expansion cultures, it was determined whether freshly transduced cells would have a direct competitive advantage in vivo after transplantation. These experiments showed a large selective advantage for the HaMDR1-transduced cells that progressively emerged in transplanted mice over a 6 month time frame. Although it is theoretically possible that some of the observed stem cell expansion may have occurred during the 2 day transduction period, previous results showed very little amplification of repopulating cells at day 0 [Example 1 above; Bunting et al., Blood, 92:2269–2279 (1998)]. Furthermore, the slow emergence of the MDR1-transduced graft over 24 weeks is most consistent with a direct proliferative advantage in vivo. These data indicate that MDR1 expression is modulating an endogenous stem cell substrate in vivo, rather than simply extruding some component present within the ex vivo culture media. In the secondary CFU-S experiments, most stem cell clones were observed to have relatively high copy number of the MDR1 vector (8–18 copies). The degree of amplification seen in a given stem cell clone may be directly related to the level of expression of P-gp, consistent with the correlation between copy number and expansion.

Prior to this study, one important mechanistic question was whether the pump function of P-gp was necessary for stem cell expansion. If the pump function were not required, amplification would be due to direct membrane effects from P-gp, or due to some artifacts of the retroviral transduction system. Using a vector that expresses a functionally inactive P-gp demonstrates that pulp function is required for both expansion of SP cells in vitro, and expansion of repopulating cells in vivo. These findings show that the observed stem cell effects are due to redistribution of a critical substrate within stem cells.

Some mice transplanted with MDR1-transduced cells developed a myeloproliferative syndrome characterized by high white blood cell counts, immature myeloid cells in the peripheral circulation, and splenomegaly; resulting in a syndrome that phenotypically resembles chronic myelogenous leukemia. This syndrome occurred with a decreased incidence and a longer latency period compared to historical controls [Example 1 above; Bunting et al., *Blood*, 92:2269–2279 (1998)] that were transplanted with ex vivo expanded, MDR1-transduced cells. This comparison indicates that the rate of development of the syndrome is related to the prior degree of stem cell expansion, perhaps by increasing the probability of a second genetic event required for transformation. In earlier studies of MDR1 transfer into murine stem cells [Sorrentino et al., *Science*, 257:99–103 (1992); Podda et al., *Proc Natl.Acad Sci USA* 89:9676–9680 (1992); Hanania et al., *Gene Ther.*, 2:279–284(1995)], the development of a myeloproliferative syndrome was not reported. One possible explanation for this discrepancy is differences in the vectors used in the earlier studies. The vector used in our stem cell expansion experiments has been modified to reduce cryptic mRNA splicing within the MDR1 coding sequence [Sorrentino et al., *Blood*, 86:491–501 (1995); Galipeau et al., *Hum. Gene Ther.*, 8:1773–1783 (1997)], and expresses greater amounts of P-gp than the vectors used in the previous studies.

The relationship between MDR1 gene expression and the occurrence of a myeloproliferative disorder in the present model system raises the possibility that dysregulated P-gp expression may contribute to the development of leukemia. In patients with acute myelogenous leukemia, between 35 and 70% of cases demonstrate P-gp expression in the pretreatment leukemic blasts, and P-gp expression is a strongly negative prognostic factor [Leith et al., *Blood* 94:1086–1099 (1999)]. In at least some instances increased P-gp expression in blast cells is due to hypomethylation of sequences in the MDR1 promoter [Nakayama et al., *Blood* 92:4296–4307(1998)]. In chronic myelogenous leukemia, about 60% of patients show MDR1 expression in leukemic cells from the bone marrow [Giles et al., *Cancer*, 86:805–813 (1999)]. While the occurrence of MDR1-negative cases could argue against a necessary role for dysregulated transporter expression in leukemogeniesis, it should be noted that high levels of expression of other transporter family members have been identified in a significant number of those cases [Leith et al., *Blood*, 94:1086–1099 (1999) and Michieli et al., *Br. J. Haematol*, 104:328–335 (1999)].

EXAMPLE 3

BCRP Expression Can Be Used as a Marker for Purification of Stem Cells

Introduction

Hematopoietic stem cells (HSCs) can be identified by staining with fluorescent dyes such as Rhodamine (Rho) 123 [Orlic et al., *Blood* 82:762–770 (1993); Fleming et al., *J. Cell Biol.* 122:897–902 (1993); Spangrude and Johnson, *Proc.Natl.Acad.Sci.USA* 87:7433–7437 (1990); Zijlmans et al., *Proc Natl Acad Sci USA* 92:8901–8905 (1995)] and Hoechst 33342 [McAlister et al., *Blood* 75:1240–1246 (1990); Leemhuis et al., *Exp.Hematol.* 24:1215–1224 (1996); Wolf et al., *Exp.Hematol.* 21:614–622 (1993)]. The most primitive HSCs are characterized by low degrees of fluorescence after staining with these dyes, a property ascribed to both their capacity for dye efflux, and to relatively low degrees of mitochondrial staining [Kim et al., *Blood* 91:4106–4117 (1998)]. A related method for stem cell identification has been based on Hoechst dye-staining of whole bone marrow cells, followed by dual emission wavelength analysis by flow cytometry. This technique identifies a small fraction of side population (SP) cells that are highly enriched for repopulating activity [Goodell et al., *J.Exp.Med.* 183:1797–1806 (1996)]. The SP phenotype identifies HSCs in a number of mammalian species [Goodell et al., *Nat.Med.* 3:1337–1345 (1997)], and can be blocked by drugs which inhibit cellular dye efflux mechanisms. It has been thought that the efflux activity responsible for the SP phenotype may be due to expression of P-glycoproteins (P-gps), the products of the mammalian multidrug resistance genes (MDR1 in humans and mdr1a and 1b in mice). This possibility is suggested by the facts that: (i) Rho 123 and Hoechst 33342 are substrates for P-gp, (ii) primitive human hematopoietic cells express high levels of P-gp [Chaudhary and Roninson, *Cell* 66:85–94 (1991)], and (iii) the phenotype of SP cells can be blocked by verapamil, a competitive inhibitor of P-gp [Goodell et al., *J.Exp.Med.* 183:1797–1806 (1996)]. More recent evidence shows that the muscle contains reconstituting cells that can be identified by the SP phenotype [Gussoni et al., *Nature* 401:390–394 (1999); Jackson et al., *Proc.Natl.Acad.Sci.U.S.A* 96:14482–14486 (1999), see comments] suggesting that expression of ABC transporters may be a general stem cell property. Indeed whatever their exact function, it appears that expression of ABC transporters has been evolutionarily conserved in stem cells. The conservation of transporter expression in a wide variety of stem cells is consistent with an important functional role in stem cells.

Although many of the genes encoding ABC transporters were first identified based on their ability to confer drug resistance in tumor cells, it has recently become apparent that they can exert more general effects on cellular function. For example, MDR1 gene expression has been shown to inhibit caspase-dependent apoptosis in a variety of cells [Smyth et al., *Proc.Natl.Acad.Sci.USA* 95:7024–7029 (1998)] including hematopoietic cells [Johnstone et al., *Blood* 93:1075–1085 (1999)]. P-gps can also function as lipid translocases by redistributing membrane phospholipids from the inner to outer leaflet of the cell membrane [van Helvoort et al., *Cell* 87:507–517 (1996)].

Direct evidence that ABC transporters can have a functional effect in HSCs comes from studies of MDR1 gene transfer in mice in Example 1 above. When murine bone marrow cells were transduced with all MDR1-expressinlg retroviral vector, dramatic expansion of repopulating stem cells was noted during a 12-day culture period [Example 1 above: Bunting et al., *Blood* 92:2269–2279 (1998)]. In contrast, repopulating activity was lost over time in control cultures [Example 2 above]. These results demonstrate that enforced expression of MDR1 results in stem cell self-renewal and expansion during extended culture periods. This expansion of repopulating cells was associated with a parallel increase in SP cells, while SP cells were lost over time in control cultures. These results directly link ABC transporter expression, or at least MDR1 expression, with the SP stem cell phenotype. One possible mechanism for the stem cell expansion was that P-gp expression could result in the efflux of toxic media components from HSCs during the ex vivo culture period. This possibility was ruled out by the observation that MDR1-transduced stem cells had a direct proliferative advantage in vivo [Example 2 above]. When transduced bone marrow cells were directly transplanted in irradiated mice, without an ex vivo expansion phase, there was a progressive outgrowth of MDR1-transduced cells relative to a control graft. These results show that MDR1 expression was conferring a more general effect on stem cell division, and not simply acting through a detoxification mechanism specific to ex vivo culture. Experiments with a mutant P-gp construct demonstrated that HSC expansion required the molecular pump function of P-gp, suggesting that the mechanism of expansion involved modulation of some endogenous molecular substrate within HSCs [Example 2 above]. Collectively, these studies show that MDR1 gene expression can promote HSC self-renewal and amplification. Heretofore, it was not known if this property is unique to the MDR1 gene, or whether other ABC transporters can exert a similar function.

Clinical evidence also shows an association between dysregulated ABC transporter expression and human leukemia. In chronic myelogenous leukemia, about 60% of chronic phase patients exhibit P-gp expression in leukemic cells from the bone marrow [Giles et al., *Cancer* 86:805–813 (1999)]. In patients with acute myelogenous leukemia (AML), between 35 and 70% of cases demonstrate P-gp expression in leukemic blasts at diagnosis, and P-gp expression was a strongly negative prognostic factor [Leith et al., *Blood* 94:1086–1099 (1999)]. In contrast, normal late myeloid cells in humans do not express P-gp [Drach et al., *Blood* 80:2729–2734 (1992), see comments]. In some cases, increased P-gp expression in blast cells was due to hypomethylation of sequences in the MDR1 promoter [Nakayama et al., *Blood* 92:4296–4307 (1998)]. Expression of other ABC transporters can occur in human AML, as has been documented for the multidrug resistance protein (MRP1), and the lung resistance protein (LRP) [Leith et al., *Blood* 94:1086–1099 (1999); Michieli et al., *Br.J.Haematol.* 104:328–335 (1999)]. Importantly, a signficant number of AML cases showved inhibitable dye efflux activity that was not associated with MDR1, MRP1, or LRP [Michieli et al., *Br.J.Haematol.* 104:328–335 (1999); Leith et al., *Blood* 86:2329–2342 (1995)].

A powerful way to define the normal function of ABC transporters in HSCs is by murine gene disruption experiments. Mice have two closely linked MDR1-like genes that are designated mdr1a and mdr1b. Both of these genes have been disrupted in single ES cells by a double knockout strategy, and the resulting mice have normal hematologic parameters [Schinkel et al., *Proc Natl Acad Sci USA* 94:4028–4033 (1997)]. Similarly, the multidrug resistance protein 1 (mrp1) gene has been knocked out with no apparent effect on hematopoiesis [Lorico et al., *Cancer Res.* 57:5238–5242 (1997)]. These findings indicate that expression of these particular ABC transporters is not necessary for HSC function, but do not rule out the possibility that other transporters are providing a critical redundant function in HSCs.

Results

The regulated expression of endogenous P-gps in HSCs appears to be important in facilitating the self-renewal divisions that maintain the stem cell compartment over time (see Examples 1 and 2 above) and indeed, one or more naturally occurring endogenous ABC transporters apparently plays a critical functional role in stem cell homeostasis. This premise is consistent with two observations: (i) HSCs universally express dye-effluxing transporters; and (ii) enforced expression of MDR1 leads to stem cell amplification and myeloproliferation (see Example 1 above).

As disclosed herein, an alternate ABC transporter(s) is expressed in SP stem cells derived from the mdr1a/1b knockout mouse. The analyses of mRNA from sorted SP stem cells have identified several newly cloned transporters that are expressed in SP HSCs, that may possibly have a role in the self-renewal process of HSCs. The most highly expressed is the Bcrp1/Mxr/Abcp gene product, BCRP. Importantly, there is no detectable expression of BCRP in peripheral blood leukocytes, spleen, or thymus at the level of Northern blot analysis, while small but detectable amounts of BCRP mRNA were expressed in human fetal liver. BCRP-transfected cells effluxed Rho 123 by an ATP-dependent mechanism, which is consistent with it having a role in dye efflux within stem cells [Doyle et al., *Proc.Natl.Acad.Sci.USA* 95:15665–15670 (1998): published erratum appears in *Proc Natl Acad Sci USA;* 96(5):2569 (1999)].

Figures 16A, 16B, 16C, 16D:
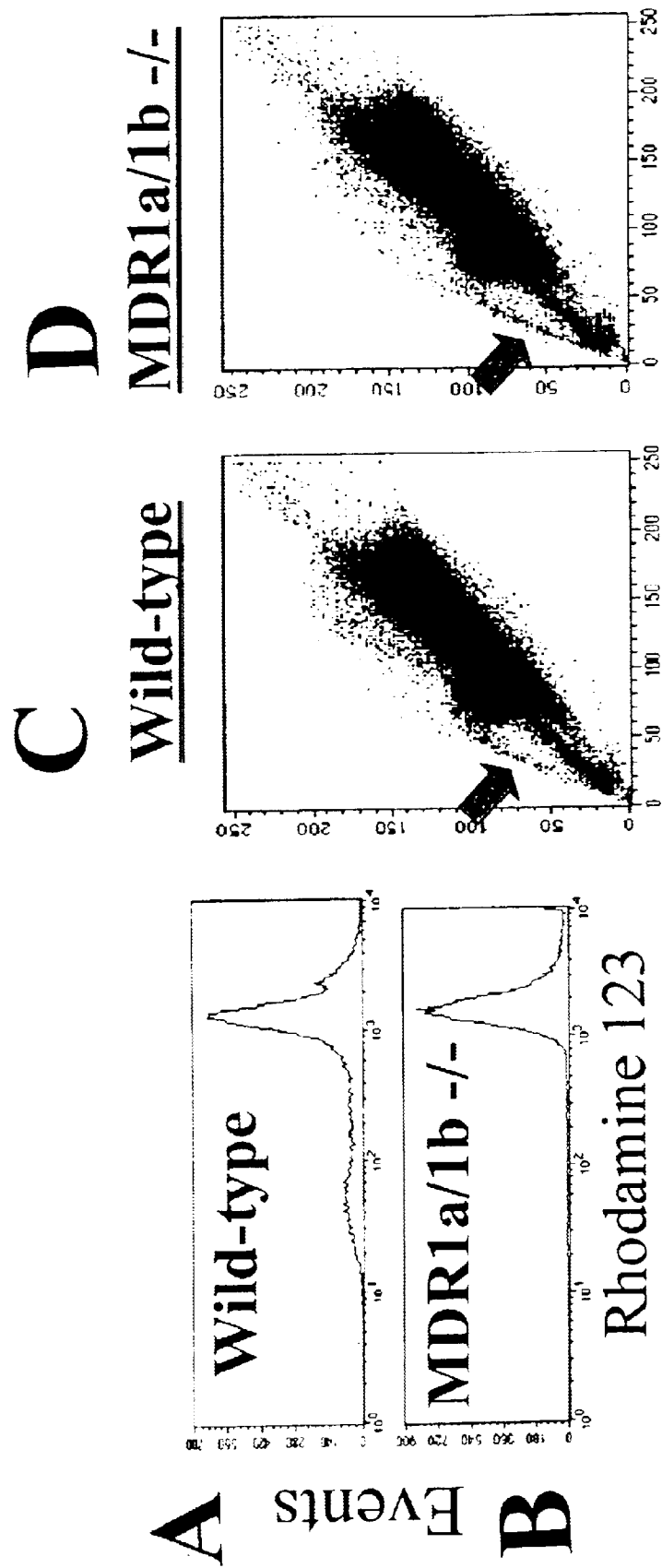
FIGS. 16A–16D show the SP cell analyses of BM cells from mdr1a/mdr1b knockout mice.

An ABC transporter other than P-gp is expressed in murine SP HSCs: Quantitative repopulation assays were performed using commercially available mdr1a/ab −/− mice as donors because it is well known that severe quantitative stem cell abnormalities can coexist with relatively normal peripheral blood counts such as in $W/W_v$ mice. Normal numbers of repopulating cells were found to be present in the bone marrow. Bone marrow cells were then analyzed for the content of SP cells after staining with Hoechst dye. To confirm that the knockout mice had the expected phenotype, it was verified that the capacity for Rho 123 efflux had been lost in peripheral blood leukocytes (FIG. 16A–16D) as has been previously described [Schinkel et al., *Proc Natl Acad Sci USA* 94:4028–4033 (1997)]. Despite this loss of P-gp related transporter function, SP cells were present in normal numbers in the bone marrow when compared to wild type mice of the same strain (FIGS. 16A–16B). This indicates that another ABC transporter is likely being expressed, potentially compensating for the loss of P-gp function.

Figure 17A:
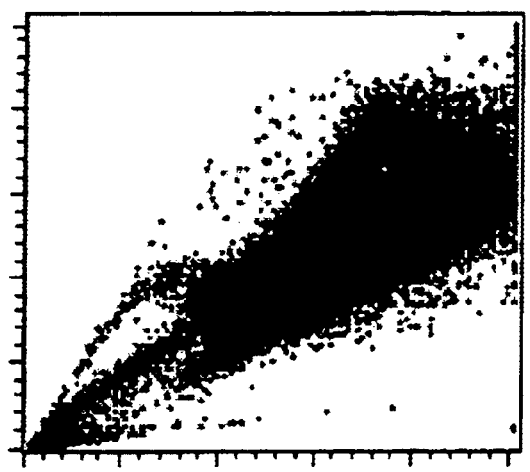
FIGS. 17A–17C show the results of the treatment of the SP cell phenotype of BM cells from mdr1a/mdr1b knockout mice with ABC transport inhibitors. The bone marrow cells were either untreated (FIG. 17A), treated with verapamil (FIG. 17B) or treated with 2-deoxyglucose (FIG. 17C) before and during Hoechst dye staining and efflux. The resulting SP analyses are shown.
Figure 17B:
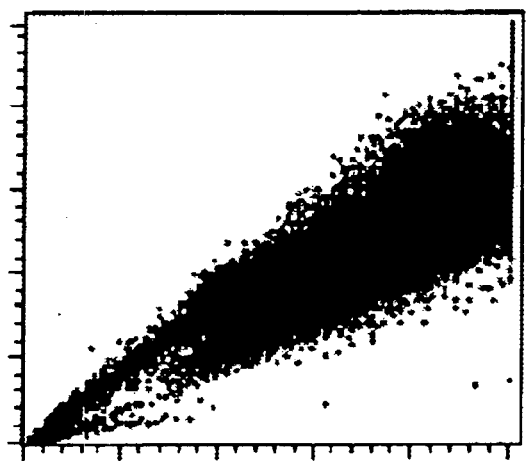
Figure 17C:
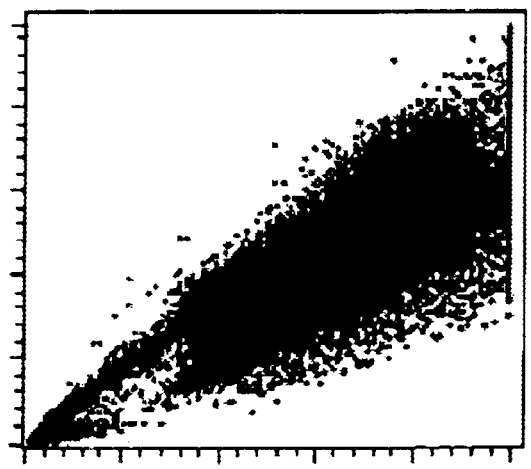

To further test this possibility, biochemical studies were performed on knockout bone marrow cells using known inhibitors of ABC transporter efflux function. Cells were treated with either verapamil or 2-deoxyglucose. Verapamil is a competitive inhibitor of several known ABC transporters including MDR1, whereas 2-deoxyglucose is an inhibitor of ATP synthesis that depletes cellular ATP levels required for ABC transporter function. Treatment with either of these compounds before and during Hoechst 33342 staining eliminated phenotypically identifiable SP cells (FIG. 17). These results conclusively demonstrate that another ABC transporter(s) is being expressed in SP cells from the bone marrow of mdr1a/1b knockout mice and is (are) responsible for the SP phenotype.

Figure 18:
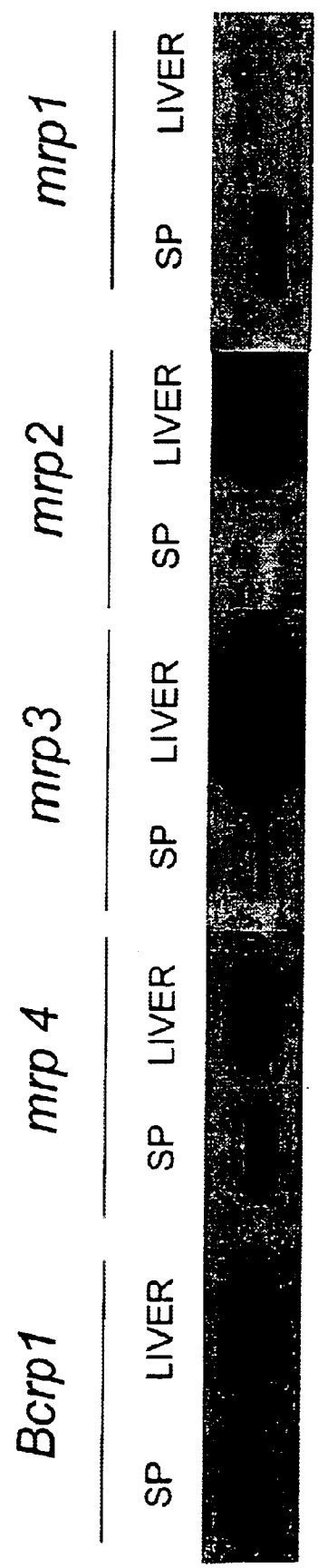
FIG. 18 shows the RT-PCR analysis of ABC transporter expression in SP Cells from mdr1a/mdr1b knockout mice. cDNAs from liver and sorted SP cells were amplified for 35 cycles with the indicated primer sets in the presence of $^{32}$P-labeled dCTP and then resolved by electrophoresis. The bands, as indicated, were the size anticipated. No signals were detected in mRNA samples without reverse transcriptase.

Identification of Bcrp as an expressed ABC transporter in hematopoietic stem cells: An RT-PCR assay was developed to detect mRNA expression of other known ABC transporters in murine hone marrow SP cells. Based on the published human sequences for MRP1 [Cole et al., Science 258:1650–1654 (1992), see comments], MRPs 2, 3, 4 [Kool et al., Cancer Res. 57:3537–3547 (1997)]. and BCRP [Doyle et al., Proc.Natl.Acad.Sci.U.S.A 95:15665–15670 (1998) :published erratum appears in Proc Natl Acad Sci USA; 96(5):2560 (1999)] homologous sequences from the murine EST database were identified to design PCR primers for cDNA amplification. Multiple primer sets were tested using mouse liver cDNA as a template, and primer sets were chosen that gave specific bands of the expected size. Using FACS, bone marrow SP cells were sorted from both normal mice and the mdr1a/1b knockout mouse. Total cellular RNA was prepared from 50,000 and 101,000 purified SP cells, and then used for RT-PCR analysis. These experiments showed that the Bcrp1 mRNA was the most highly expressed of all the transporters studied (FIG. 18). Moderate expression levels were observed for mrp4 and mrp1, while mrp3 was expressed at very low levels, and no detectable expression of mrp2 was observed. The low levels of expression of mrp1 in the liver correlated with previously described low levels of expression of MRP1 in human liver [Kool et al., Cancer Res. 57:3537–3547 (1997)]. Virtually identical results were obtained using sorted SP cells from normal mice.

Figure 19:
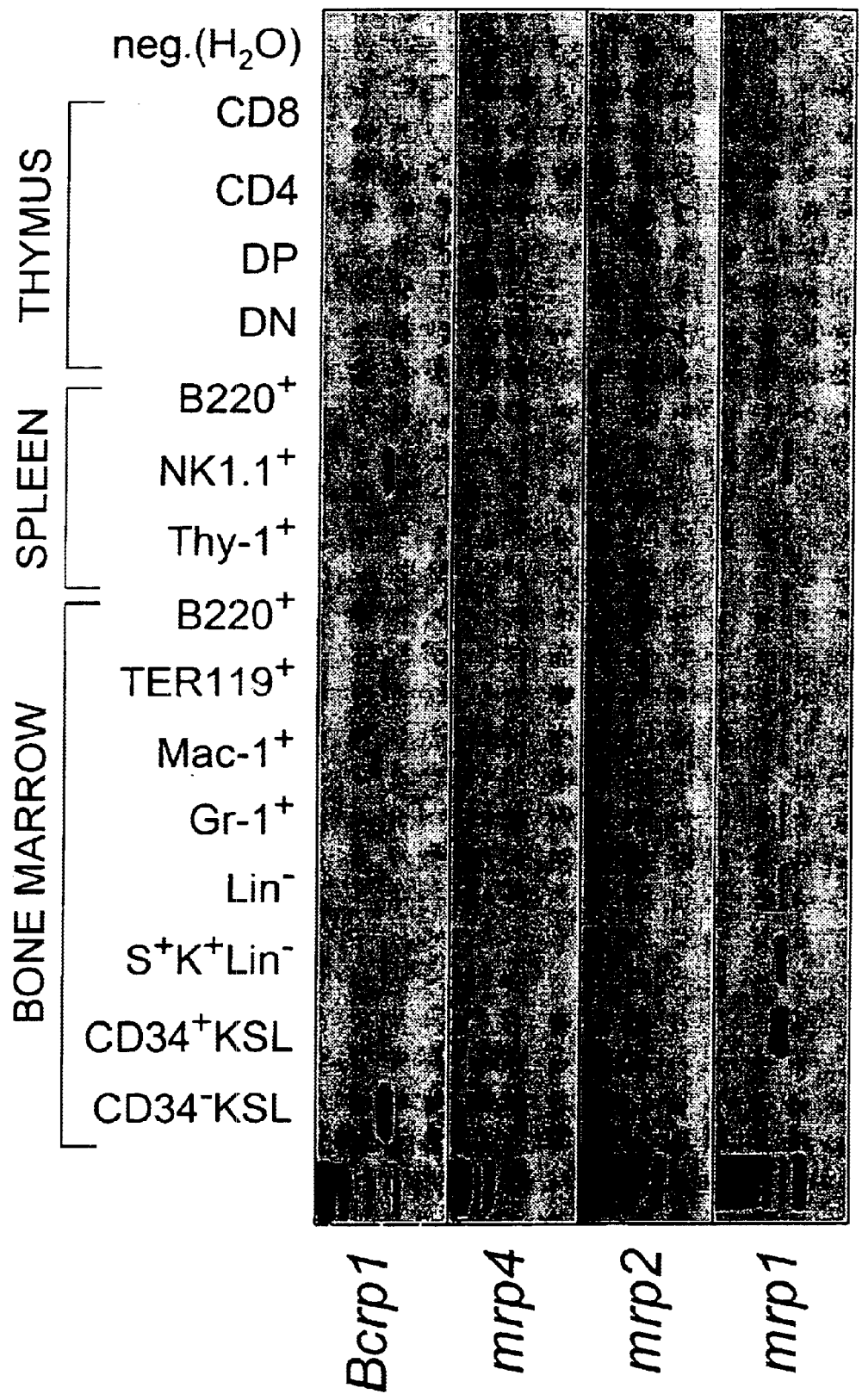
FIG. 19 shows the expression of ABC transporter mRNAs in various sorted hematopoietic populations from normal mice. Expression of Bcrp1, mrp4, mrp2, and mrp1 was assessed by RT-PCR in CD34+ and—subpopulations of c-kit+, Sca1+, lin-(KSL) bone marrow cells. Other markers used for sorting are shown above each column, including thymocytes that were double negative (DN) and double positive for CD4 and 8 expression. All RNAs gave equivalent GAPDH mRNA signals.

It is important to note that while SP cells are highly enriched for repopulating cells, at least 250 SP cells are required to achieve significant repopulation in mice [Goodell et al., J.Exp.Med. 183:1797–1806 (1996)] indicating that most SP cells are not true stem cells. In contrast, it has previously been shown that CD34−, c-kit+, Sca1+, lineage negative (CD34-KSL) cells from the bone marrow are a relatively pure subset of repopulating cells, with repopulation in about 20% of mice that are transplanted with single sorted cells [Osawa et al., Science 273:242–245 (1996)]. Therefore, transporter expression was studied in the highly purified CD34−KSL population, as well as from a number of other different sorted populations. Like SP cells, the CD34-KSL cells expressed relatively high levels of Bcrp1 mRNA, however in contrast to SP cells, there were little to no expression of the other ABC transporters (FIG. 19). In the more differentiated CD34+KSL cell fraction, there was marked downregulation of Bcrp1 expression with the appearance of significant expression of mrp1, 2, and 4. The S+K+Lin-population is a mixture of CD34− and +cells, and gave results that were intermediate between the CD34+ and − subfractions. Bcrp1 expression was not detectable in granulocytes, macrophages, B cells, or thymocytes. The only other cell populations with detectable Bcrp1 expression were erythroid progenitors (Ter119+) and natural killer cells (NK1.1+). These results suggest that Bcrp1 expression is highly specific for repopulatlig stein cells in the lineage negative compartment of the bone marrow, and that expression of other transporters in the sorted SP cell population were likely due to the presence of more differentiated cells with lesser degrees of repopulation potential. These data indicate that Bcrp1 and/or BCRP expression should be useful markers for stem cell identification and purification. The expression data are also consistent with a necessary functional role for Bcrp1 gene expression in repopulating hematopoietic stem cells, and perhaps in SP stem cells from muscle and other tissues.

Figure 20A:
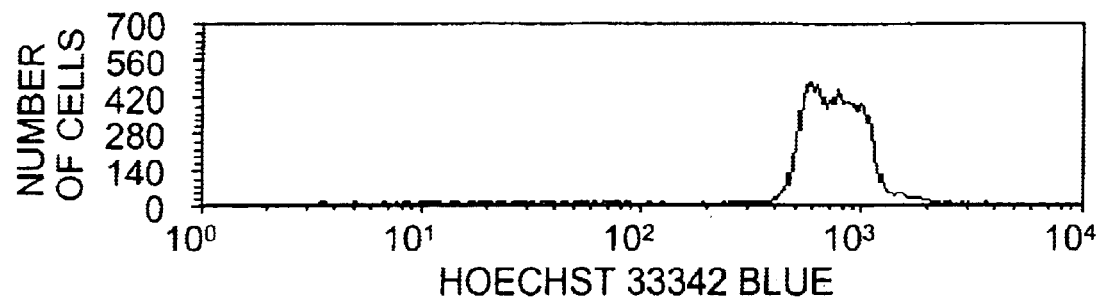
FIGS. 20A–20C show the efflux of Hoechst dye in control (FIG. 20A), BCRP (FIG. 20C) and MRP1 (FIG. 20B) retroviral producer cell lines. Cells were incubated with Hoechst dye, and then allowed to efflux in dye-free media for 60 minutes. Cells were then analyzed for Hoechst dye staining by flow cytometry. Parental GPE86 cells and an MRP1 producer line were assayed together with the BCRP line.
Figure 20B:
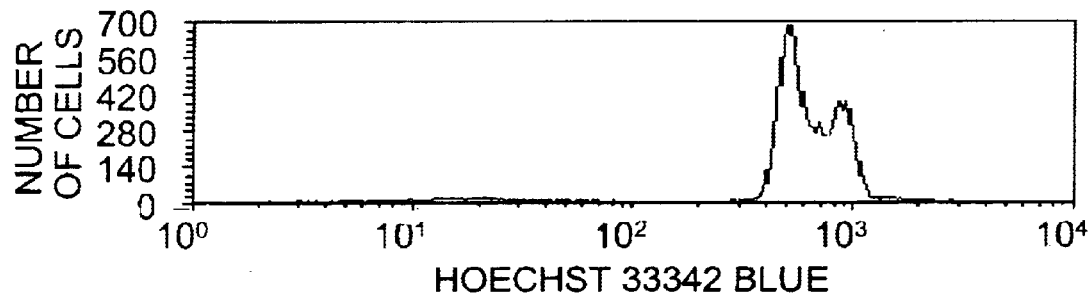
Figure 20C:
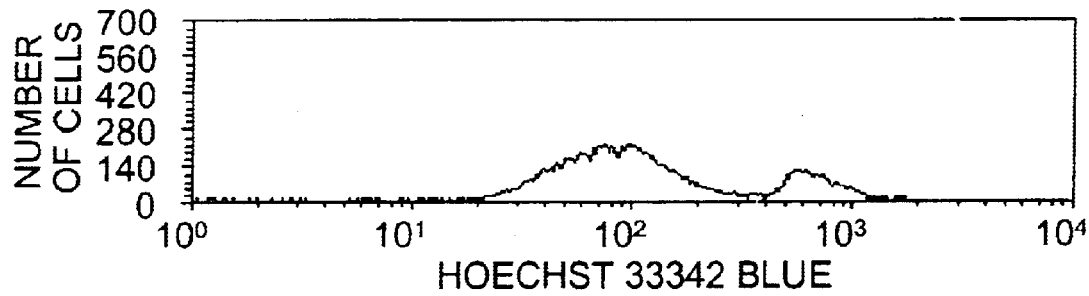

Functional studies with a BCRP retroviral vector confirm dye efflux activity consistent with the SP cell phenotype: To gain further information regarding BCRP as a functional determinant of SP stem cells, a retroviral vector based on the Murine stem cell virus (MSCV) was constructed that expressed both the human Bcrp cDNA and a linked GFP marker gene. Ecotropic producer cells were generated and shown to express the BCRP protein by Western blot, using an polyclonal rabbit antibody that recognizes an internal epitope of BCRP. It was next determined whether BCRP could efflux Hoechst dye, a prerequisite for conferring the SP phenotype. Efflux studies done in the murine fibroblast producer cells clearly demonstrated that BCRP efficiently effluxed Hoechst dye, while neither the parental cells nor an MRP1 producer cell line showed any efflux activity (FIG. 20). The blue wavelength used for emission analysis did not overlap with the GFP emission wavelength, as was demonstrated using a producer cell line that coexpressed GFP and a DNA repair enzyme (MSCV-MGMT-GFP).

Figure 21A:
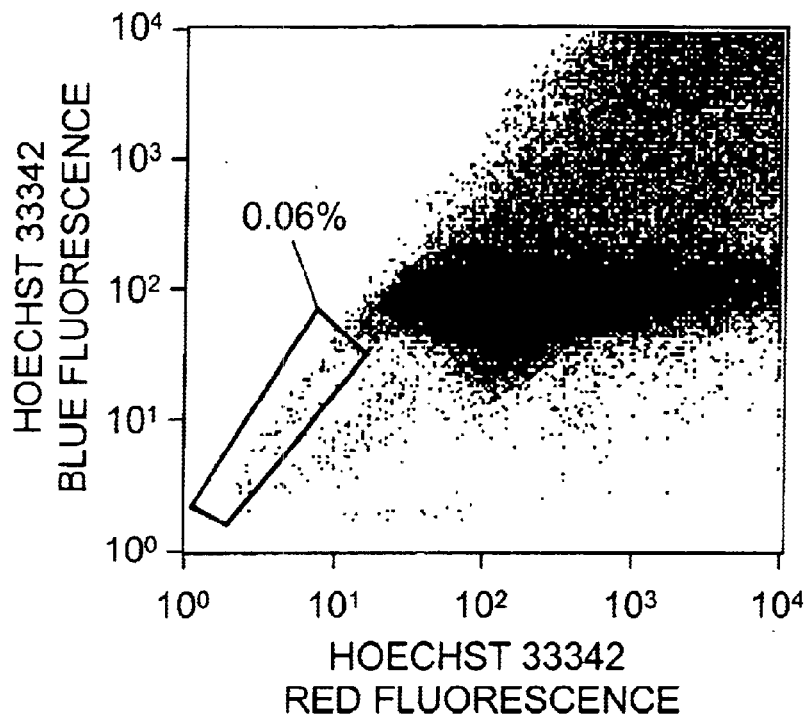
FIGS. 21A–21B show the ex vivo expansion of SP cells after transduction with a BCRP retroviral vector. Murine bone marrow cells were transduced with MSCV-BCRP-GFP (FIG. 21B) or a MGMT control vector (FIG. 21A), and then cultured for an additional 7 days in IL3, IL6, and SCF. At the end of the culture period, the expanded population was analyzed for SP cells after Hoechst dye staining. The measured proportion of cells in the SP gate is indicated within each panel.
Figure 21B:
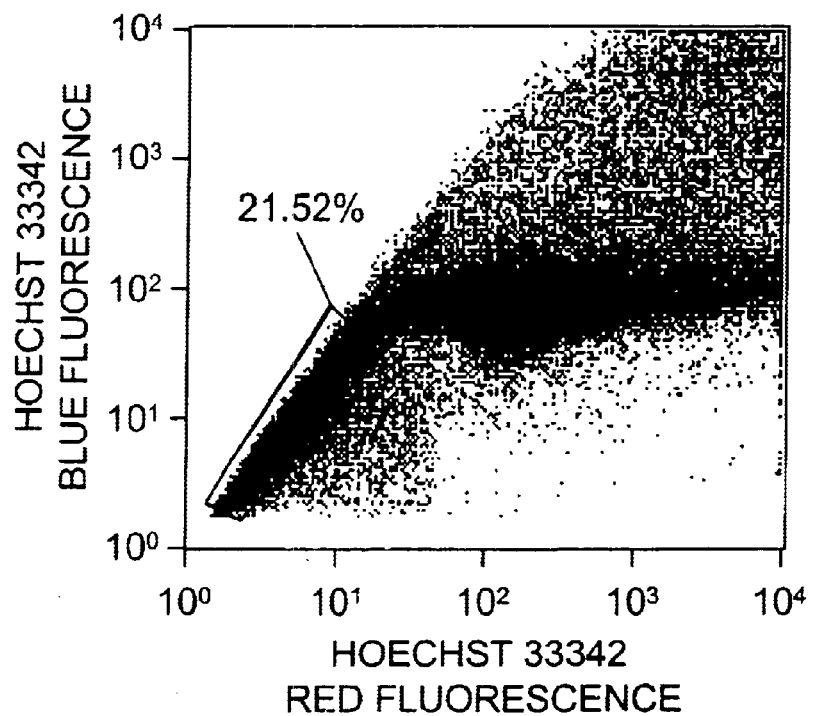

To further clarify the link between BCRP expression and the SP cell phenotype, the BCRP vector was used to transduce murine bone marrow cells. The transduced cells were grown in expansion cultures for 7 days and analyzed by FACS for expansion of the SP population. As a negative control, cells were transduced with the MSCV-MGMT-GFP vector and expanded in parallel. Whereas, a large expansion of phenotypic SP cells was seen with the BCRP vector, in marked contrast, there was a relative loss of SP cells in the control population (FIG. 21 A). After 7 days of culture, about 22% of the population transduced with the BCRP vector fell within the SP gate (FIG. 21B), which constituted a significantly greater degree of expansion than was previously noted with the HaMDR1 vector (FIG. 8). The data from the BCRP retroviral experiments further strengthen the association between BCRP expression and the SP phenotype of stem cells:

High levels of expression of BCRP mRNA in sorted SP cells from Rhesus Monkey bone marrow: To determine if primate SP cells were expressing BCRP, a bone marrow aspirate sample was obtained from a normal Rhesus Monkey. After lysis of the red blood cells, the leukocyte population was stained with Hoechst dye and analyzed by flow cytometry for SP cells. The flow pattern was very similar to that obtained with mouse bone marrow, with about 0.05% of cells falling into the SP gate (see above). Sorting was performed and resulted in isolation of 2000 SP cells, and 10,000 cells from a distinct gate outside of the SP region (non-SP cells). RNA was extracted, and a RT-PCR cycle curve using β-actin primers as an internal control showed roughly equivalent signals at 35 cycles for non-SP cells versus 60 cycles for SP cells (FIGS. 22A–22C). These PCR conditions were repeated using BCRP-specific primers in place of the β-actin primers. A strong signal was obtained with BCRP primers at 60 cycles in the SP cells sample (FIG. 22B), and a much fainter signal was detected at 50 cycles. No BCRP signal was detected at 35 cycles in the non-SP sample, which was the highest cycle number used for this sample (FIG. 22C). These results demonstrate relatively specific, high level expression of BCRP mRNA in monkey SP cells since the β-actin signal for non-SP cells at 35 cycles was actually greater than the signal for SP cells at 60 cycles. Taken together with the mouse data, (above) these results show that the expression of a BCRP transporter ortholog is conserved in SP stem cells from diverse species. In addition, these results further confirm that human stem cells can be identified and/or purified by monitorinig/exploiting their unique BCRP expression.

Expression of Bcrp1 in murine myoblast SP cells: Stem cells bearing the SP phenotype have also been identified in murine muscle, and appear to be related to the satellite cells that are located on the periphery of the muscle fiber. Consistently, these cells also appear to be associated with muscle regeneration. SP cells were therefore isolated from the murine muscle, and assayed for Bcrp1 expression by RT-PCR to further correlate Bcrp1 (BCRP) expression with the SP phenotype. Muscle tissue was dissected, minced, digested with collagenase, and a single cell suspension was stained with Hoechst dye for SP cell analysis. An SP population of cells was observed with FACS analysis that bears a striking resemblance to the profile seen with bone marrow cells (FIG. 22D). Gated myoblast SP cells were sorted, and RNA was prepared from a fraction of 20,000 cells. RT-PCR analysis showed relatively high levels of Bcrp1 expression (FIG. 22E). However, unlike the results with monkey bone marrow, a distinct non-SP cell fraction was not available for analysis. These results further support the conclusion that Bcrp1 expression can be used to identify SP stem cells from a variety of organs.

Figure 23A:
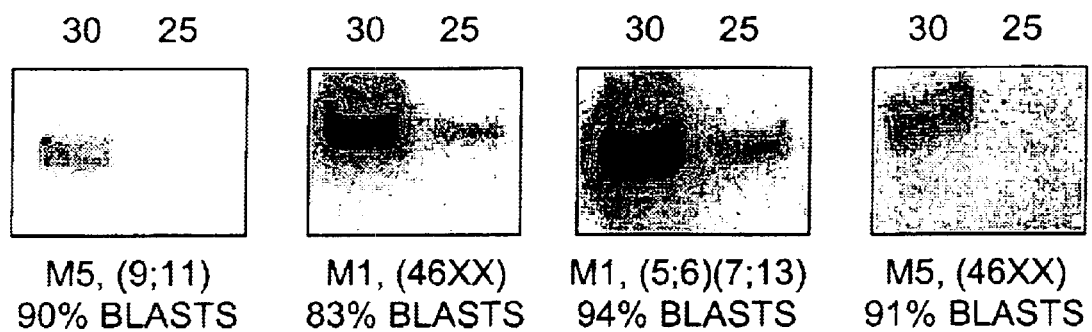
FIGS. 23A–23B show Bcrp1 expression in pediatric AML blasts. RNA obtained from bone marrow blast cells from four individuals with AML was amplified by RT-PCR using primers for BCRP (FIG. 23A) or β-actin (FIG. 23B). Cycle numbers are indicated above each lane, and the AML phenotype and blast percentage are also shown.
Figure 23B:
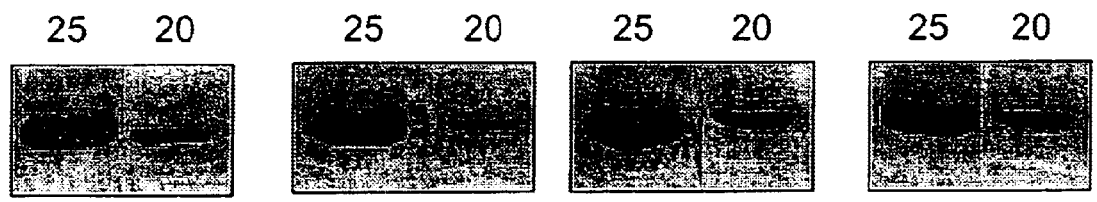

BCRP expression in blasts from pediatric acute myelogenous leukemia (AML). To determine if BCRP expression could be detected in leukemia cells from pediatric patients with AML, RT-PCR analysis was performed on RNAs derived from leukemic bone marrow from four individual cases (FIGS. 23A–23B). Two cases were strongly positive for BCRP mRNA, with BCRP-amplified fragments detected at 25 cycles of amplification. Interestingly both of these "high-expressing" cases were associated with the M1 FAB phenotype. Two other cases with an M5 phenotype did not show any detectable signal at 25 cycles, but BCRP could be detected at 30 cycles. β-actin controls demonstrated that this variation was not due to differences in mRNA loading. The low level signal seen in the M5 cases could have been due to contaminating erythroid progenitors which may be expressing BCRP, or due to low level BCRP expression in the blast cells. These data confirm that BCRP mRNA expression can be detected in at least some primary AML samples. Furthermore, these results provide further impetus for using an anti-BCRP antibody to probe blast cell samples in the diagnosis prognosis of AML.

The following is a list of documents related to the above disclosure and particularly to the experimental procedures and discussions. These documents, and all others cited above, should be considered as incorporated by reference in their entirety.

References

1. Nienhuis et al., *Cancer* 67:2700 (1991)
2. Lemischka et al, *Cell* 45:917 (1986)
3. Dick et al., *Cell* 42:71 (1985)
4. Szilvassy et al., *Proc.Natl.Acad.Sci.USA* 86:8798 (1989)
5. Brenner et al., *Lancet* 342:1134 (1993)
6. Brenner et al., *Lancet* 341:85 (1993)
7. Rill et al., *Blood* 84:380 (1994)
8. Dunbar et al., *Hum.Gene Ther.* 7:231 (1996)
9. Bodine et al., *Proc.Natl.Acad.Sci.USA* 86:8897 (1989)
10. Bodine et al., *Blood* 78:914 (1991)
11. Kittler et al., *Blood* 90:865 (1997)
12. Traycoff et al., *Experimental Hematology* 24:299 (1996)
13. Peters et al., *Blood* 87:30 (1996)
14. Traycoff et al., *Experimental Hematology* 26:53 (1998)
15. Muench et al., *Blood* 81:3463 (1993)
16. Flasshove et al., *Blood* 85:566 (1995)
17. Petzer et al., *J.Exp.Med.* 183:2551 (1996)
18. Petzer et al., *Proc.Natl.Acad.Sci.USA* 93:1470(1996)
19. Zandstra et al., *Proc.Natl.Acad.Sci.USA* 94:4698 (1997)
20. Larochelle et al., *Nat.Med.* 2:1329 (1996)
21. Gan et al., *Blood* 90:641 (1997)
22. Bhatia et al., *J.Exp.Med.* 186:619 (1997)
23. Moritz et al., *Cancer Res* 55:2608 (1995)
24. Galipeau et al., *Human Gene Therapy* 8:1773 (1997)
25. Spencer et al., *Blood* 87:2579 (1996)
26. Spencer et al., *Blood* 87:2579 (1996)
27. Scarpa et al., *Virology* 180:849 (1991)
28. Brugger et al., *Blood* 81:2579 (1993)
29. Williams, *Blood* 81:3169 (1993)
30. Uchida et al., *Blood* 88:1297 (1996)
31. Chaudhary et al., *Cell* 66:85 (1991)
32. Borst et al., *Pharmacology & Therapeutics* 60:289 (1993)
33. Schinkel et al., *Seminars in Cancer Biology* 2:213 (1991)
34. Borst P et al., *Acta Oncologica* 30:87 (1991)
35. Schinkel et al., *Cell* 77:491 (1994)
36. Smit J J et al., *Cell* 75:451 (1993)
37. Schinkel et al., *Proceedings of the National Academy of Sciences of the United States of America* 94:4028 (1997)
38. van Helvoort et al. *Cell* 87:507 (1996)
39. Martin et al., *Journal of Biological Chemistry* 271:28753, 1996
40. Martin et al., *Journal of Experimental Medicine* 182:1545, 1995
41. Robinson et al., *Biochemistry* 36:11169 (1997)
42. Bezombes et al., *FASEB Journal* 12:101 (1998)
43. Gruol et al., *Biochemistry & Cell Biology* 72:561 (1994)
44. Podda et al., *Proc.Natl.Acad.Sci.USA* 89:9676 (1992)
45. Ward et al., *Blood* 84:1408 (1994)
46. Sorrentino et al., *Blood* 86:491 (1995)
47. Hanania et al., *Cancer Gene Ther.* 1:21 (1994)

While the invention has been described and illustrated herein by references to the specific embodiments, various specific material, procedures and examples, it is understood that the invention is not restricted to the particular material combinations of material, and procedures selected for that purpose. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications in addition to the immediately foregoing are cited hetein, the disclosures of wvhichi are also incorporated by reference in their entireties.

What is claimed is:

1. A method of performing ex vivo expansion of a gene-modified hematopoietic stem cell comprising:

(a) transducing a hematopoietic stem cell with a nucleic acid encoding an ABC transporter, wherein the hematopoietic stem cell is transduced to become a gene-modified hematopoietic stem cell;

(b) expressing the transduced ABC transporter; and (c) culturing the gene-modified hematopoietic stem cell ex vivo wherein the gene-modified hematopoietic stem cell is expanded.

2. The method of claim 1 wherein said culturing is performed in the presence of an early-acting hematopoietic cytokine.

3. The method of claim 2 wherein the cytokine is selected from the group of cytokines consisting of interleukin-3, interleukin-6, G-CSF, GM-CSF, FLT-3 ligand, and stem cell factor.

4. The method of claim 1 wherein transducing the hematopoietic stem cell with a nucleic acid encoding an ABC transporter is performed with a viral vector comprising a nucleic acid encoding the ABC transporter.

5. The method of claim 4, wherein the viral vector is selected from the group of viral vectors consisting of a herpes simplex viral vector, an adenoviral vector, and adeno-associated viral vector (AAV).

6. The method of claim 4 wherein the viral vector is a retroviral vector.

7. The method of claim 6 wherein the retroviral vector is a Harvey Murine Sarcoma Vector and the hematopoietic stem cell is transduced by co-culture on retroviral producer cell lines.

8. The method of claim 1 wherein transducing the hematopoietic stem cell with a nucleic acid encoding ABC transporter is performed with a DNA vector comprising a nucleic acid encoding the ABC transporter.

9. The method of claim 1 wherein the hematopoietic stem cell is a mammalian hematopoietic stem cell.

10. The method of claim 8 wherein the gene-modified hematopoietic stem cell expresses a splice-corrected version of the human MDR1.

11. The method of claim 8 wherein the mammalian hematopoietic stem cell is a murine hematopoietic stem cell.

12. The method of claim 8 wherein the mammalian hematopoietic stem cell is a human hematopoietic stem cell.

13. A gene-modified mammalian hematopoietic stem cell that has been (i) transduced with a nucleic acid encoding an ABC transporter selected from the group consisting of MDR1 and BCRP, wherein the ABC transporter is expressed; and (ii) expanded.

14. The gene-modified hematopoietic stem cell of claim 13 that has been expanded for at least 9 days.

15. The method of claim 1 wherein the ABC transporter is MDR1 or BCRP.

* * * * *

SEQUENCE LISTING

<160> NUMBER OF SEQ ID NOS: 16

<210> SEQ ID NO 1

-continued

<211> LENGTH: 3860
<212> TYPE: DNA
<213> ORGANISM: Homo sapiens
<220> FEATURE:
<223> OTHER INFORMATION: Human MDR 185-G

<400> SEQUENCE: 1

| | | | | | |
|---|---|---|---|---|---|
| atggatcttg | aagggaccg | caatggagga | gcaaagaaga | agaactttt | taaactgaac | 60 |
| aataaaagtg | aaaagataa | gaaggaaaag | aaaccaactg | tcagtgtatt | ttcaatgttt | 120 |
| cgctattcaa | attggcttga | caagttgtat | atggtggtgg | gaactttggc | tgccatcatc | 180 |
| catgggctg | gacttcctct | catgatgctg | gtgtttggag | aaatgacaga | tatctttgca | 240 |
| aatgcaggaa | atttagaaga | tctgatgtca | aacatcacta | atagaagtga | tatcaatgat | 300 |
| acaggttct | tcatgaatct | ggaggaagac | atgaccagat | atgcctatta | ttacagtgga | 360 |
| attggtgctg | gggtgctggt | tgctgcttac | attcaggttt | cattttggtg | cctggcagct | 420 |
| ggaagacaaa | tacacaaaat | tagaaaacag | tttttttcatg | ctataatgcg | acaggagata | 480 |
| ggctggtttg | atgtgcacga | tgttggggag | cttaacaccc | gacttacaga | tgatgtctct | 540 |
| aagattaatg | aaggtattgg | tgacaaaatt | ggaatgttct | ttcagtcaat | ggcaacattt | 600 |
| ttcactgggt | ttatagtagg | atttacacgt | ggttggaagc | taaccttgt | gatttttggcc | 660 |
| atcagtcctg | ttcttggact | gtcagctgct | gtctgggcaa | agatactatc | ttcatttact | 720 |
| gataaagaac | tcttagcgta | tgcaaaagct | ggagcagtag | ctgaagaggt | cttggcagca | 780 |
| attagaactg | tgattgcatt | tggaggacaa | agaaagaaac | ttgaaaggta | caacaaaaat | 840 |
| ttagaagaag | ctaaaagaat | tgggataaag | aaagctatta | cagccaatat | ttctataggt | 900 |
| gctgctttcc | tgctgatcta | tgcatcttat | gctctggcct | tctggtatgg | gaccaccttg | 960 |
| gtcctctcag | gggaatattc | tattggacaa | gtactcactg | tattctttc | tgtattaatt | 1020 |
| ggggcttta | tgttggaca | gcatctccca | agcattgaag | catttgcaaa | tgcaaggaga | 1080 |
| gcagcttatg | aaatcttcaa | gataattgat | aataagccaa | gtattgacag | ctattcgaag | 1140 |
| agtgggcaca | aaccagataa | tattaaggga | aatttggaat | tcagaaatgt | tcacttcagt | 1200 |
| tacccatctc | gaaaagaagt | taagatcttg | aagggcctga | acctgaaggt | gcagagtggg | 1260 |
| cagacggtgg | ccctggttgg | aaacagtggc | tgtgggaaga | gcacaacagt | ccagctgatg | 1320 |
| cagaggctct | atgaccccac | agaggggatg | gtcagtgttg | atggacagga | tattaggacc | 1380 |
| ataaatgtaa | ggtttctacg | ggaaatcatt | ggtgtggtga | gtcaggaacc | tgtattgttt | 1440 |
| gccaccacga | tagctgaaaa | cattcgctat | ggccgtgaaa | atgtcaccat | ggatgagatt | 1500 |
| gagaaagctg | tcaaggaagc | caatgcctat | gactttatca | tgaaactgcc | tcataaattt | 1560 |
| gacaccctgg | ttggagagag | aggggcccag | ttgagtggtg | ggcagaagca | gaggatcgcc | 1620 |
| attgcacgtg | ccctggttcg | caaccccaag | atcctcctgc | tggatgaggc | cacgtcagcc | 1680 |
| ttggacacag | aaagcgaagc | agtggttcag | gtggctctgg | ataaggccag | aaaaggtcgg | 1740 |
| accaccattg | tgatagctca | tcgtttgtct | acagttcgta | atgctgacgt | catcgctggt | 1800 |
| ttcgatgatg | gagtcattgt | ggagaaagga | aatcatgatg | aactcatgaa | agagaaaggc | 1860 |
| atttacttca | aacttgtcac | aatgcagaca | gcaggaaatg | aagttgaatt | agaaaatgca | 1920 |
| gctgatgaat | ccaaaagtga | aattgatgcc | ttggaaatgt | cttcaaatga | ttcaagatcc | 1980 |
| agtctaataa | gaaaaagatc | aactcgtagg | agtgtccgtg | gatcacaagc | ccaagacaga | 2040 |
| aagcttagta | ccaagaggc | tctggatgaa | agtataccc | cagtttccctt | ttggaggatt | 2100 |
| atgaagctaa | atttaactga | atggccttat | tttgttgttg | gtgtatttg | tgccattata | 2160 |

```
aatggaggcc tgcaaccagc atttgcaata atattttcaa agattatagg ggttttttaca    2220 agaattgatg atcctgaaac aaaacgacag aatagtaact tgttttcact attgtttcta    2280
gcccttggaa ttatttcttt tattacattt ttccttcaag gtttcacatt tggcaaagct    2340
ggagagatcc tcaccaagcg gctccgatac atggttttcc gatccatgct cagacaggat    2400
gtgagttggt ttgatgaccc taaaacacc actggagcat tgactaccag gctcgccaat    2460
gatgctgctc aagttaaagg ggctataggt tccaggcttg ctgtaattac ccagaatata    2520
gcaaatcttg ggacaggaat aattatatcc ttcatctatg gttggcaact aacactgtta    2580
ctcttagcaa ttgtacccat cattgcaata gcaggagttg ttgaaatgaa atgttgtct    2640 ggacaagcac tgaaagataa gaaagaacta gaaggtgctg ggaagatcgc tactgaagca    2700
atagaaaact tccgaaccgt tgtttctttg actcaggagc agaagtttga acatatgtat    2760
gctcagagtt tgcaggtacc atacagaaac tctttgagga agcacacat ctttggaatt    2820 acatttttcct tcacccaggc aatgatgtat ttttcctatg ctggatgttt ccggtttgga    2880
gcctacttgg tggcacataa actcatgagc tttgaggatg ttctgttagt attttcagct    2940
gttgtctttg gtgccatggc cgtggggcaa gtcagttcat ttgctcctga ctatgccaaa    3000
gccaaaatat cagcagccca catcatcatg atcattgaaa aaaccccttt gattgacagc    3060
tacagcacgg aaggcctaat gccgaacaca ttggaaggaa atgtcacatt tggtgaagtt    3120
gtattcaact atcccaccg accggacatc ccagtgcttc agggactgag cctggaggtg    3180
aagaagggcc agacgctggc tctggtgggc agcagtggct gtgggaagag cacagtggtc    3240
cagctcctgg agcggttcta cgaccccttg gcagggaaag tgctgcttga tggcaaagaa    3300
ataaagcgac tgaatgttca gtggctccga gcacacctgg gcatcgtgtc ccaggagccc    3360
atcctgtttg actgcagcat tgctgagaac attgcctatg gagacaacag ccgggtggtg    3420
tcacaggaag agatcgtgag ggcagcaaag gaggccaaca tacatgcctt catcgagtca    3480
ctgcctaata aatatagcac taaagtagga gacaaaggaa ctcagctctc tggtggccag    3540
aaacaacgca ttgccatagc tcgtgcccct gttagacagc ctcatatttt gcttttggat    3600
gaagccacgt cagctctgga tacagaaagt gaaaaggttg tccaagaagc cctggacaaa    3660
gccagagaag gccgcacctg cattgtgatt gctcaccgcc tgtccaccat ccagaatgca    3720
gacttaatag tggtgtttca gaatggcaga gtcaaggagc atggcacgca tcagcagctg    3780
ctggcacaga aaggcatcta ttttcaatg gtcagtgtcc aggctggaac aaagcgccag    3840
tgaactctgg ttaactccac                                              3860

<210> SEQ ID NO 2
<211> LENGTH: 1280
<212> TYPE: DND
<213> ORGANISM: Homo sapiens
<220> OTHER INFORMATION: Human MDR 185-G

<400> SEQUENCE 2

Met Asp Leu Glu Gly Asp Arg Asn Gly Gly Ala Lys Lys Lys Asn Phe
 1               5                  10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60
```

-continued

```
Leu Pro Leu Met Met Leu Val Phe Gly Glu Met Thr Asp Ile Phe Ala
 65                  70                  75                  80

Asn Ala Gly Asn Leu Glu Asp Leu Met Ser Asn Ile Thr Asn Arg Ser
             85                  90                  95

Asp Ile Asn Asp Thr Gly Phe Phe Met Asn Leu Glu Glu Asp Met Thr
           100                 105                 110

Arg Tyr Ala Tyr Tyr Ser Gly Ile Gly Ala Gly Val Leu Val Ala
       115                 120                 125

Ala Tyr Ile Gln Val Ser Phe Trp Cys Leu Ala Ala Gly Arg Gln Ile
   130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
               165                 170                 175

Asp Asp Val Ser Lys Ile Asn Glu Gly Ile Gly Asp Lys Ile Gly Met
           180                 185                 190

Phe Phe Gln Ser Met Ala Thr Phe Phe Thr Gly Phe Ile Val Gly Phe
       195                 200                 205

Thr Arg Gly Trp Lys Leu Thr Leu Val Ile Leu Ala Ile Ser Pro Val
   210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
               245                 250                 255

Val Leu Ala Ala Ile Arg Thr Val Ile Ala Phe Gly Gly Gln Lys Lys
           260                 265                 270

Glu Leu Glu Arg Tyr Asn Lys Asn Leu Glu Glu Ala Lys Arg Ile Gly
       275                 280                 285

Ile Lys Lys Ala Ile Thr Ala Asn Ile Ser Ile Gly Ala Ala Phe Leu
290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
               325                 330                 335

Ser Val Leu Ile Gly Ala Phe Ser Val Gly Gln Ala Ser Pro Ser Ile
           340                 345                 350

Glu Ala Phe Ala Asn Ala Arg Gly Ala Ala Tyr Glu Ile Phe Lys Ile
       355                 360                 365

Ile Asp Asn Lys Pro Ser Ile Asp Ser Tyr Ser Lys Ser Gly His Lys
   370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
               405                 410                 415

Val Gln Ser Gly Gln Thr Val Ala Leu Val Gly Asn Ser Gly Cys Gly
           420                 425                 430

Lys Ser Thr Thr Val Gln Leu Met Gln Arg Leu Tyr Asp Pro Thr Glu
       435                 440                 445

Gly Met Val Ser Val Asp Gly Gln Asp Ile Arg Thr Ile Asn Val Arg
   450                 455                 460

Phe Leu Arg Glu Ile Ile Gly Val Val Ser Gln Glu Pro Val Leu Phe
465                 470                 475                 480
```

-continued

```
Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
            500                 505                 510

Ile Met Lys Leu Pro His Lys Phe Asp Thr Leu Val Gly Glu Arg Gly
        515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590

Arg Asn Ala Asp Val Ile Ala Gly Phe Asp Asp Gly Val Ile Val Glu
        595                 600                 605

Lys Gly Asn His Asp Glu Leu Met Lys Glu Lys Gly Ile Tyr Phe Lys
    610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
        675                 680                 685

Asp Glu Ser Ile Pro Pro Val Ser Phe Trp Arg Ile Met Lys Leu Asn
    690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
            740                 745                 750

Asn Leu Phe Ser Leu Leu Phe Leu Ala Leu Gly Ile Ile Ser Phe Ile
        755                 760                 765

Thr Phe Phe Leu Gln Gly Phe Thr Phe Gly Lys Ala Gly Glu Ile Leu
    770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
            820                 825                 830

Leu Ala Val Ile Thr Gln Asn Ile Ala Asn Leu Gly Thr Gly Ile Ile
        835                 840                 845

Ile Ser Phe Ile Tyr Gly Trp Gln Leu Thr Leu Leu Leu Leu Ala Ile
    850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
```

```
                    900             905             910
Glu Gln Lys Phe Glu His Met Tyr Ala Gln Ser Leu Gln Val Pro Tyr
            915             920             925

Arg Asn Ser Leu Arg Lys Ala His Ile Phe Gly Ile Thr Phe Ser Phe
            930             935             940

Thr Gln Ala Met Met Tyr Phe Ser Tyr Ala Gly Cys Phe Arg Phe Gly
945             950             955             960

Ala Tyr Leu Val Ala His Lys Leu Met Ser Phe Glu Asp Val Leu Leu
                965             970             975

Val Phe Ser Ala Val Phe Gly Ala Met Ala Val Gly Gln Val Ser
                980             985             990

Ser Phe Ala Pro Asp Tyr Ala Lys Ala Lys Ile Ser Ala Ala His Ile
                995             1000            1005

Ile Met Ile Ile Glu Lys Thr Pro Leu Ile Asp Ser Tyr Ser Thr Glu
        1010            1015            1020

Gly Leu Met Pro Asn Thr Leu Glu Gly Asn Val Thr Phe Gly Glu Val
        1025            1030            1035            1040

Val Phe Asn Tyr Pro Thr Arg Pro Asp Ile Pro Val Leu Gln Gly Leu
                1045            1050            1055

Ser Leu Glu Val Lys Lys Gly Gln Thr Leu Ala Leu Val Gly Ser Ser
                1060            1065            1070

Gly Cys Gly Lys Ser Thr Val Val Gln Leu Leu Glu Arg Phe Tyr Asp
            1075            1080            1085

Pro Leu Ala Gly Lys Val Leu Leu Asp Gly Lys Glu Ile Lys Arg Leu
            1090            1095            1100

Asn Val Gln Trp Leu Arg Ala His Leu Gly Ile Val Ser Gln Glu Pro
1105            1110            1115            1120

Ile Leu Phe Asp Cys Ser Ile Ala Glu Asn Ile Ala Tyr Gly Asp Asn
                1125            1130            1135

Ser Arg Val Val Ser Gln Glu Glu Ile Val Arg Ala Ala Lys Glu Ala
                1140            1145            1150

Asn Ile His Ala Phe Ile Glu Ser Leu Pro Asn Lys Tyr Ser Thr Lys
        1155            1160            1165

Val Gly Asp Lys Gly Thr Gln Leu Ser Gly Gly Gln Lys Gln Arg Ile
    1170            1175            1180

Ala Ile Ala Arg Ala Leu Val Arg Gln Pro His Ile Leu Leu Leu Asp
1185            1190            1195            1200

Glu Ala Thr Ser Ala Leu Asp Thr Glu Ser Glu Lys Val Val Gln Glu
                1205            1210            1215

Ala Leu Asp Lys Ala Arg Glu Gly Arg Thr Cys Ile Val Ile Ala His
                1220            1225            1230

Arg Leu Ser Thr Ile Gln Asn Ala Asp Leu Ile Val Val Phe Gln Asn
        1235            1240            1245

Gly Arg Val Lys Glu His Gly Thr His Gln Gln Leu Leu Ala Gln Lys
    1250            1255            1260

Gly Ile Tyr Phe Ser Met Val Ser Val Gln Ala Gly Thr Lys Arg Gln
1265            1270            1275            1280
```

<210> SEQ ID NO 3
<211> LENGTH: 3860
<212> TYPE: DNA
<213> ORGANISM: Homo sapiens
<220> FEATURE:
<223> OTHER INFORMATION: Human MDR 185-V

```
<400> SEQUENCE: 3
atggatcttg aaggggaccg caatggagga gcaaagaaga agaactttt taaactgaac      60 aataaaagtg aaaagataa gaaggaaaag aaaccaactg tcagtgtatt ttcaatgttt     120
cgctattcaa attggcttga caagttgtat atggtggtgg gaactttggc tgccatcatc    180 catgggctg  gacttcctct catgatgctg gtgtttggag aaatgacaga tatctttgca    240
aatgcaggaa atttagaaga tctgatgtca acatcacta atagaagtga tatcaatgat    300
acagggttct tcatgaatct ggaggaagac atgaccagat atgcctatta ttacagtgga    360
attggtgctg gggtgctggt tgctgcttac attcaggttt catttggtg cctggcagct     420 ggaagacaaa tacacaaaat tagaaaacag ttttttcatg ctataatgcg acaggagata    480
ggctggtttg atgtgcacga tgttggggag cttaacaccc gacttacaga tgatgtctct    540
aagattaatg aagttattgg tgacaaaatt ggaatgttct ttcagtcaat ggcaacattt    600
ttcactgggt ttatagtagg atttacacgt ggttggaagc taaccttgt  gattttggcc    660 atcagtcctg ttcttggact gtcagctgct gtctgggcaa agatactatc ttcatttact    720
gataaagaac tcttagcgta tgcaaaagct ggagcagtag ctgaagaggt cttggcagca    780
attagaactg tgattgcatt tggaggacaa agaaagaac  ttgaaaggta caacaaaaat    840
ttagaagaag ctaaaagaat tgggataaag aaagctatta cagccaatat ttctataggt    900
gctgctttcc tgctgatcta tgcatcttat gctctggcct tctggtatgg gaccaccttg    960
gtcctctcag gggaatattc tattggacaa gtactcactg tattcttttc tgtattaatt   1020
ggggctttta gtgttggaca ggcatctcca agcattgaag catttgcaaa tgcaagagga   1080
gcagcttatg aaatcttcaa gataattgat aataagccaa gtattgacag ctattcgaag   1140
agtgggcaca accagataa  tattaaggga aatttggaat tcagaaatgt tcacttcagt   1200
tacccatctc gaaaagaagt taagatcttg aagggcctga acctgaaggt gcagagtggg   1260
cagacggtgg ccctggttgg aaacagtggc tgtgggaaga gcacaacagt ccagctgatg   1320
cagaggctct atgaccccac agaggggatg gtcagtgttg atggacagga tattaggacc   1380
ataaatgtaa ggtttctacg ggaaatcatt ggtgtggtga gtcaggaacc tgtattgttt   1440
gccaccacga tagctgaaaa cattcgctat ggccgtgaaa atgtcaccat ggatgagatt   1500
gagaaagctg tcaaggaagc caatgcctat gactttatca tgaaactgcc tcataaattt   1560
gacaccctgg ttggagagag aggggcccag ttgagtggtg ggcagaagca gaggatcgcc   1620
attgcacgtg ccctggttcg caaccccaag atcctcctgc tggatgaggc cacgtcagcc   1680
ttggacacag aaagcgaagc agtggttcag gtggctctgg ataaggccag aaaaggtcgg   1740
accaccattg tgatagctca tcgtttgtct acagttcgta atgctgacgt catcgctggt   1800
ttcgatgatg gagtcattgt ggagaaagga atcatgatg  aactcatgaa agagaaaggc   1860
atttacttca aacttgtcac aatgcagaca gcaggaaatg aagttgaatt agaaaatgca   1920
gctgatgaat ccaaaagtga aattgatgcc ttggaaatgt cttcaaatga ttcaagatcc   1980
agtctaataa gaaaaagatc aactcgtagg agtgtccgtg atcacaagc  ccaagacaga   2040 aagcttagta ccaaagaggc tctggatgaa gtatacctc cagtttcctt tggaggatt    2100 atgaagctaa atttaactga atggcctat  tttgttgttg gtgtattttg tgccattata   2160
aatggaggcc tgcaaccagc atttgcaata atattttcaa agattatagg ggtttttaca   2220
agaattgatg atcctgaaac aaaacgacag aatagtaact tgttttcact attgtttcta   2280
gcccttggaa ttatttcttt tattacattt ttccttcaag gtttcacatt tggcaaagct   2340
```

```
ggagagatcc tcaccaagcg gctccgatac atggttttcc gatccatgct cagacaggat   2400
gtgagttggt ttgatgaccc taaaaacacc actggagcat tgactaccag gctcgccaat   2460
gatgctgctc aagttaaagg ggctataggt tccaggcttg ctgtaattac ccagaatata   2520
gcaaatcttg gacaggaat aattatatcc ttcatctatg gttggcaact aacactgtta   2580
ctcttagcaa ttgtacccat cattgcaata gcaggagttg ttgaaatgaa atgttgtct   2640 ggacaagcac tgaaagataa gaaagaacta gaaggtgctg ggaagatcgc tactgaagca   2700
atagaaaact tccgaaccgt tgtttctttg actcaggagc agaagtttga acatatgtat   2760
gctcagagtt tgcaggtacc atacagaaac tctttgagga aagcacacat ctttggaatt   2820
acattttcct tcacccaggc aatgatgtat ttttcctatg ctggatgttt ccggtttgga   2880
gcctacttgg tggcacataa actcatgagc tttgaggatg ttctgttagt attttcagct   2940
gttgtctttg gtgccatggc cgtggggcaa gtcagttcat ttgctcctga ctatgccaaa   3000
gccaaaatat cagcagccca catcatcatg atcattgaaa aaacccctttt gattgacagc   3060 tacagcacgg aaggcctaat gccgaacaca ttggaaggaa atgtcacatt tggtgaagtt   3120
gtattcaact atcccaccc accggacatc ccagtgcttc agggactgag cctggaggtg   3180
aagaagggcc agacgctggc tctggtgggc agcagtggct gtgggaagag cacagtggtc   3240
cagctcctgg agcggttcta cgacccttg gcagggaaag tgctgcttga tgcaaagaa   3300 ataaagcgac tgaatgttca gtggctccga gcacacctgg gcatcgtgtc ccaggagccc   3360
atcctgtttg actgcagcat tgctgagaac attgcctatg gagacaacag ccgggtggtg   3420
tcacaggaag agatcgtgag ggcagcaaag gaggccaaca tacatgcctt catcgagtca   3480
ctgcctaata aatatagcac taaagtagga gacaaaggaa ctcagctctc tggtggccag   3540
aaacaacgca ttgccatagc tcgtgcccttt gttagacagc ctcatatttt gcttttggat   3600
gaagccacgt cagctctgga tacagaaagt gaaaaggttg tccaagaagc cctggacaaa   3660
gccagagaag gccgcacctg cattgtgatt gctcaccgcc tgtccaccat ccagaatgca   3720
gacttaatag tggtgtttca gaatggcaga gtcaaggagc atggcacgca tcagcagctg   3780
ctggcacaga aaggcatcta ttttcaatg gtcagtgtcc aggctggaac aaagcgccag   3840
tgaactctgg ttaactccac                                                3860
```

<210> SEQ ID NO 4
<211> LENGTH: 1280
<212> TYPE: PRT
<213> ORGANISM: Homo sapiens
<220> FEATURE:
<223> OTHER INFORMATION: Human MDR 185-V

<400> SEQUENCE: 4

```
Met Asp Leu Glu Gly Asp Arg Asn Gly Gly Ala Lys Lys Lys Asn Phe
 1               5                  10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95
```

```
Asp Ile Asn Asp Thr Gly Phe Phe Met Asn Leu Glu Glu Asp Met Thr
            100                 105                 110

Arg Tyr Ala Tyr Tyr Ser Gly Ile Gly Ala Gly Val Leu Val Ala
            115                 120                 125

Ala Tyr Ile Gln Val Ser Phe Trp Cys Leu Ala Ala Gly Arg Gln Ile
        130                 135                 140

His Lys Ile Arg Lys Gln Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Val Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
            245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
            325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
        355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
            405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
        435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
            485                 490                 495

Met Asp Glu Ile Glu Lys Ala Val Lys Glu Ala Asn Ala Tyr Asp Phe
            500                 505                 510
```

```
Ile Met Lys Leu Pro His Lys Phe Asp Thr Leu Val Gly Glu Arg Gly
        515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
                580                 585                 590

Arg Asn Ala Asp Val Ile Ala Gly Phe Asp Asp Gly Val Ile Val Glu
            595                 600                 605

Lys Gly Asn His Asp Glu Leu Met Lys Glu Lys Gly Ile Tyr Phe Lys
        610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
        675                 680                 685

Asp Glu Ser Ile Pro Pro Val Ser Phe Trp Arg Ile Met Lys Leu Asn
    690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
            740                 745                 750

Asn Leu Phe Ser Leu Leu Phe Leu Ala Leu Gly Ile Ile Ser Phe Ile
        755                 760                 765

Thr Phe Phe Leu Gln Gly Phe Thr Phe Gly Lys Ala Gly Glu Ile Leu
    770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
            820                 825                 830

Leu Ala Val Ile Thr Gln Asn Ile Ala Asn Leu Gly Thr Gly Ile Ile
        835                 840                 845

Ile Ser Phe Ile Tyr Gly Trp Gln Leu Thr Leu Leu Leu Leu Ala Ile
    850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
        915                 920                 925

Arg Asn Ser Leu Arg Lys Ala His Ile Phe Gly Ile Thr Phe Ser Phe
```

```
                930              935              940
Thr Gln Ala Met Met Tyr Phe Ser Tyr Ala Gly Cys Phe Arg Phe Gly
945                      950                  955                  960

Ala Tyr Leu Val Ala His Lys Leu Met Ser Phe Glu Asp Val Leu Leu
                 965                  970                  975

Val Phe Ser Ala Val Val Phe Gly Ala Met Ala Val Gly Gln Val Ser
                 980                  985                  990

Ser Phe Ala Pro Asp Tyr Ala Lys Ala Lys Ile Ser Ala Ala His Ile
            995                  1000                 1005

Ile Met Ile Ile Glu Lys Thr Pro Leu Ile Asp Ser Tyr Ser Thr Glu
        1010                 1015                 1020

Gly Leu Met Pro Asn Thr Leu Glu Gly Asn Val Thr Phe Gly Glu Val
1025                 1030                 1035                 1040

Val Phe Asn Tyr Pro Thr Arg Pro Asp Ile Pro Val Leu Gln Gly Leu
                 1045                 1050                 1055

Ser Leu Glu Val Lys Lys Gly Gln Thr Leu Ala Leu Val Gly Ser Ser
            1060                 1065                 1070

Gly Cys Gly Lys Ser Thr Val Val Gln Leu Leu Glu Arg Phe Tyr Asp
        1075                 1080                 1085

Pro Leu Ala Gly Lys Val Leu Leu Asp Gly Lys Glu Ile Lys Arg Leu
        1090                 1095                 1100

Asn Val Gln Trp Leu Arg Ala His Leu Gly Ile Val Ser Gln Glu Pro
1105                 1110                 1115                 1120

Ile Leu Phe Asp Cys Ser Ile Ala Glu Asn Ile Ala Tyr Gly Asp Asn
                 1125                 1130                 1135

Ser Arg Val Val Ser Gln Glu Glu Ile Val Arg Ala Ala Lys Glu Ala
            1140                 1145                 1150

Asn Ile His Ala Phe Ile Glu Ser Leu Pro Asn Lys Tyr Ser Thr Lys
        1155                 1160                 1165

Val Gly Asp Lys Gly Thr Gln Leu Ser Gly Gly Gln Lys Gln Arg Ile
        1170                 1175                 1180

Ala Ile Ala Arg Ala Leu Val Arg Gln Pro His Ile Leu Leu Leu Asp
1185                 1190                 1195                 1200

Glu Ala Thr Ser Ala Leu Asp Thr Glu Ser Glu Lys Val Val Gln Glu
                 1205                 1210                 1215

Ala Leu Asp Lys Ala Arg Glu Gly Arg Thr Cys Ile Val Ile Ala His
            1220                 1225                 1230

Arg Leu Ser Thr Ile Gln Asn Ala Asp Leu Ile Val Val Phe Gln Asn
        1235                 1240                 1245

Gly Arg Val Lys Glu His Gly Thr His Gln Gln Leu Leu Ala Gln Lys
        1250                 1255                 1260

Gly Ile Tyr Phe Ser Met Val Ser Val Gln Ala Gly Thr Lys Arg Gln
1265                 1270                 1275                 1280

<210> SEQ ID NO 5
<211> LENGTH: 4189
<212> TYPE: DNA
<213> ORGANISM: Mus musculus
<220> FEATURE:
<223> OTHER INFORMATION: Mouse MDR-1

<400> SEQUENCE: 5
atggagtttg aagagaacct taagggaaga gcagacaaga acttctcgaa gatgggcaaa      60
aagagtaaaa aggagaagaa agaaaagaaa cctgctgttg gcgtatttgg gatgtttcgc     120
```

```
tatgcagatt ggctggacaa gctgtgcatg attctgggaa ctctcgctgc tattatccat    180
ggaacattac ttccctctt gatgctggtg tttggaaaca tgacagatag ttttacaaaa    240
gcagaagcca gtattctgcc aagcattact aatcaaagtg acccaacag tactctgatc    300 atcagcaaca gcagtctgga ggaagagatg gccatatacg cctactatta caccgggatt    360
ggtgctggtg tgctcatagt tgcctacatc caggtttcac tttggtgcct ggcagctgga    420
agacagatac acaagattag gcagaagttt ttccatgcta taatgaatca ggagataggc    480
tggtttgatg tgcatgatgt tggggagctc aacacccggc tcacagatga tgtctccaaa    540
attaatgacg gaattggtga caaaattggg atgttttttc agtccataac cacattttta    600
gccggtttta tcataggatt tataagtggt tggaagctaa cccttgtcat tttggctgtc    660
agccctctta ttgattgtc atctgctttg tgggcaaagg tattgacttc atttactaat    720
aaggaactcc aggcttatgc aaaagctgga gcagttgctg aagaagtctt agcagccatc    780
agaactgtga ttgcctttgg aggacaacag aaggaacttg aaaggtacaa taaaaattta    840
gaagaagcta aaaatgttgg cataaagaaa gctatcacag ccagcatttc gataggcatt    900
gcctacctgt tggtctatgc atcatatgca ctggcattct ggtatgggac atccttggtc    960
ctctcaaatg aatattctat tggagaagtg cttactgtct tcttctctat tttgttgggg   1020
acttttagta ttggacactt ggccccaaac atagaagcct tgcaaacgc acgaggggca   1080 gcctttgaaa tcttcaagat aattgataac gagccaagca ttgacagctt ctcaacaaag   1140
ggctacaaac cagacagtat aatgggaaac ttagagttta aaaatgttca cttcaactac   1200
ccatcgagaa gcgaagttca gatcttgaag ggcctcaatc tgaaggtgaa gagcggacag   1260
acggtggcct tggttggcaa cagtggctgt ggaaaaagca caactgtcca gctgatgcag   1320
aggctctacg acccctgga gggcgtggtc agtatcgacg acaagacat cagaaccatc   1380 aatgtgaggt atctgaggga gatcattggt gtggtgagtc aggaacctgt gctgtttgcc   1440
accacgatcg ccgagaacat tcgctatggc cgagaagatg tcaccatgga tgagattgag   1500
aaagctgtca aggaagccaa tgcctatgac ttcatcatga actgccca ccaatttgac   1560 accctggttg gtgagagagg ggcgcagctg agtggggac agaaacagag aatcgccatt   1620
gcccgggccc tggtccgcaa tcccaagatc cttttgttgg acgaggccac ctcagccctg   1680
gatacagaaa gtgaagctgt ggtgcaggcc gcactggata aggctagaga aggccggacc   1740
accattgtga tagctcatcg cttgtctaca gttcgtaatg ctgacgtcat tgctggtttt   1800
gatggtggtg tcattgtgga gcaaggaaat catgatgagc tcatgagaga aaagggcatt   1860
tacttcaaac ttgtcatgac acagactaga ggaaatgaaa ttgaaccagg aaataatgct   1920
tatggatccc agagtgacac tgatgcttct gaactgactt cagaagaatc caaatcacct   1980
ttaataagga gatcaattta cagaagtgtc cacagaaagc aagaccaaga gagaagactt   2040
agtatgaaag aggctgtgga tgaagatgtg cctctggttt cctttggcg gatcctaaat   2100 ctaaatctaa gtgaatggcc ttatttactt gttggcgtac tttgcgctgt tataaatggg   2160
tgcatacaac cagtgtttgc catagtattt tcaaggattg taggggtttt ttcaagagat   2220
gatgaccatg aaactaaacg acagaattgt aatttgtttt ccctgttctt tctggttatg   2280
gggctgattt cttttgttac atatttcttt cagggcttca catttggcaa agccggagag   2340
atcctcacca agcgagtccg atacatggtt ttcaaatcca tgctgagaca ggatataagc   2400
tggttcgatg accataagaa cagcactggc tcactgacca ccaggctcgc cagtgatgct   2460
tctagtgtta aaggggcgat gggcgccagg cttgctgtag ttacccagaa tgtagcaaac   2520
```

-continued

```
ctcgggacag gagtcatcct ctccttagtc tatggctggc agctgacact tctacttgta    2580
gtaattatac cgctcattgt attgggcgga attattgaaa tgaagctgtt gtctggccaa    2640
gccttgaagg acaagaaaca gcttgagatc tctgggaaga ttgctacaga agcaattgaa    2700
aacttccgca ctattgtctc tttgactcgg gagcagaagt ttgaaaccat gtatgcccag    2760
agcttgcagg taccatacag aaatgcgatg aagaaagcac acgtgtttgg gatcacgttc    2820
tccttcaccc aggccatgat gtattttct  tatgctgctt gtttccggtt cggtgcctac    2880
ttggtggcac aacaactcat gacttttgaa aatgttatgt tggtattttc tgctgttgtc    2940
tttggtgcca tggcagctgg gaatactagt tcatttgctc ctgactatgc gaaagccaaa    3000
gtatcagcat ctcatatcat caggatcatt gagaaaaccc ctgagattga cagctacagc    3060
acagagggct tgaagcctac tctgttagaa ggaaatgtaa aatttaatgg agtccagttt    3120
aactatccca cccgacccaa catcccagtg cttcaggggc tgagcctcga ggtgaagaag    3180
ggccagacgt tggccctggt gggcagcagt ggctgtggga gagcacagt  ggtccagctg    3240 ctcgagcgct tctacgaccc catggctgga tcagtgtttc tagatggcaa agaaataaag    3300
caactgaatg tccagtggct ccgagctcac cttggcattg tgtcccagga gcccattctc    3360
tttgactgca gcattgcaga gaacatcgcc tatggagaca cagccgggc  cgtgtctcat    3420 gaggagattg tgagggcagc caaggaggcc aacatccacc agttcatcga ctcactgcct    3480
gataaataca acaccagagt aggagacaaa ggcactcagc tgtcgggtgg gcagaagcag    3540
cgcatcgcca tcgcacgtgc cctcgtcaga cagcctcaca ttttacttct ggacgaagca    3600
acatcagctc tggatacaga aagtgaaaag gttgtccagg aagcgctgga caaagccagg    3660
gaaggccgca cctgcattgt gatcgctcac cgcctgtcca ccatccagaa cgcggacttg    3720
atcgtggtga ttgagaacgg caaagtcaag gagcacggca cccaccagca gctgctggcg    3780
cagaagggca tctacttctc aatggtccag gctggagcaa agcgctcatg agctgtgact    3840
atctgaggtg ctaagtattt ttaatattgg tgtttaaaca tggcaccaaa ccaaagttaa    3900
aaggcaaggc tgttaaagg  taactccatc aagatgagaa gccttccgag actttgtaat    3960
taaatgaacc aaaatcggaa acaaacaaac aaacaaacaa acaagccata gttaaacagg    4020 gccatgttt  taattgcatt acgtgattca taagagaaca tatagttttt taaaataaaa    4080
tgtataattt tgtttcagtt tttaatttct accctacttt cttaaatgat tataaagatt    4140
gtaaaaagca ctatttctta aattgcctat aaaaattaaa ttttcatat               4189
```

<210> SEQ ID NO 6
<211> LENGTH: 1276
<212> TYPE: PRT
<213> ORGANISM: Mus musculus
<220> FEATURE:
<223> OTHER INFORMATION: Mouse MDR-1

<400> SEQUENCE: 6

```
Met Glu Phe Glu Glu Asn Leu Lys Gly Arg Ala Asp Lys Asn Phe Ser
 1               5                  10                  15

Lys Met Gly Lys Lys Ser Lys Lys Glu Lys Lys Glu Lys Lys Pro Ala
            20                  25                  30

Val Gly Val Phe Gly Met Phe Arg Tyr Ala Asp Trp Leu Asp Lys Leu
        35                  40                  45

Cys Met Ile Leu Gly Thr Leu Ala Ala Ile Ile His Gly Thr Leu Leu
    50                  55                  60
```

-continued

```
Pro Leu Leu Met Leu Val Phe Gly Asn Met Thr Asp Ser Phe Thr Lys
 65                  70                  75                  80

Ala Glu Ala Ser Ile Leu Pro Ser Ile Thr Asn Gln Ser Gly Pro Asn
                 85                  90                  95

Ser Thr Leu Ile Ile Ser Asn Ser Ser Leu Glu Glu Met Ala Ile
            100                 105                 110

Tyr Ala Tyr Tyr Tyr Thr Gly Ile Gly Ala Gly Val Leu Ile Val Ala
            115                 120                 125

Tyr Ile Gln Val Ser Leu Trp Cys Leu Ala Ala Gly Arg Gln Ile His
        130                 135                 140

Lys Ile Arg Gln Lys Phe Phe His Ala Ile Met Asn Gln Glu Ile Gly
145                 150                 155                 160

Trp Phe Asp Val His Asp Val Gly Glu Leu Asn Thr Arg Leu Thr Asp
                165                 170                 175

Asp Val Ser Lys Ile Asn Asp Gly Ile Gly Asp Lys Ile Gly Met Phe
            180                 185                 190

Phe Gln Ser Ile Thr Thr Phe Leu Ala Gly Phe Ile Ile Gly Phe Ile
        195                 200                 205

Ser Gly Trp Lys Leu Thr Leu Val Ile Leu Ala Val Ser Pro Leu Ile
210                 215                 220

Gly Leu Ser Ser Ala Leu Trp Ala Lys Val Leu Thr Ser Phe Thr Asn
225                 230                 235                 240

Lys Glu Leu Gln Ala Tyr Ala Lys Ala Gly Ala Val Ala Glu Glu Val
                245                 250                 255

Leu Ala Ala Ile Arg Thr Val Ile Ala Phe Gly Gly Gln Gln Lys Glu
            260                 265                 270

Leu Glu Arg Tyr Asn Lys Asn Leu Glu Glu Ala Lys Asn Val Gly Ile
        275                 280                 285

Lys Lys Ala Ile Thr Ala Ser Ile Ser Ile Gly Ile Ala Tyr Leu Leu
290                 295                 300

Val Tyr Ala Ser Tyr Ala Leu Ala Phe Trp Tyr Gly Thr Ser Leu Val
305                 310                 315                 320

Leu Ser Asn Glu Tyr Ser Ile Gly Glu Val Leu Thr Val Phe Phe Ser
                325                 330                 335

Ile Leu Leu Gly Thr Phe Ser Ile Gly His Leu Ala Pro Asn Ile Glu
            340                 345                 350

Ala Phe Ala Asn Ala Arg Gly Ala Ala Phe Glu Ile Phe Lys Ile Ile
        355                 360                 365

Asp Asn Glu Pro Ser Ile Asp Ser Phe Ser Thr Lys Gly Tyr Lys Pro
370                 375                 380

Asp Ser Ile Met Gly Asn Leu Glu Phe Lys Asn Val His Phe Asn Tyr
385                 390                 395                 400

Pro Ser Arg Ser Glu Val Gln Ile Leu Lys Gly Leu Asn Leu Lys Val
                405                 410                 415

Lys Ser Gly Gln Thr Val Ala Leu Val Gly Asn Ser Gly Cys Gly Lys
            420                 425                 430

Ser Thr Thr Val Gln Leu Met Gln Arg Leu Tyr Asp Pro Leu Glu Gly
        435                 440                 445

Val Val Ser Ile Asp Gly Gln Asp Ile Arg Thr Ile Asn Val Arg Tyr
450                 455                 460

Leu Arg Glu Ile Ile Gly Val Val Ser Gln Glu Pro Val Leu Phe Ala
465                 470                 475                 480

Thr Thr Ile Ala Glu Asn Ile Arg Tyr Gly Arg Glu Asp Val Thr Met
```

-continued

```
                485                 490                 495
Asp Glu Ile Glu Lys Ala Val Lys Glu Asn Ala Tyr Asp Phe Ile
                500                 505                 510

Met Lys Leu Pro His Gln Phe Asp Thr Leu Val Gly Glu Arg Gly Ala
                515                 520                 525

Gln Leu Ser Gly Gly Gln Lys Gln Arg Ile Ala Ile Ala Arg Ala Leu
                530                 535                 540

Val Arg Asn Pro Lys Ile Leu Leu Leu Asp Glu Ala Thr Ser Ala Leu
545                 550                 555                 560

Asp Thr Glu Ser Glu Ala Val Val Gln Ala Ala Leu Asp Lys Ala Arg
                565                 570                 575

Glu Gly Arg Thr Thr Ile Val Ile Ala His Arg Leu Ser Thr Val Arg
                580                 585                 590

Asn Ala Asp Val Ile Ala Gly Phe Asp Gly Gly Val Ile Val Glu Gln
                595                 600                 605

Gly Asn His Asp Glu Leu Met Arg Glu Lys Gly Ile Tyr Phe Lys Leu
                610                 615                 620

Val Met Thr Gln Thr Arg Gly Asn Glu Ile Glu Pro Gly Asn Asn Ala
625                 630                 635                 640

Tyr Gly Ser Gln Ser Asp Thr Asp Ala Ser Glu Leu Thr Ser Glu Glu
                645                 650                 655

Ser Lys Ser Pro Leu Ile Arg Arg Ser Ile Tyr Arg Ser Val His Arg
                660                 665                 670

Lys Gln Asp Gln Glu Arg Arg Leu Ser Met Lys Glu Ala Val Asp Glu
                675                 680                 685

Asp Val Pro Leu Val Ser Phe Trp Arg Ile Leu Asn Leu Asn Leu Ser
                690                 695                 700

Glu Trp Pro Tyr Leu Leu Val Gly Val Leu Cys Ala Val Ile Asn Gly
705                 710                 715                 720

Cys Ile Gln Pro Val Phe Ala Ile Val Phe Ser Arg Ile Val Gly Val
                725                 730                 735

Phe Ser Arg Asp Asp Asp His Glu Thr Lys Arg Gln Asn Cys Asn Leu
                740                 745                 750

Phe Ser Leu Phe Phe Leu Val Met Gly Leu Ile Ser Phe Val Thr Tyr
                755                 760                 765

Phe Phe Gln Gly Phe Thr Phe Gly Lys Ala Gly Glu Ile Leu Thr Lys
                770                 775                 780

Arg Val Arg Tyr Met Val Phe Lys Ser Met Leu Arg Gln Asp Ile Ser
785                 790                 795                 800

Trp Phe Asp Asp His Lys Asn Ser Thr Gly Ser Leu Thr Thr Arg Leu
                805                 810                 815

Ala Ser Asp Ala Ser Val Lys Gly Ala Met Gly Ala Arg Leu Ala
                820                 825                 830

Val Val Thr Gln Asn Val Ala Asn Leu Gly Thr Gly Val Ile Leu Ser
                835                 840                 845

Leu Val Tyr Gly Trp Gln Leu Thr Leu Leu Val Val Ile Ile Pro
                850                 855                 860

Leu Ile Val Leu Gly Gly Ile Ile Glu Met Lys Leu Leu Ser Gly Gln
865                 870                 875                 880

Ala Leu Lys Asp Lys Lys Gln Leu Glu Ile Ser Gly Lys Ile Ala Thr
                885                 890                 895

Glu Ala Ile Glu Asn Phe Arg Thr Ile Val Ser Leu Thr Arg Glu Gln
                900                 905                 910
```

-continued

```
Lys Phe Glu Thr Met Tyr Ala Gln Ser Leu Gln Val Pro Tyr Arg Asn
            915                 920                 925
Ala Met Lys Ala His Val Phe Gly Ile Thr Phe Ser Phe Thr Gln
        930                 935                 940
Ala Met Met Tyr Phe Ser Tyr Ala Ala Cys Phe Arg Phe Gly Ala Tyr
945                 950                 955                 960
Leu Val Ala Gln Gln Leu Met Thr Phe Glu Asn Val Met Leu Val Phe
                965                 970                 975
Ser Ala Val Val Phe Gly Ala Met Ala Ala Gly Asn Thr Ser Ser Phe
            980                 985                 990
Ala Pro Asp Tyr Ala Lys Ala Lys Val Ser Ala Ser His Ile Ile Arg
        995                 1000                1005
Ile Ile Glu Lys Thr Pro Glu Ile Asp Ser Tyr Ser Thr Glu Gly Leu
    1010                1015                1020
Lys Pro Thr Leu Leu Glu Gly Asn Val Lys Phe Asn Gly Val Gln Phe
1025                1030                1035                1040
Asn Tyr Pro Thr Arg Pro Asn Ile Pro Val Leu Gln Gly Leu Ser Leu
            1045                1050                1055
Glu Val Lys Lys Gly Gln Thr Leu Ala Leu Val Gly Ser Ser Gly Cys
        1060                1065                1070
Gly Lys Ser Thr Val Val Gln Leu Leu Glu Arg Phe Tyr Asp Pro Met
    1075                1080                1085
Ala Gly Ser Val Phe Leu Asp Gly Lys Glu Ile Lys Gln Leu Asn Val
        1090                1095                1100
Gln Trp Leu Arg Ala His Leu Gly Ile Val Ser Gln Glu Pro Ile Leu
1105                1110                1115                1120
Phe Asp Cys Ser Ile Ala Glu Asn Ile Ala Tyr Gly Asp Asn Ser Arg
            1125                1130                1135
Ala Val Ser His Glu Glu Ile Val Arg Ala Ala Lys Glu Ala Asn Ile
            1140                1145                1150
His Gln Phe Ile Asp Ser Leu Pro Asp Lys Tyr Asn Thr Arg Val Gly
        1155                1160                1165
Asp Lys Gly Thr Gln Leu Ser Gly Gly Gln Lys Gln Arg Ile Ala Ile
    1170                1175                1180
Ala Arg Ala Leu Val Arg Gln Pro His Ile Leu Leu Leu Asp Glu Ala
1185                1190                1195                1200
Thr Ser Ala Leu Asp Thr Glu Ser Glu Lys Val Val Gln Glu Ala Leu
            1205                1210                1215
Asp Lys Ala Arg Glu Gly Arg Thr Cys Ile Val Ile Ala His Arg Leu
        1220                1225                1230
Ser Thr Ile Gln Asn Ala Asp Leu Ile Val Val Ile Glu Asn Gly Lys
    1235                1240                1245
Val Lys Glu His Gly Thr His Gln Gln Leu Leu Ala Gln Lys Gly Ile
        1250                1255                1260
Tyr Phe Ser Met Val Gln Ala Gly Ala Lys Arg Ser
1265                1270                1275
```

<210> SEQ ID NO 7
<211> LENGTH: 4788
<212> TYPE: DNA
<213> ORGANISM: Mus musculus
<220> FEATURE:
<223> OTHER INFORMATION: Mouse MDR-3

<400> SEQUENCE: 7

-continued

```
atggaacttg aagaggacct taagggaaga gcagacaaga acttctcaaa gatgggcaaa      60
aagagtaaaa aggagaagaa agaaaagaaa ccagcagtca gtgtgcttac aatgtttcgt     120
tatgcaggtt ggctagacag gttgtacatg ctggtgggaa ctctggctgc tattatccat     180
ggagtggcgc tcccacttat gatgctgatc tttggtgaca tgacagatag ctttgcaagt     240
gtaggaaacg tctctaaaaa cagtactaat atgagtgagg ccgataaaag agccatgttt     300
gccaaactgg aggaagaaat gaccacgtac gcctactatt acaccgggat tggtgctggt     360
gtgctcatag ttgcctacat ccaggtttca ttttggtgcc tggcagctgg aagacagata     420
cacaagatca ggcagaagtt ttttcatgct ataatgaatc aggagatagg ctggtttgat     480
gtgcatgacg ttggggagct caacacccgg ctcacagatg atgtttccaa aattaatgaa     540
ggaattggtg acaaaatcgg aatgttcttc caggcaatgg caacattttt tggtggtttt     600
ataataggat ttacccgtgg ctggaagcta acccttgtga ttttggccat cagccctgtt     660
cttggactgt cagctggtat ttgggcaaag atattgtctt catttactga taaggaactc     720
catgcttatg caaagctggg agcagttgct gaagaagtct tagcagccat cagaactgtg     780
attgcgtttg gaggacaaaa gaaggaactt gaaaggtaca ataacaactt ggaagaagct     840
aaaaggctgg ggataaagaa agctatcacg gccaacatct ccatgggtgc agcttttctc     900
cttatctatg catcatatgc tctggcattc tggtatggga cttccttggt catctccaaa     960
gaatactcta ttggacaagt gctcactgtc ttcttttccg tgttaattgg agcattcagt    1020
gttggacagg catctccaaa tattgaagcc ttcgccaatg cacgaggagc agcttatgaa    1080
gtcttcaaaa taattgataa taagcccagt atagacagct ctcaaagag tgggcacaaa    1140
ccagacaaca tacaaggaaa tctggaattt aagaatattc acttcagtta cccatctcga    1200
aaagaagttc agatcttgaa gggcctcaat ctgaaggtga agagcggaca gacggtggcc    1260
ctggttggca acagtggctg tggaaaaagc acaactgtcc agctgatgca aaggctctac    1320
gaccccctag atggcatggt cagtatcgac ggacaggaca tcagaaccat caatgtgagg    1380
tatctgaggg agatcattgg tgtggtgagt caggaacctg tgctgtttgc caccacgatc    1440
gccgagaaca ttcgctatgg ccgagaagat gtcaccatgg atgagattga aaagctgtc     1500
aaggaagcca atgcctatga cttcatcatg aaactgcccc accaatttga caccctggtt    1560
ggtgagagag gggcgcacgt gagtggggga cagaaacaga gaatcgccat tgcccgggcc    1620
ctggtccgca atcccaagat ccttttgttg gacgaggcca cctcagccct ggatacagaa    1680
agtgaagctg tggttcaggc cgcactggat aaggctagag aaggccggac caccattgtg    1740
atagctcatc gcttgtctac cgttcgtaat gctgacgtca ttgctggttt tgatggtggt    1800
gtcattgtgg agcaaggaaa tcatgatgag ctcatgagag aaaagggcat ttacttcaaa    1860
cttgtcatga cacagacagc aggaaatgaa attgaattag gaaatgaagc ttgtaaatct    1920
aaggatgaaa ttgataattt agacatgtct tcaaaagatt caggatccag tctaataaga    1980
agaagatcaa ctcgcaaaag catctgtgga ccacatgacc aagacaggaa gcttagtacc    2040
aaagaggccc tggatgaaga tgtacctcca gcttcctttt ggcggatcct gaagttgaat    2100
tcaactgaat ggccttattt tgtggttggt atattctgtg ccataataaa tggaggctta    2160
cagccagcat tctccgtaat attttcaaaa gttgtagggg ttttacaaaa tggtggcccc    2220
cctgaaaccc agcggcagaa cagcaacttg ttttccttgt tgtttctgat ccttgggatc    2280
atttctttca ttacatttt tcttcagggc ttcacatttg gcaaagctgg agagatcctc    2340
```

-continued

```
accaagcgac tccgatacat ggttttcaaa tccatgctga dacaggatgt gagctggttt    2400
gatgacccta aaaacaccac cggagcactg accaccaggc tcgccaacga tgctgctcaa    2460
gtgaaagggg ctacagggtc taggcttgct gtgattttcc agaacatagc aaatcttggg    2520
acaggaatca tcatatccct aatctatggc tggcaactaa cacttttact cttagcaatt    2580
gtacccatca ttgcgatagc tggagtggtt gaaatgaaaa tgttgtctgg acaagcactg    2640
aaagataaga aggaactaga aggttctgga aagattgcta cggaagcaat tgaaaacttc    2700
cgcactgttg tctctttgac tcgggagcag aagtttgaaa ccatgtatgc ccagagcttg    2760
cagataccat acagaaatgc gatgaagaaa gcacacgtgt ttgggatcac gttctccttc    2820
acccaggcca tgatgtattt ttcttatgct gcttgtttcc ggttcggtgc ctacttggtg    2880
acacaacaac tcatgacttt tgaaaatgtt ctgttagtat tctcagctat tgtctttggt    2940
gccatggcag tggggcaggt cagttcattc gctcctgact atgcgaaagc aacagtgtca    3000
gcatcccaca tcatcaggat cattgagaaa acccccgaga ttgacagcta cagcacgcaa    3060
ggcctaaagc cgaatatgtt ggaaggaaat gtgcaattta gtggagtcgt gttcaactat    3120
cccacccgac ccagcatccc agtgcttcag gggctgagcc ttgaggtgaa gaagggccag    3180
acgctggccc tggtgggcag cagtggctgc gggaagagca cagtggtcca gctgctcgag    3240
cgcttctacg acccccatgg ctggatcagt tttctagatg gcaaagaaat aaagcaactg    3300
aatgtccagt ggctccgagc acagctgggc attgtgtccc aagagcccat tctctttgac    3360
tgcagcatcg cagagaacat tgcctacgga gacaacagcc gggtcgtgtc ttatgaggag    3420
attgtgaggg cagccaagga ggccaacatc caccagttca tcgactcgct acctgataaa    3480
tacaacacca gagtaggaga caaaggcact cagctgtcgg gtgggcagaa gcagcgcatc    3540
gccatcgcac gcgccctcgt cagacagcct cacattttac ttctggacga agcaacatca    3600
gctctggata cagaaagtga aaaggttgtc caggaagcgc tggacaaagc cagggaaggc    3660
cgcacctgca ttgtgatcgc tcaccgcctg tccaccatcc agaacgcgga cttgatcgtg    3720
gtgattcaga acggcaaggt caaggagcac ggcacccacc agcagctgct ggcgcagaag    3780
ggcatctact tctcaatggt cagtgtgcag gctggagcaa agcgctcatg aactgtgacc    3840
atgtaagatg ttaagtattt ttattgtttg tattcatata tggtgtttaa tccaagtcaa    3900
aaggaaaaca cttactaaaa tagccagtta tctattttct gccacagtgg aaagcattta    3960
gtttggttta gagtcttcag aggctttgta attaaaaaaa caaaaataga tacagcatca    4020
aatggagatt aatgctttaa aatgcactat aaaatttata aaagggttaa aagtgaatgt    4080
ttgataatat atacttttat ttatactttc tcatttgtaa ctataactga tttctgctta    4140
acaaattatg tatgtatcaa aaattactga aatgttgta taaagtatat atagtgaaac    4200
tgagcattca tattttttgag ttattttgct caaatgcatg cgaaattata tattgtccca    4260
actgggatat tgtacataat tttagccttt aaaaaacagt ccattactgg ggggagggg    4320
catcactcta tgggcaaagt gttactcaga catgggcacc tgagttcaga tccctaccac    4380
ctaagtaagc agacaaggtg tggtgttttt gtaatgccag tgctagaggc agaaaagaca    4440
gatcctgcag gctcagtggc tggccaaaca gcctagccaa catagcgcgt tccaggttca    4500
gtgagaaaac ttgtctcaaa aatcagaggg aaaagcaaat gaggtgtcag ccatgtgcac    4560
tcatgcaaat gccatacatg cagaagtatg tgcacacaca cgcacacatt aaccaacgac    4620
tagcaaggaa aatgaaggtg gataagaggg gtgggactgg gacaaaggag ggtacctgga    4680
tgaatatgac tgaaggacgt tatgtacaca tatgaaaacg tcgtactgaa actcactaca    4740
```

-continued

```
atgtatactt aatatattgc taataaaata tttttaaaag aaaaaaat          4788
```

<210> SEQ ID NO 8
<211> LENGTH: 1276
<212> TYPE: PRT
<213> ORGANISM: Mus musculus
<220> FEATURE:
<223> OTHER INFORMATION: Mouse MDR-3

<400> SEQUENCE: 8

```
Met Glu Leu Glu Glu Asp Leu Lys Gly Arg Ala Asp Lys Asn Phe Ser
  1               5                  10                  15

Lys Met Gly Lys Lys Ser Lys Lys Glu Lys Lys Pro Ala
                 20                  25                  30

Val Ser Val Leu Thr Met Phe Arg Tyr Ala Gly Trp Leu Asp Arg Leu
             35                  40                  45

Tyr Met Leu Val Gly Thr Leu Ala Ala Ile Ile His Gly Val Ala Leu
     50                  55                  60

Pro Leu Met Met Leu Ile Phe Gly Asp Met Thr Asp Ser Phe Ala Ser
 65                  70                  75                  80

Val Gly Asn Val Ser Lys Asn Ser Thr Asn Met Ser Glu Ala Asp Lys
                 85                  90                  95

Arg Ala Met Phe Ala Lys Leu Glu Glu Met Thr Thr Tyr Ala Tyr
            100                 105                 110

Tyr Tyr Thr Gly Ile Gly Ala Gly Val Leu Ile Val Ala Tyr Ile Gln
        115                 120                 125

Val Ser Phe Trp Cys Leu Ala Ala Gly Arg Gln Ile His Lys Ile Arg
130                 135                 140

Gln Lys Phe Phe His Ala Ile Met Asn Gln Glu Ile Gly Trp Phe Asp
145                 150                 155                 160

Val His Asp Val Gly Glu Leu Asn Thr Arg Leu Thr Asp Asp Val Ser
                165                 170                 175

Lys Ile Asn Glu Gly Ile Gly Asp Lys Ile Gly Met Phe Phe Gln Ala
            180                 185                 190

Met Ala Thr Phe Phe Gly Gly Phe Ile Ile Gly Phe Thr Arg Gly Trp
        195                 200                 205

Lys Leu Thr Leu Val Ile Leu Ala Ile Ser Pro Val Leu Gly Leu Ser
    210                 215                 220

Ala Gly Ile Trp Ala Lys Ile Leu Ser Ser Phe Thr Asp Lys Glu Leu
225                 230                 235                 240

His Ala Tyr Ala Lys Ala Gly Ala Val Ala Glu Glu Val Leu Ala Ala
                245                 250                 255

Ile Arg Thr Val Ile Ala Phe Gly Gly Gln Lys Lys Glu Leu Glu Arg
            260                 265                 270

Tyr Asn Asn Asn Leu Glu Glu Ala Lys Arg Leu Gly Ile Lys Lys Ala
        275                 280                 285

Ile Thr Ala Asn Ile Ser Met Gly Ala Ala Phe Leu Leu Ile Tyr Ala
    290                 295                 300

Ser Tyr Ala Leu Ala Phe Trp Tyr Gly Thr Ser Leu Val Ile Ser Lys
305                 310                 315                 320

Glu Tyr Ser Ile Gly Gln Val Leu Thr Val Phe Phe Ser Val Leu Ile
                325                 330                 335

Gly Ala Phe Ser Val Gly Gln Ala Ser Pro Asn Ile Glu Ala Phe Ala
            340                 345                 350
```

-continued

Asn Ala Arg Gly Ala Ala Tyr Glu Val Phe Lys Ile Ile Asp Asn Lys
        355                 360                 365

Pro Ser Ile Asp Ser Phe Ser Lys Ser Gly His Lys Pro Asp Asn Ile
    370                 375                 380

Gln Gly Asn Leu Glu Phe Lys Asn Ile His Phe Ser Tyr Pro Ser Arg
385                 390                 395                 400

Lys Glu Val Gln Ile Leu Lys Gly Leu Asn Leu Lys Val Lys Ser Gly
                405                 410                 415

Gln Thr Val Ala Leu Val Gly Asn Ser Gly Cys Gly Lys Ser Thr Thr
            420                 425                 430

Val Gln Leu Met Gln Arg Leu Tyr Asp Pro Leu Asp Gly Met Val Ser
        435                 440                 445

Ile Asp Gly Gln Asp Ile Arg Thr Ile Asn Val Arg Tyr Leu Arg Glu
    450                 455                 460

Ile Ile Gly Val Val Ser Gln Glu Pro Val Leu Phe Ala Thr Thr Ile
465                 470                 475                 480

Ala Glu Asn Ile Arg Tyr Gly Arg Glu Asp Val Thr Met Asp Glu Ile
                485                 490                 495

Glu Lys Ala Val Lys Glu Ala Asn Ala Tyr Asp Phe Ile Met Lys Leu
            500                 505                 510

Pro His Gln Phe Asp Thr Leu Val Gly Glu Arg Gly Ala His Val Ser
        515                 520                 525

Gly Gly Gln Lys Gln Arg Ile Ala Ile Ala Arg Ala Leu Val Arg Asn
    530                 535                 540

Pro Lys Ile Leu Leu Leu Asp Glu Ala Thr Ser Ala Leu Asp Thr Glu
545                 550                 555                 560

Ser Glu Ala Val Val Gln Ala Ala Leu Asp Lys Ala Arg Glu Gly Arg
                565                 570                 575

Thr Thr Ile Val Ile Ala His Arg Leu Ser Thr Val Arg Asn Ala Asp
            580                 585                 590

Val Ile Ala Gly Phe Asp Gly Gly Val Ile Val Glu Gln Gly Asn His
        595                 600                 605

Asp Glu Leu Met Arg Glu Lys Gly Ile Tyr Phe Lys Leu Val Met Thr
    610                 615                 620

Gln Thr Ala Gly Asn Glu Ile Glu Leu Gly Asn Glu Ala Cys Lys Ser
625                 630                 635                 640

Lys Asp Glu Ile Asp Asn Leu Asp Met Ser Ser Lys Asp Ser Gly Ser
                645                 650                 655

Ser Leu Ile Arg Arg Arg Ser Thr Arg Lys Ser Ile Cys Gly Pro His
            660                 665                 670

Asp Gln Asp Arg Lys Leu Ser Thr Lys Glu Ala Leu Asp Glu Asp Val
        675                 680                 685

Pro Pro Ala Ser Phe Trp Arg Ile Leu Lys Leu Asn Ser Thr Glu Trp
    690                 695                 700

Pro Tyr Phe Val Val Gly Ile Phe Cys Ala Ile Ile Asn Gly Gly Leu
705                 710                 715                 720

Gln Pro Ala Phe Ser Val Ile Phe Ser Lys Val Val Gly Val Phe Thr
                725                 730                 735

Asn Gly Gly Pro Pro Glu Thr Gln Arg Gln Asn Ser Asn Leu Phe Ser
            740                 745                 750

Leu Leu Phe Leu Ile Leu Gly Ile Ile Ser Phe Ile Thr Phe Phe Leu
        755                 760                 765

Gln Gly Phe Thr Phe Gly Lys Ala Gly Glu Ile Leu Thr Lys Arg Leu

-continued

```
            770                 775                 780
Arg Tyr Met Val Phe Lys Ser Met Leu Arg Gln Asp Val Ser Trp Phe
785                 790                 795                 800

Asp Asp Pro Lys Asn Thr Thr Gly Ala Leu Thr Thr Arg Leu Ala Asn
                805                 810                 815

Asp Ala Ala Gln Val Lys Gly Ala Thr Gly Ser Arg Leu Ala Val Ile
                820                 825                 830

Phe Gln Asn Ile Ala Asn Leu Gly Thr Gly Ile Ile Ile Ser Leu Ile
                835                 840                 845

Tyr Gly Trp Gln Leu Thr Leu Leu Leu Ala Ile Val Pro Ile Ile
850                 855                 860

Ala Ile Ala Gly Val Val Glu Met Lys Met Leu Ser Gly Gln Ala Leu
865                 870                 875                 880

Lys Asp Lys Lys Glu Leu Glu Gly Ser Gly Lys Ile Ala Thr Glu Ala
                885                 890                 895

Ile Glu Asn Phe Arg Thr Val Val Ser Leu Thr Arg Glu Gln Lys Phe
                900                 905                 910

Glu Thr Met Tyr Ala Gln Ser Leu Gln Ile Pro Tyr Arg Asn Ala Met
            915                 920                 925

Lys Lys Ala His Val Phe Gly Ile Thr Phe Ser Phe Thr Gln Ala Met
            930                 935                 940

Met Tyr Phe Ser Tyr Ala Ala Cys Phe Arg Phe Gly Ala Tyr Leu Val
945                 950                 955                 960

Thr Gln Gln Leu Met Thr Phe Glu Asn Val Leu Leu Val Phe Ser Ala
                965                 970                 975

Ile Val Phe Gly Ala Met Ala Val Gly Gln Val Ser Ser Phe Ala Pro
                980                 985                 990

Asp Tyr Ala Lys Ala Thr Val Ser Ala Ser His Ile Ile Arg Ile Ile
            995                 1000                1005

Glu Lys Thr Pro Glu Ile Asp Ser Tyr Ser Thr Gln Gly Leu Lys Pro
    1010                1015                1020

Asn Met Leu Glu Gly Asn Val Gln Phe Ser Gly Val Val Phe Asn Tyr
1025                1030                1035                1040

Pro Thr Arg Pro Ser Ile Pro Val Leu Gln Gly Leu Ser Leu Glu Val
                1045                1050                1055

Lys Lys Gly Gln Thr Leu Ala Leu Val Gly Ser Ser Gly Cys Gly Lys
            1060                1065                1070

Ser Thr Val Val Gln Leu Leu Glu Arg Phe Tyr Asp Pro Met Ala Gly
        1075                1080                1085

Ser Val Phe Leu Asp Gly Lys Glu Ile Lys Gln Leu Asn Val Gln Trp
    1090                1095                1100

Leu Arg Ala Gln Leu Gly Ile Val Ser Gln Glu Pro Ile Leu Phe Asp
1105                1110                1115                1120

Cys Ser Ile Ala Glu Asn Ile Ala Tyr Gly Asp Asn Ser Arg Val Val
                1125                1130                1135

Ser Tyr Glu Glu Ile Val Arg Ala Ala Lys Glu Ala Asn Ile His Gln
            1140                1145                1150

Phe Ile Asp Ser Leu Pro Asp Lys Tyr Asn Thr Arg Val Gly Asp Lys
            1155                1160                1165

Gly Thr Gln Leu Ser Gly Gly Gln Lys Gln Arg Ile Ala Ile Ala Arg
    1170                1175                1180

Ala Leu Val Arg Gln Pro His Ile Leu Leu Leu Asp Glu Ala Thr Ser
1185                1190                1195                1200
```

```
Ala Leu Asp Thr Glu Ser Glu Lys Val Gln Glu Ala Leu Asp Lys
         1205                1210                1215

Ala Arg Glu Gly Arg Thr Cys Ile Val Ile Ala His Arg Leu Ser Thr
         1220                1225                1230

Ile Gln Asn Ala Asp Leu Ile Val Ile Gln Asn Gly Lys Val Lys
         1235                1240                1245

Glu His Gly Thr His Gln Gln Leu Leu Ala Gln Lys Gly Ile Tyr Phe
    1250                1255                1260

Ser Met Val Ser Val Gln Ala Gly Ala Lys Arg Ser
1265            1270                1275

<210> SEQ ID NO 9
<211> LENGTH: 2719
<212> TYPE: DNA
<213> ORGANISM: Homo sapiens
<220> FEATURE:
<221> NAME/KEY: CDS
<222> LOCATION: (205)..(2172)

<400> SEQUENCE: 9
tttaggaacg caccgtgcac atgcttggtg gtcttgttaa gtggaaactg ctgctttaga      60
gtttgtttgg aaggtccggg tgactcatcc caacatttac atccttaatt gttaaagcgc     120
tgcctccgag cgcacgcatc ctgagatcct gagcctttgg ttaagaccga gctctattaa     180
gctgaaaaga taaaaactct ccag atg tct tcc agt aat gtc gaa gtt ttt       231
                         Met Ser Ser Ser Asn Val Glu Val Phe
                          1               5 atc cca gtg tca caa gga aac acc aat ggc ttc ccc gcg aca gtt tcc       279
Ile Pro Val Ser Gln Gly Asn Thr Asn Gly Phe Pro Ala Thr Val Ser
 10              15                  20                  25 aat gac ctg aag gca ttt act gaa gga gct gtg tta agt ttt cat aac       327
Asn Asp Leu Lys Ala Phe Thr Glu Gly Ala Val Leu Ser Phe His Asn
             30                  35                  40 atc tgc tat cga gta aaa ctg aag agt ggc ttt cta cct tgt cga aaa       375
Ile Cys Tyr Arg Val Lys Leu Lys Ser Gly Phe Leu Pro Cys Arg Lys
         45                  50                  55 cca gtt gag aaa gaa ata tta tcg aat atc aat ggg atc atg aaa cct       423
Pro Val Glu Lys Glu Ile Leu Ser Asn Ile Asn Gly Ile Met Lys Pro
     60                  65                  70 ggt ctc aac gcc atc ctg gga ccc aca ggt gga ggc aaa tct tcg tta       471
Gly Leu Asn Ala Ile Leu Gly Pro Thr Gly Gly Gly Lys Ser Ser Leu
 75                  80                  85 tta gat gtc tta gct gca agg aaa gat cca agt gga tta tct gga gat       519
Leu Asp Val Leu Ala Ala Arg Lys Asp Pro Ser Gly Leu Ser Gly Asp
 90                  95                 100                 105 gtt ctg ata aat gga gca ccg cga cct gcc aat ttc aaa tgt aat tca       567
Val Leu Ile Asn Gly Ala Pro Arg Pro Ala Asn Phe Lys Cys Asn Ser
             110                 115                 120 ggt tac gtg gta caa gat gat gtt gtg atg ggc act ctg acg gtg aga       615
Gly Tyr Val Val Gln Asp Asp Val Val Met Gly Thr Leu Thr Val Arg
         125                 130                 135 gaa aac tta cag ttc tca gca gct ctt cgg ctt gca aca act atg acg       663
Glu Asn Leu Gln Phe Ser Ala Ala Leu Arg Leu Ala Thr Thr Met Thr
     140                 145                 150 aat cat gaa aaa aac gaa cgg att aac agg gtc att gaa gag tta ggt       711
Asn His Glu Lys Asn Glu Arg Ile Asn Arg Val Ile Glu Glu Leu Gly
 155                 160                 165 ctg gat aaa gtg gca gac tcc aag gtt gga act cag ttt atc cgt ggt       759
Leu Asp Lys Val Ala Asp Ser Lys Val Gly Thr Gln Phe Ile Arg Gly
```

```
                          170                 175                 180                 185
gtg tct gga gga gaa aga aaa agg act agt ata gga atg gag ctt atc      807
Val Ser Gly Gly Glu Arg Lys Arg Thr Ser Ile Gly Met Glu Leu Ile
                    190                 195                 200 act gat cct tcc atc ttg tcc ttg gat gag cct aca act ggc tta gac      855
Thr Asp Pro Ser Ile Leu Ser Leu Asp Glu Pro Thr Thr Gly Leu Asp
                205                 210                 215 tca agc aca gca aat gct gtc ctt ttg ctc ctg aaa agg atg tct aag      903
Ser Ser Thr Ala Asn Ala Val Leu Leu Leu Leu Lys Arg Met Ser Lys
            220                 225                 230 cag gga cga aca atc atc ttc tcc att cat cag cct cga tat tcc atc      951
Gln Gly Arg Thr Ile Ile Phe Ser Ile His Gln Pro Arg Tyr Ser Ile
        235                 240                 245 ttc aag ttg ttt gat agc ctc acc tta ttg gcc tca gga aga ctt atg      999
Phe Lys Leu Phe Asp Ser Leu Thr Leu Leu Ala Ser Gly Arg Leu Met
250                 255                 260                 265 ttc cac ggg cct gct cag gag gcc ttg gga tac ttt gaa tca gct ggt     1047
Phe His Gly Pro Ala Gln Glu Ala Leu Gly Tyr Phe Glu Ser Ala Gly
                270                 275                 280 tat cac tgt gag gcc tat aat aac cct gca gac ttc ttc ttg gac atc     1095
Tyr His Cys Glu Ala Tyr Asn Asn Pro Ala Asp Phe Phe Leu Asp Ile
            285                 290                 295 att aat gga gat tcc act gct gtg gca tta aac aga gaa gaa gac ttt     1143
Ile Asn Gly Asp Ser Thr Ala Val Ala Leu Asn Arg Glu Glu Asp Phe
        300                 305                 310 aaa gcc aca gag atc ata gag cct tcc aag cag gat aag cca ctc ata     1191
Lys Ala Thr Glu Ile Ile Glu Pro Ser Lys Gln Asp Lys Pro Leu Ile
    315                 320                 325 gaa aaa tta gcg gag att tat gtc aac tcc tcc ttc tac aaa gag aca     1239
Glu Lys Leu Ala Glu Ile Tyr Val Asn Ser Ser Phe Tyr Lys Glu Thr
330                 335                 340                 345 aaa gct gaa tta cat caa ctt tcc ggg ggt gag aag aag aag aag atc     1287
Lys Ala Glu Leu His Gln Leu Ser Gly Gly Glu Lys Lys Lys Lys Ile
                350                 355                 360 aca gtc ttc aag gag atc agc tac acc acc tcc ttc tgt cat caa ctc     1335
Thr Val Phe Lys Glu Ile Ser Tyr Thr Thr Ser Phe Cys His Gln Leu
            365                 370                 375 aga tgg gtt tcc aag cgt tca ttc aaa aac ttg ctg ggt aat ccc cag     1383
Arg Trp Val Ser Lys Arg Ser Phe Lys Asn Leu Leu Gly Asn Pro Gln
        380                 385                 390 gcc tct ata gct cag atc att gtc aca gtc gta ctg gga ctg gtt ata     1431
Ala Ser Ile Ala Gln Ile Ile Val Thr Val Val Leu Gly Leu Val Ile
    395                 400                 405 ggt gcc att tac ttt ggg cta aaa aat gat tct act gga atc cag aac     1479
Gly Ala Ile Tyr Phe Gly Leu Lys Asn Asp Ser Thr Gly Ile Gln Asn
410                 415                 420                 425 aga gct ggg gtt ctc ttc ttc ctg acg acc aac cag tgt ttc agc agt     1527
Arg Ala Gly Val Leu Phe Phe Leu Thr Thr Asn Gln Cys Phe Ser Ser
                430                 435                 440 gtt tca gcc gtg gaa ctc ttt gtg gta gag aag aag ctc ttc ata cat     1575
Val Ser Ala Val Glu Leu Phe Val Val Glu Lys Lys Leu Phe Ile His
            445                 450                 455 gaa tac atc agc gga tac tac aga gtg tca tct tat ttc ctt gga aaa     1623
Glu Tyr Ile Ser Gly Tyr Tyr Arg Val Ser Ser Tyr Phe Leu Gly Lys
        460                 465                 470 ctg tta tct gat tta tta ccc atg agg atg tta cca agt att ata ttt     1671
Leu Leu Ser Asp Leu Leu Pro Met Arg Met Leu Pro Ser Ile Ile Phe
    475                 480                 485 acc tgt ata gtg tac ttc atg tta gga ttg aag cca aag gca gat gcc     1719
```

```
                Thr Cys Ile Val Tyr Phe Met Leu Gly Leu Lys Pro Lys Ala Asp Ala
                490                 495                 500                 505 ttc ttc gtt atg atg ttt acc ctt atg atg gtg gct tat tca gcc agt        1767
Phe Phe Val Met Met Phe Thr Leu Met Met Val Ala Tyr Ser Ala Ser
                    510                 515                 520 tcc atg gca ctg gcc ata gca gca ggt cag agt gtg gtt tct gta gca        1815
Ser Met Ala Leu Ala Ile Ala Ala Gly Gln Ser Val Val Ser Val Ala
                525                 530                 535 aca ctt ctc atg acc atc tgt ttt gtg ttt atg atg att ttt tca ggt        1863
Thr Leu Leu Met Thr Ile Cys Phe Val Phe Met Met Ile Phe Ser Gly
            540                 545                 550 ctg ttg gtc aat ctc aca acc att gca tct tgg ctg tca tgg ctt cag        1911
Leu Leu Val Asn Leu Thr Thr Ile Ala Ser Trp Leu Ser Trp Leu Gln
        555                 560                 565 tac ttc agc att cca cga tat gga ttt acg gct ttg cag cat aat gaa        1959
Tyr Phe Ser Ile Pro Arg Tyr Gly Phe Thr Ala Leu Gln His Asn Glu
570                 575                 580                 585 ttt ttg gga caa aac ttc tgc cca gga ctc aat gca aca gga aac aat        2007
Phe Leu Gly Gln Asn Phe Cys Pro Gly Leu Asn Ala Thr Gly Asn Asn
                590                 595                 600 cct tgt aac tat gca aca tgt act ggc gaa gaa tat ttg gta aag cag        2055
Pro Cys Asn Tyr Ala Thr Cys Thr Gly Glu Glu Tyr Leu Val Lys Gln
            605                 610                 615 ggc atc gat ctc tca ccc tgg ggc ttg tgg aag aat cac gtg gcc ttg        2103
Gly Ile Asp Leu Ser Pro Trp Gly Leu Trp Lys Asn His Val Ala Leu
        620                 625                 630 gct tgt atg att gtt att ttc ctc aca att gcc tac ctg aaa ttg tta        2151
Ala Cys Met Ile Val Ile Phe Leu Thr Ile Ala Tyr Leu Lys Leu Leu
    635                 640                 645 ttt ctt aaa aaa tat tct taa atttcccctt aattcagtat gatttatcct           2202
Phe Leu Lys Lys Tyr Ser
650                 655 cacataaaaa agaagcactt tgattgaagt attcaatcaa gttttttttgt tgttttctgt     2262 tcccttgcca tcacactgtt gcacagcagc aattgtttta aagagataca tttttagaaa      2322
tcacaacaaa ctgaattaaa catgaaagaa cccaagacat catgtatcgc atattagtta      2382
atctcctcag acagtaacca tggggaagaa atctggtcta atttattaat ctaaaaaagg      2442
agaattgaat tctggaaact cctgacaagt tattactgtc tctggcattt gtttcctcat      2502
ctttaaaatg aataggtagg ttagtagccc ttcagtctta atactttatg atgctatggt      2562
ttgccattat ttaatatatg acaaatgtat taatgctata ctggaaatgt aaaattgaaa      2622
atatgttgga aaaaagattc tgtcttatag ggtaaaaaaa gccaccggtg atagaaaaaa      2682 aatcttttttg ataagcacat taagttaat agaactt                              2719

<210> SEQ ID NO 10
<211> LENGTH: 655
<212> TYPE: PRT
<213> ORGANISM: Homo sapiens

<400> SEQUENCE: 10

Met Ser Ser Ser Asn Val Glu Val Phe Ile Pro Val Ser Gln Gly Asn
1               5                   10                  15

Thr Asn Gly Phe Pro Ala Thr Val Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
```

-continued

```
            50                  55                  60
Ser Asn Ile Asn Gly Ile Met Lys Pro Gly Leu Asn Ala Ile Leu Gly
 65                  70                  75                  80

Pro Thr Gly Gly Gly Lys Ser Ser Leu Leu Asp Val Leu Ala Ala Arg
                 85                  90                  95

Lys Asp Pro Ser Gly Leu Ser Gly Asp Val Leu Ile Asn Gly Ala Pro
                100                 105                 110

Arg Pro Ala Asn Phe Lys Cys Asn Ser Gly Tyr Val Gln Asp Asp
                115                 120                 125

Val Val Met Gly Thr Leu Thr Val Arg Glu Asn Leu Gln Phe Ser Ala
130                 135                 140

Ala Leu Arg Leu Ala Thr Thr Met Thr Asn His Glu Lys Asn Glu Arg
145                 150                 155                 160

Ile Asn Arg Val Ile Glu Glu Leu Gly Leu Asp Lys Val Ala Asp Ser
                165                 170                 175

Lys Val Gly Thr Gln Phe Ile Arg Gly Val Ser Gly Glu Arg Lys
                180                 185                 190

Arg Thr Ser Ile Gly Met Glu Leu Ile Thr Asp Pro Ser Ile Leu Ser
                195                 200                 205

Leu Asp Glu Pro Thr Thr Gly Leu Asp Ser Ser Thr Ala Asn Ala Val
                210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
                260                 265                 270

Ala Leu Gly Tyr Phe Glu Ser Ala Gly Tyr His Cys Glu Ala Tyr Asn
                275                 280                 285

Asn Pro Ala Asp Phe Phe Leu Asp Ile Ile Asn Gly Asp Ser Thr Ala
                290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
                340                 345                 350

Ser Gly Gly Glu Lys Lys Lys Ile Thr Val Phe Lys Glu Ile Ser
                355                 360                 365

Tyr Thr Thr Ser Phe Cys His Gln Leu Arg Trp Val Ser Lys Arg Ser
370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
                420                 425                 430

Leu Thr Thr Asn Gln Cys Phe Ser Ser Val Ser Ala Val Glu Leu Phe
                435                 440                 445

Val Val Glu Lys Lys Leu Phe Ile His Glu Tyr Ile Ser Gly Tyr Tyr
                450                 455                 460

Arg Val Ser Ser Tyr Phe Leu Gly Lys Leu Leu Ser Asp Leu Leu Pro
465                 470                 475                 480
```

```
Met Arg Met Leu Pro Ser Ile Ile Phe Thr Cys Ile Val Tyr Phe Met
            485                 490                 495
Leu Gly Leu Lys Pro Lys Ala Asp Ala Phe Phe Val Met Met Phe Thr
            500                 505                 510
Leu Met Met Val Ala Tyr Ser Ala Ser Ser Met Ala Leu Ala Ile Ala
            515                 520                 525
Ala Gly Gln Ser Val Val Ser Val Ala Thr Leu Leu Met Thr Ile Cys
            530                 535                 540
Phe Val Phe Met Met Ile Phe Ser Gly Leu Leu Val Asn Leu Thr Thr
545                 550                 555                 560
Ile Ala Ser Trp Leu Ser Trp Leu Gln Tyr Phe Ser Ile Pro Arg Tyr
                565                 570                 575
Gly Phe Thr Ala Leu Gln His Asn Glu Phe Leu Gly Gln Asn Phe Cys
                580                 585                 590
Pro Gly Leu Asn Ala Thr Gly Asn Asn Pro Cys Asn Tyr Ala Thr Cys
                595                 600                 605
Thr Gly Glu Glu Tyr Leu Val Lys Gln Gly Ile Asp Leu Ser Pro Trp
            610                 615                 620
Gly Leu Trp Lys Asn His Val Ala Leu Ala Cys Met Ile Val Ile Phe
625                 630                 635                 640
Leu Thr Ile Ala Tyr Leu Lys Leu Leu Phe Leu Lys Lys Tyr Ser
                645                 650                 655

<210> SEQ ID NO 11
<211> LENGTH: 502
<212> TYPE: DNA
<213> ORGANISM: Mus musculus
<220> FEATURE:
<221> NAME/KEY: CDS
<222> LOCATION: (1)..(444)

<400> SEQUENCE: 11 ttc ggc cta ggg gcc gag gct tat acg gcc agt tcc atg gca ctg gcc      48
Phe Gly Leu Gly Ala Glu Ala Tyr Thr Ala Ser Ser Met Ala Leu Ala
 1               5                  10                  15 ata gcc aca ggc caa agt gtg gtg tct gta gca aca cta ctc atg aca      96
Ile Ala Thr Gly Gln Ser Val Val Ser Val Ala Thr Leu Leu Met Thr
             20                  25                  30 atc gct ttt gta ttt atg atg ctc ttt tct ggc ctc ttg gtg aat ctc     144
Ile Ala Phe Val Phe Met Met Leu Phe Ser Gly Leu Leu Val Asn Leu
         35                  40                  45 aga acc att ggg cct tgg ctg tcc tgg ctt cag tac ttt agc att cct     192
Arg Thr Ile Gly Pro Trp Leu Ser Trp Leu Gln Tyr Phe Ser Ile Pro
     50                  55                  60 cga tat ggc ttc aca gct ttg cag tat aat gaa ttc ttg gga caa gag     240
Arg Tyr Gly Phe Thr Ala Leu Gln Tyr Asn Glu Phe Leu Gly Gln Glu
 65                  70                  75                  80 ttt tgt cca gga ttc aat gta acg gac aac agc act tgt gtt aac agc     288
Phe Cys Pro Gly Phe Asn Val Thr Asp Asn Ser Thr Cys Val Asn Ser
                 85                  90                  95 tat gca ata tgt act ggt aac gag tac ttg ata aat cag ggc atc gaa     336
Tyr Ala Ile Cys Thr Gly Asn Glu Tyr Leu Ile Asn Gln Gly Ile Glu
            100                 105                 110 ctg tca cct tgg gga ctg tgg aag aat cat gtg gcc ctg gct tgt atg     384
Leu Ser Pro Trp Gly Leu Trp Lys Asn His Val Ala Leu Ala Cys Met
        115                 120                 125 att att atc ttc ctc aca att gcc tac ctg aaa ttg ttg ttt ctt aaa     432
Ile Ile Ile Phe Leu Thr Ile Ala Tyr Leu Lys Leu Leu Phe Leu Lys
```

-continued

```
        130                 135                 140
aag tat tct taa tttcccctttt aacggactat taattgtact ccaattaaat        484
Lys Tyr Ser
145 atgggcactt tgattacc                                                  502
```

<210> SEQ ID NO 12
<211> LENGTH: 147
<212> TYPE: PRT
<213> ORGANISM: Mus musculus

<400> SEQUENCE: 12

```
Phe Gly Leu Gly Ala Glu Ala Tyr Thr Ala Ser Ser Met Ala Leu Ala
 1               5                  10                  15

Ile Ala Thr Gly Gln Ser Val Val Ser Val Ala Thr Leu Leu Met Thr
            20                  25                  30

Ile Ala Phe Val Phe Met Met Leu Phe Ser Gly Leu Leu Val Asn Leu
        35                  40                  45

Arg Thr Ile Gly Pro Trp Leu Ser Trp Leu Gln Tyr Phe Ser Ile Pro
    50                  55                  60

Arg Tyr Gly Phe Thr Ala Leu Gln Tyr Asn Glu Phe Leu Gly Gln Glu
65                  70                  75                  80

Phe Cys Pro Gly Phe Asn Val Thr Asp Asn Ser Thr Cys Val Asn Ser
                85                  90                  95

Tyr Ala Ile Cys Thr Gly Asn Glu Tyr Leu Ile Asn Gln Gly Ile Glu
            100                 105                 110

Leu Ser Pro Trp Gly Leu Trp Lys Asn His Val Ala Leu Ala Cys Met
        115                 120                 125

Ile Ile Ile Phe Leu Thr Ile Ala Tyr Leu Lys Leu Leu Phe Leu Lys
    130                 135                 140

Lys Tyr Ser
145
```

<210> SEQ ID NO 13
<211> LENGTH: 2025
<212> TYPE: DNA
<213> ORGANISM: Mus musculus
<220> FEATURE:
<221> NAME/KEY: CDS
<222> LOCATION: (20)..(1993)

<400> SEQUENCE: 13

```
aaaggcataa atcctaaag atg tct tcc agt aat gac cac gtg tta gta cca       52
                    Met Ser Ser Ser Asn Asp His Val Leu Val Pro
                     1               5                  10 atg tcg cag aga aac aac aac ggc ctt cct agg atg aac tcc aga gcc      100
Met Ser Gln Arg Asn Asn Asn Gly Leu Pro Arg Met Asn Ser Arg Ala
             15                  20                  25 gtt agg acg ctc gca gaa gga gat gtg ttg agt ttt cat cac atc acc      148
Val Arg Thr Leu Ala Glu Gly Asp Val Leu Ser Phe His His Ile Thr
         30                  35                  40 tat cga gtg aaa gta aag agt ggg ttt cta gtc cgg aaa aca gtt gag      196
Tyr Arg Val Lys Val Lys Ser Gly Phe Leu Val Arg Lys Thr Val Glu
    45                  50                  55 aaa gaa ata cta tca gat atc aat ggg atc atg aaa cct ggc ctt aat      244
Lys Glu Ile Leu Ser Asp Ile Asn Gly Ile Met Lys Pro Gly Leu Asn
60                  65                  70                  75 gct att ctg gga ccc aca ggc gga ggc aag tct tcg ttg cta gat gtc      292
Ala Ile Leu Gly Pro Thr Gly Gly Gly Lys Ser Ser Leu Leu Asp Val
                80                  85                  90
```

```
                80                  85                  90
tta gca gca agg aaa gat cca aag gga tta tct gga gat gtt ttg ata      340
Leu Ala Ala Arg Lys Asp Pro Lys Gly Leu Ser Gly Asp Val Leu Ile
             95                 100                 105 aat gga gca cct caa cct gcc cat ttc aaa tgc tgt tca ggt tat gtg      388
Asn Gly Ala Pro Gln Pro Ala His Phe Lys Cys Cys Ser Gly Tyr Val
        110                 115                 120 gtt caa gat gac gtt gtg atg ggc acc ctg aca gtg aga gaa aac tta      436
Val Gln Asp Asp Val Val Met Gly Thr Leu Thr Val Arg Glu Asn Leu
    125                 130                 135 cag ttc tca gca gct ctt cga ctt cca aca act atg aag aat cat gaa      484
Gln Phe Ser Ala Ala Leu Arg Leu Pro Thr Thr Met Lys Asn His Glu
140                 145                 150                 155 aaa aat gaa cgg att aac aca atc att aaa gag tta ggt ctg gaa aaa      532
Lys Asn Glu Arg Ile Asn Thr Ile Ile Lys Glu Leu Gly Leu Glu Lys
                160                 165                 170 gta gca gat tct aag gtc gga act cag ttt atc cgt ggc atc tct gga      580
Val Ala Asp Ser Lys Val Gly Thr Gln Phe Ile Arg Gly Ile Ser Gly
            175                 180                 185 gga gaa aga aaa agg aca agc ata ggg atg gag ctg atc act gac cct      628
Gly Glu Arg Lys Arg Thr Ser Ile Gly Met Glu Leu Ile Thr Asp Pro
        190                 195                 200 tcc atc ctc ttc ctg gat gag ccc acg act ggt ttg gac tca agc aca      676
Ser Ile Leu Phe Leu Asp Glu Pro Thr Thr Gly Leu Asp Ser Ser Thr
    205                 210                 215 gcg aat gct gtc ctt ttg ctc ctg aaa agg atg tct aaa cag ggt cga      724
Ala Asn Ala Val Leu Leu Leu Leu Lys Arg Met Ser Lys Gln Gly Arg
220                 225                 230                 235 aca atc atc ttc tcc att cat cag cct cgg tat tcc atc ttt aag ttg      772
Thr Ile Ile Phe Ser Ile His Gln Pro Arg Tyr Ser Ile Phe Lys Leu
                240                 245                 250 ttt gac agc ctc acc tta ctg gct tcc ggg aaa ctc gtg ttc cat ggg      820
Phe Asp Ser Leu Thr Leu Leu Ala Ser Gly Lys Leu Val Phe His Gly
            255                 260                 265 cca gca cag aag gcc ttg gag tac ttt gca tca gca ggt tac cac tgt      868
Pro Ala Gln Lys Ala Leu Glu Tyr Phe Ala Ser Ala Gly Tyr His Cys
        270                 275                 280 gag ccc tac aac aac cct gcg gat ttt ttc ctt gat gtc atc aat gga      916
Glu Pro Tyr Asn Asn Pro Ala Asp Phe Phe Leu Asp Val Ile Asn Gly
    285                 290                 295 gat tct tct gct gtg atg tta aat aga gag gaa caa gac aat gaa gca      964
Asp Ser Ser Ala Val Met Leu Asn Arg Glu Glu Gln Asp Asn Glu Ala
300                 305                 310                 315 aac aag act gaa gag cct tcc aag gga gag aag cca gta ata gaa aat     1012
Asn Lys Thr Glu Glu Pro Ser Lys Gly Glu Lys Pro Val Ile Glu Asn
                320                 325                 330 tta tct gag ttt tat atc aac tct gcc atc tat gga gaa aca aaa gct     1060
Leu Ser Glu Phe Tyr Ile Asn Ser Ala Ile Tyr Gly Glu Thr Lys Ala
            335                 340                 345 gaa tta gat caa ctt cca gga gct cag gaa aag aaa gga aca tcg gcc     1108
Glu Leu Asp Gln Leu Pro Gly Ala Gln Glu Lys Lys Gly Thr Ser Ala
        350                 355                 360 ttc aaa gag cca gtc tat gtt acc tct ttc tgt cac cag ctc cga tgg     1156
Phe Lys Glu Pro Val Tyr Val Thr Ser Phe Cys His Gln Leu Arg Trp
    365                 370                 375 att gcc agg cgc tca ttt aaa aac ttg ctc ggg aac cct caa gct tct     1204
Ile Ala Arg Arg Ser Phe Lys Asn Leu Leu Gly Asn Pro Gln Ala Ser
380                 385                 390                 395 gtt gct cag tta att gtt aca gtc ata ctg ggg ctt att att ggt gcc     1252
```

```
Val Ala Gln Leu Ile Val Thr Val Ile Leu Gly Leu Ile Ile Gly Ala
                400                 405                 410 att tac ttt gat ctg aaa tat gat gcc gct gga atg caa aat aga gct      1300
Ile Tyr Phe Asp Leu Lys Tyr Asp Ala Ala Gly Met Gln Asn Arg Ala
                415                 420                 425 gga gtt ttg ttt ttc ctg act acc aac cag tgt ttt tcc agt gtg tca      1348
Gly Val Leu Phe Phe Leu Thr Thr Asn Gln Cys Phe Ser Ser Val Ser
                430                 435                 440 gct gtg gag ctg ttc gta gtg gag aag aaa ctc ttc ata cat gag tac      1396
Ala Val Glu Leu Phe Val Val Glu Lys Lys Leu Phe Ile His Glu Tyr
                445                 450                 455 atc agt gga tat tac aga gtg tct tct tac ttc ttt gga aag gtg atg      1444
Ile Ser Gly Tyr Tyr Arg Val Ser Ser Tyr Phe Phe Gly Lys Val Met
460                 465                 470                 475 tct gat tta ctc ccc atg agg ttc ttg cca agt gtt ata ttc act tgt      1492
Ser Asp Leu Leu Pro Met Arg Phe Leu Pro Ser Val Ile Phe Thr Cys
                480                 485                 490 ata tta tac ttc atg tta gga ctg aag aag acg gtg gat gct ttt ttc      1540
Ile Leu Tyr Phe Met Leu Gly Leu Lys Lys Thr Val Asp Ala Phe Phe
                495                 500                 505 atc atg atg ttt acc ctt ata atg gtg gct tat acg gcc agt tcc atg      1588
Ile Met Met Phe Thr Leu Ile Met Val Ala Tyr Thr Ala Ser Ser Met
                510                 515                 520 gca ctg gcc ata gcc aca ggc caa agt gtg gtg tct gta gca aca ctt      1636
Ala Leu Ala Ile Ala Thr Gly Gln Ser Val Val Ser Val Ala Thr Leu
                525                 530                 535 ctc atg aca atc gct ttt gta ttt atg atg ctc ttt tct ggc ctc ttg      1684
Leu Met Thr Ile Ala Phe Val Phe Met Met Leu Phe Ser Gly Leu Leu
540                 545                 550                 555 gtg aat ctc aga acc att ggg cct tgg ctg tcc tgg ctt cag tac ttt      1732
Val Asn Leu Arg Thr Ile Gly Pro Trp Leu Ser Trp Leu Gln Tyr Phe
                560                 565                 570 agc att cct cga tat ggc ttc aca gct ttg cag tat aat gaa ttc ttg      1780
Ser Ile Pro Arg Tyr Gly Phe Thr Ala Leu Gln Tyr Asn Glu Phe Leu
                575                 580                 585 gga caa gag ttt tgt cca gga ttc aat gta acg gac aac agc act tgt      1828
Gly Gln Glu Phe Cys Pro Gly Phe Asn Val Thr Asp Asn Ser Thr Cys
                590                 595                 600 gtt aac agc tat gca ata tgt act ggt aac gag tac ttg ata aat cag      1876
Val Asn Ser Tyr Ala Ile Cys Thr Gly Asn Glu Tyr Leu Ile Asn Gln
                605                 610                 615 ggc atc gaa ctg tca cct tgg gga ctg tgg aag aat cat gtg gcc ctg      1924
Gly Ile Glu Leu Ser Pro Trp Gly Leu Trp Lys Asn His Val Ala Leu
620                 625                 630                 635 gct tgt atg att att atc ttc ctc aca att gcc tac ctg aaa ttg ttg      1972
Ala Cys Met Ile Ile Ile Phe Leu Thr Ile Ala Tyr Leu Lys Leu Leu
                640                 645                 650 ttt ctt aaa aag tat tct taa tttcccttt aacggactat taattgtact cc      2025
Phe Leu Lys Lys Tyr Ser
                655

<210> SEQ ID NO 14
<211> LENGTH: 657
<212> TYPE: PRT
<213> ORGANISM: Mus musculus

<400> SEQUENCE: 14

Met Ser Ser Ser Asn Asp His Val Leu Val Pro Met Ser Gln Arg Asn
1               5                   10                  15

Asn Asn Gly Leu Pro Arg Met Asn Ser Arg Ala Val Arg Thr Leu Ala
```

-continued

```
                20                  25                  30
Glu Gly Asp Val Leu Ser Phe His His Ile Thr Tyr Arg Val Lys Val
             35                  40                  45
Lys Ser Gly Phe Leu Val Arg Lys Thr Val Glu Lys Glu Ile Leu Ser
         50                  55                  60
Asp Ile Asn Gly Ile Met Lys Pro Gly Leu Asn Ala Ile Leu Gly Pro
 65                  70                  75                  80
Thr Gly Gly Gly Lys Ser Ser Leu Leu Asp Val Leu Ala Ala Arg Lys
                 85                  90                  95
Asp Pro Lys Gly Leu Ser Gly Asp Val Leu Ile Asn Gly Ala Pro Gln
                100                 105                 110
Pro Ala His Phe Lys Cys Cys Ser Gly Tyr Val Val Gln Asp Asp Val
                115                 120                 125
Val Met Gly Thr Leu Thr Val Arg Glu Asn Leu Gln Phe Ser Ala Ala
            130                 135                 140
Leu Arg Leu Pro Thr Thr Met Lys Asn His Glu Lys Asn Glu Arg Ile
145                 150                 155                 160
Asn Thr Ile Ile Lys Glu Leu Gly Leu Glu Lys Val Ala Asp Ser Lys
                165                 170                 175
Val Gly Thr Gln Phe Ile Arg Gly Ile Ser Gly Gly Glu Arg Lys Arg
            180                 185                 190
Thr Ser Ile Gly Met Glu Leu Ile Thr Asp Pro Ser Ile Leu Phe Leu
        195                 200                 205
Asp Glu Pro Thr Thr Gly Leu Asp Ser Ser Thr Ala Asn Ala Val Leu
    210                 215                 220
Leu Leu Leu Lys Arg Met Ser Lys Gln Gly Arg Thr Ile Ile Phe Ser
225                 230                 235                 240
Ile His Gln Pro Arg Tyr Ser Ile Phe Lys Leu Phe Asp Ser Leu Thr
                245                 250                 255
Leu Leu Ala Ser Gly Lys Leu Val Phe His Gly Pro Ala Gln Lys Ala
            260                 265                 270
Leu Glu Tyr Phe Ala Ser Ala Gly Tyr His Cys Glu Pro Tyr Asn Asn
        275                 280                 285
Pro Ala Asp Phe Phe Leu Asp Val Ile Asn Gly Asp Ser Ser Ala Val
    290                 295                 300
Met Leu Asn Arg Glu Glu Gln Asp Asn Glu Ala Asn Lys Thr Glu Glu
305                 310                 315                 320
Pro Ser Lys Gly Glu Lys Pro Val Ile Glu Asn Leu Ser Glu Phe Tyr
                325                 330                 335
Ile Asn Ser Ala Ile Tyr Gly Glu Thr Lys Ala Glu Leu Asp Gln Leu
            340                 345                 350
Pro Gly Ala Gln Glu Lys Lys Gly Thr Ser Ala Phe Lys Glu Pro Val
        355                 360                 365
Tyr Val Thr Ser Phe Cys His Gln Leu Arg Trp Ile Ala Arg Arg Ser
    370                 375                 380
Phe Lys Asn Leu Leu Gly Asn Pro Gln Ala Ser Val Ala Gln Leu Ile
385                 390                 395                 400
Val Thr Val Ile Leu Gly Leu Ile Ile Gly Ala Ile Tyr Phe Asp Leu
                405                 410                 415
Lys Tyr Asp Ala Ala Gly Met Gln Asn Arg Ala Gly Val Leu Phe Phe
            420                 425                 430
Leu Thr Thr Asn Gln Cys Phe Ser Ser Val Ser Ala Val Glu Leu Phe
        435                 440                 445
```

```
                                        -continued

Val Val Glu Lys Lys Leu Phe Ile His Glu Tyr Ile Ser Gly Tyr Tyr
        450                 455                 460

Arg Val Ser Ser Tyr Phe Phe Gly Lys Val Met Ser Asp Leu Leu Pro
465                 470                 475                 480

Met Arg Phe Leu Pro Ser Val Ile Phe Thr Cys Ile Leu Tyr Phe Met
                485                 490                 495

Leu Gly Leu Lys Lys Thr Val Asp Ala Phe Phe Ile Met Met Phe Thr
                500                 505                 510

Leu Ile Met Val Ala Tyr Thr Ala Ser Ser Met Ala Leu Ala Ile Ala
            515                 520                 525

Thr Gly Gln Ser Val Val Ser Val Ala Thr Leu Leu Met Thr Ile Ala
            530                 535                 540

Phe Val Phe Met Met Leu Phe Ser Gly Leu Leu Val Asn Leu Arg Thr
545                 550                 555                 560

Ile Gly Pro Trp Leu Ser Trp Leu Gln Tyr Phe Ser Ile Pro Arg Tyr
                565                 570                 575

Gly Phe Thr Ala Leu Gln Tyr Asn Glu Phe Leu Gly Gln Glu Phe Cys
                580                 585                 590

Pro Gly Phe Asn Val Thr Asp Asn Ser Thr Cys Val Asn Ser Tyr Ala
            595                 600                 605

Ile Cys Thr Gly Asn Glu Tyr Leu Ile Asn Gln Gly Ile Glu Leu Ser
        610                 615                 620

Pro Trp Gly Leu Trp Lys Asn His Val Ala Leu Ala Cys Met Ile Ile
625                 630                 635                 640

Ile Phe Leu Thr Ile Ala Tyr Leu Lys Leu Leu Phe Leu Lys Lys Tyr
                645                 650                 655

Ser

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer.

<400> SEQUENCE: 15
ccacgtcagc cttggacaca                                                 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer.

<400> SEQUENCE: 16
gccgcttggt gaggatctct                                                 20
```